United States Patent
Li et al.

(10) Patent No.: US 8,053,581 B2
(45) Date of Patent: Nov. 8, 2011

(54) TRISUBSTITUTED THIAZOLE COMPOUNDS, PREPARATIONS METHODS, PHARMACEUTICAL COMPOSITIONS AND MEDICALS USES THEREOF

(75) Inventors: Song Li, Beijing (CN); Changbin Guo, Beijing (CN); Xiancheng Jiang, Beijing (CN); Junhai Xiao, Beijing (CN); Zhong Wu, Beijing (CN)

(73) Assignee: Institute of Pharmacology and Toxicology Academy of Military Medical Sciences P.L.C. China, Beijing (CN)

( * ) Notice: Subject to any disclaimer, the term of this patent is extended or adjusted under 35 U.S.C. 154(b) by 0 days.

(21) Appl. No.: 12/306,499

(22) PCT Filed: Aug. 15, 2006

(86) PCT No.: PCT/CN2006/002071
§ 371 (c)(1),
(2), (4) Date: Jul. 8, 2009

(87) PCT Pub. No.: WO2008/006257
PCT Pub. Date: Jan. 17, 2008

(65) Prior Publication Data
US 2009/0298832 A1    Dec. 3, 2009

(30) Foreign Application Priority Data

Jun. 27, 2006   (CN) .......................... 2006 1 0090513

(51) Int. Cl.
*C07D 277/44*   (2006.01)
*A61K 31/425*   (2006.01)
(52) U.S. Cl. ......... 548/195; 548/197; 514/370; 514/371
(58) Field of Classification Search ........................ None
See application file for complete search history.

(56) References Cited

U.S. PATENT DOCUMENTS

| | | | |
|---|---|---|---|
| 4,769,062 A | 9/1988 | Lange et al. | |
| 5,314,889 A | 5/1994 | Boigegrain et al. | |
| 5,502,202 A | 3/1996 | Nakazato et al. | |
| 5,568,161 A | 10/1996 | Fulmer, Sr. | |
| 6,407,121 B1 | 6/2002 | Nagamine et al. | |
| 6,605,629 B1 | 8/2003 | Momose et al. | |
| 2001/0044545 A1 | 11/2001 | Dhanoa et al. | |
| 2003/0134859 A1 | 7/2003 | Amemiya | |
| 2005/0043341 A1 | 2/2005 | Gielen | |
| 2007/0004711 A1* | 1/2007 | Zhang et al. | 514/227.5 |

FOREIGN PATENT DOCUMENTS

| | | |
|---|---|---|
| EP | 0 267 986 A1 | 5/1986 |
| EP | 0 518 731 A1 | 12/1992 |
| EP | 0 790 057 A1 | 8/1997 |
| EP | 1 020 439 A1 | 7/2000 |
| EP | 1 352 650 A1 | 10/2003 |
| EP | 1 486 490 A1 | 12/2004 |
| JP | 06-256326 | 9/1994 |
| JP | 7-149745 | 6/1995 |
| JP | 2003292485 A * | 10/2003 |
| JP | 2003-064056 | 3/2005 |
| WO | WO 03/028727 A1 | 4/2003 |
| WO | WO 03/035602 A1 | 5/2003 |
| WO | 2004/096798 | 11/2004 |
| WO | WO 2005026137 A2 * | 3/2005 |

OTHER PUBLICATIONS

Ahluwalia, V.K. et al., "Acid Catalyzed Condensation of Isoprene with Hydroxypropiophenones: Synthesis of 2,2-Dimethylchromans & Some New 2-Amino- & 2-Mercapto-4-Aryl-5-Methylthiazoles," *Indian J. Chem.* (1988) 27B, pp. 629-632.
Joshi, K.C. et al., "Organic Pesticides. Part X. Preparation of Some 2-Amino-4-Aryl-5-Alkylthiazoles and Related Compounds, N-Substituted Aminothiazoles and Their Mercurials, and 2-p-Fluorophenylimino-4-thiazolidone and its Condensation Products," *J. Indian Chem. Soc.* (1962) 39, pp. 121-128.
Khan, R.H. et al., "Synthesis of Fluoroarylthiazoles and Related Compounds as Possible Fungicides," *Agricultural & Biological Chem.* (1976) 40, pp. 1129-1135.
International Search Report—PCT/CN2006/002071—mailed on Apr. 2, 2007.
V. K. Ahluwalia et al., "Acid Catalysed Condensation of Isoprene with Hydroxypropiophenones: Synthesis of 2,2-Dimethylchromans & Some New 2-Amino- & 2-Mercapto-4-aryl-5-methylthiazoles," *Indian Journal of Chemistry*, vol. 27B, pp. 629-632 (1988).
J. Gieldanowski et al., "Pharmacological Activity in the Group of New Substituted Thiazoloacetic and Thiazinocarboxyl Acid Derivatives," *Archivum Immunologiae et Therapiae Experimentalis*, vol. 26, pp. 921-929 (1978).
H. Nagatomi et al., "Studies on the Anti-inflammatory Activity and Ulcerogenic Adverse Effect of Thiazole Derivatives, Especially 2-Amino-thiazoleacetic Acid Derivatives," vol. 5, pp. 599-603 (1984).

(Continued)

*Primary Examiner* — Kamal Saeed
*Assistant Examiner* — Nyeemah A Grazier
(74) *Attorney, Agent, or Firm* — Brinks Hofer Gilson & Lione

(57) ABSTRACT

The present invention relates to 2,4,5-trisubstituted thiazole compounds of formula (I) or all possible isomers, prodrugs, pharmaceutically acceptable salts, solvates or hydrates thereof for the inhibition of plasma PLTP activity and/or plasma CETP activity, wherein the substituents are as defined in the specification; a process for the preparation of the compounds of formula (I); a pharmaceutical composition comprising the compound of formula (I) and its use for the preparation of a medicament for treatment and/or prevention of diseases associated with the increased plasma PLTP activity and/or the increased plasma CETP activity in a mammal, such as atherosclerosis, cardiovascular diseases and peripheral vascular diseases, etc.

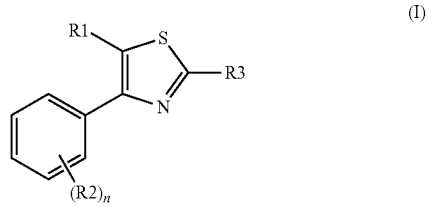

(I)

4 Claims, No Drawings

OTHER PUBLICATIONS

K. Hirai et al., "Syntheses of 2-Disubstituted-amino-4-arylthiazol-5-ylalkanoic acids," *Chem. Pharm. Bull.*, vol. 25, pp. 2292-2299 (1977).

Extended European Search Report, European Patent Application No. 06775389.7 (May 26, 2011).

* cited by examiner

TRISUBSTITUTED THIAZOLE COMPOUNDS, PREPARATIONS METHODS, PHARMACEUTICAL COMPOSITIONS AND MEDICALS USES THEREOF

TECHNICAL FIELD

The present invention relates to 2,4,5-trisubstituted thiazole compounds used as phospholipids transfer protein (PLTP) inhibitors and/or cholesteryl ester transfer protein (CEPT) inhibitors, their preparation method and use in medical field, especially for the preparation of a medicament for the treatment and prevention of diseases associated with the increased plasma PLTP activity and/or the rise of plasma CETP activity, said diseases include atherosclerosis, cardiovascular diseases and peripheral vascular diseases, etc.

BACKGROUND OF THE INVENTION

Diseases induced by atherosclerosis are the first death cause in developed countries. In China, with the development of social economy and the aging of population, morbidity and mortality of cardio-cerebrovascular diseases have increased significantly in recent years. The origin and pathology of atherosclerosis are complex and have not been elucidated completely at present, but it is known that they are closely related to following factors: blood-fat abnormality, hypertension, diabetes, obesity, smoking, and so on. In these factors, the most important factor to induce the formation of atherosclerosis is blood-fat abnormality. Blood-fat abnormality mainly appears as the rise of LDL cholesterol level and descent of HDL cholesterol level.

Phospholipid transfer protein (PLTP) was called as fat transfer protein II previously, it is glucoprotein present in blood plasma and can mediate the net transfer and exchange of phospholipids between phospholipid vesicle and high-density lipoprotein (HDL) and between main lipoproteins. PLTP contains 476 amino acids residues distributing in all tissues. It exhibits high expression in placenta, pancreatic gland, fat tissue and lung, and low expression in liver, kidney and heart. Its biological synthesis is mainly completed in liver and fat tissue. There are two kinds of PLTP in blood plasma, one of which is high activity form (binding to apo E), and the other is low activity form (binding to apo A-I). The high activity form accounts for 46% in blood plasma (Tol, A. V. 2002; Janis M. T., Siggins S., Tahvanainen E., et al. J. Lipid. Res. 2004; 45(12):2303-2309). PLTP plays a very important role in the metabolism of lipoprotein.

PLTP has three principal actions in the metabolism of lipoproteins: the first action is phospholipid transfer activity, i.e., transferring phospholipids from surface remaining particles of chylomicron, very low-density lipoprotein (VLDL) and low-density lipoprotein (LDL) in lipolysis to HDL to increase HDL particles; the second action is remodeling HDL, i.e., regulating the particle size and subclass composition of HDL, mediating the fusing of two $HDL_3$ particles, producing macrobeads of $HDL_2$ and pre-β-HDL, moreover, phospholipid transfer is precondition to remodel HDL, pre-β-HDL is an effective acceptor of cholesterol during antiport of cholesterol; the third action is to regulate liver cells to secrete apolipoprotein B (apoB), to increase the content of VLDL in blood, PLTP deficiency leads to the reduction of VLDL secretion. Besides, PLTP participates in the transfer of vitamin E from lipoprotein to cell membrane, if its activity is reduced, it can increase the VE content in lipoproteins (VLDL and LDL) containing apo B, and antioxidation action of lipoproteins is improved; PLTP further has the activity to transfer lipopolysaccharide to enhance the response of organism to inflammation (Huuskonen J., Olkkonen V. M., Jauhiainen M., Ehnholm C. Atherosclerosis 2001, 155, 269-281; Albers J. J., Cheung M. C. Current Opinion in Lipidology 2004, 15, 255-260; Huuskonen J., Olkkonen V. M., Ehnholm C. et al. Biochemistry 2000, 39, 16092-16098).

PLTP and CETP both belong to fat transporting/lipopolysaccharide binding protein family. The protein family has four members, the other members are bactericidal permeability increasing protein (BPI) and lipopolysaccharide binding protein (LBP)). CETP was called as fat transfer protein I previously, which mediates the transfer of neutral fats such as cholesterol ester, etc. from HDL to LDL, and consequently reduces the particles of HDL. It has been found that human heritage deficiency of CEPT leads to significant rise of HDL level and moderate descent of LDL level, and thereby the research and development of CETP inhibitors have been initiated (Brown M. L., Inazu A., Hesler C. B. et al. Nature 1989, 342, 448-451). Clinic studies showed that CETP inhibitors can elevate HDL, and thus can be used for prevention and treatment of atherosclerosis. CETP inhibitors Torcetrapib (Brousseau M. E., Schaefer E. J., Wolfe M. L. et al. N. Engl. J. Med. 2004, 350, 1505-1515) and JTT-705 (de Grooth G. J., Kuivenhoven J. A., Stalenhoef A. F. et al. Circulation 2002, 105, 2159-2165) have been respectively in III and II phases of clinic trials. In III phase of clinic trials, Torcetrapib is used in combination with Atorvastatin for anti-atherosclerosis and treatment of blood fat abnormality.

In these four members, only X-ray diffraction crystal structure of human BPI has been reported. The crystal structure of BPI has shown that it is in boomerang shape, consists of two subunits, and takes on pseudosymmetric structure. In two concave surfaces of the boomerang, there are respectively two non-polar pockets, which each binds one lecithin molecule, mainly interacts with acyl chain of phospholipids, therefore it has been presumed that BPI binds the acyl chain of lipopolysaccharides. From the structure of BPI can be supposed the mechanism for the fat conveying protein family to convey fat, in which two non-polar pockets are its main functional structure (Beamer L. J., Carroll S. F., Eisenberg D. Science 1997, 276, 1861-1864). Huuskonen et al. have homologically modeled the structure of PLTP with BPI as template protein. Research on amino acid directed mutagenesis has shown that the N-terminal pocket of PLTP is very important to phospholipid transfer activity, and the C-terminal pocket thereof mainly functions to bind HDL (Huuskonen J., Wohlfahrt G, Jauhiainen M. et al. J. Lipid Res. 1999, 40, 1123-1130; Ponsin G., Qu S. J., Fan H. Z. et al. Biochemistry 2003, 42, 4444-4451).

Research results in epidemiology have shown that PLTP content in blood plasma of patients suffering from coronary artery diseases is remarkably higher than that of control group (25.5 vs 22.4 pmol/μL/h; P<0.0001). The probability of one-fifth of the patients in which the PLTP content in blood plasma is the highest suffering from coronary artery diseases is 1.9 times more than that of one-fifth of the patients in which the PLTP content in blood plasma is the lowest. Multivariable regression analysis has shown that after the correction of the factors such as age, blood plasma fat, smoking, diabetes, hypertension, etc. PLTP activity is an independent factor affecting the anticipation of coronary heart diseases. The rise of phospholipid transfer protein level in blood plasma is a danger factor of coronary artery diseases (Schlitt A., Bickel C., Thumma P. et al. Arterioscler Thromb. Vasc. Biol. 2003, 23(10), 1857-62). Blood plasma PLTP activity is elevated in the patients suffering from diabetes I stage and II stage, obesity and insulin tolerance symptoms (Tol, A. V 2002).

The PLTP activity level in blood plasma of transgenic mice in which human PLTP is over-expressed elevated by 2.5-4.5 times, so that blood plasma HDL cholesterol level is reduced by 30-40% as compared with that of wild type animals, and simultaneously the capability of formatting pro-β-HDL is enhanced (Van Haperen R., van Tol A. Vermeulen P. et al. Arterioscler Thromb Vasc Biol. 2000, 20, 1082-1088). Overexpression of PLTP in heterozygote mice with deficiency of LDL receptors causes PLTP activity to be increased by 1.3-2 times, thereby dose-dependently increasing the damage of atherosclerosis (Yang X. P., Yan D., Qiao C. et al. Arterioscler Thromb. Vasc. Boil. 2003, 23, 1601-1607).

The secretion of apolipoprotein B in PLTP gene knockout mice liver was reduced, which causes the secretion of VLDL to be decreased and anti-oxidation capability of lipoprotein to be enchanced, thereby the anti-inflammation action of HDL is improved, and the damage which suffer from coronary artery diseases is significantly decreased (Jiang X. C., Zhou H. W Curr. Opin. Lipidol. 2006, 17, 302-308; Jiang X. C., Qin S., Qiao C. et al. Nat. Med. 2001, 7, 847-852). Feeding mice with deficiency of PLTP with high fat food did not cause blood plasma lipoprotein abnormality, but interfered the transfer of all main blood plasma phospholipids from VLDL to HDL, thereby remarkably reduced HDL level (Jiang, X. C.; Bruce, C.; Mar, J. et al. J. Clin. Invest. 1999, 103, 907-914). The secretion of VLDL in the liver of mice in which PLTP is over-expressed is increased by 48%, this proves from opposite aspect that the crucial action of PLTP to the secretion of VLDL (Lie J., de Crom R., van G. T. et al. J. Lipid Res. 2002, 43(11), 1875-80). The causes for PLTP deficient state to enhance anti-oxidation capability of blood plasma lipoprotein are the increase of vitamin E accumulation and the increase of the bioavailability of vitamin E in lipoproteins (LDL and VLDL) inducing atherosclerosis (Jiang X. C., Tall A. R., QIn S. et al. J. Biol. Chem. 2002, 277(35), 31850-56). Schlitt et al. has reported that mice with deficiency of PLTP exhibit enhanced organism anti-inflammation capability (Schlitt A., Liu J., Yan D. et al. Biochim Biophys Acta. 2005, 1733(2-3), 187-91).

In summary, reducing blood plasma PLTP activity has anti-atherosclerosis effect, which at least has following three action mechanisms: the first one is to decrease the secretion of apolipoprotein B in liver so as to make the secretion level of VLDL reduced; the second one is to enhance the anti-oxidation action of LDL and mitigate the formation of atherosclerosis caused by oxidation of LDL; the third one is to enhance anti-inflammation capability of organism and mitigate the damage of atherosclerosis induced by inflammation. Therefore, PLTP inhibitor is target of novel pharmaceuticals for the prevention and treatment of atherosclerosis.

PLTP and CEPT are both members of fat conveying/lipopolysaccharide binding protein family. Researches have shown that both are not overlapped in physiological function, reduction of PLTP activity can decrease the secretion of VLDL, while reduction of CETP activity can elevate HDL cholesterol level, these two aspects are favorable for the prophylaxis and treatment of atherosclerosis. Consequently, Jiang et al. has advanced that PLTP and CETP dual inhibitor is a hopeful target for treating atherosclerosis (Jiang X. C., Tall A. R. PCT Int. Appl. WO 2002068450; Jiang X. C., Zhou H. W. Curr. Opin. Lipidol. 2006, 17, 302-308). N-{2-[2-(2,2-dimethyl-propanamido)-phenyldithio]-phenyl}-2,2-dimethyl-propanamide is the only one PLTP inhibitor that has been reported in literatures at present, and is PLTP and CETP dual inhibitor, the Ki values to inhibit both are 15 μM and 13 μM, respectively (WO 2002068450).

Researches have shown that PLTP selective inhibitor, PLTP and CETP dual inhibitor and CETP selective inhibitor can all be used for the treatment and/or prevention of various diseases associated with the increased plasma PLTP activity in a mammal (including human), such as atherosclerosis, peripheral vascular diseases, dyslipidemia, hyperlipemia, hypercholesterolemia, hypertriglyceridemia, familial hypercholesterolemia, cardiovascular diseases, angina pectoris, ischemia, heart ischemia, stroke, myocardial infarction, reperfusion injury, hypertension, diabetes with vascular complications, obesity or endotoxemia, etc.

Term "PLTP selective inhibitor" means a compound capable of inhibiting PLTP activity but having no inhibition action to CETP activity.

Term "PLTP and CETP dual inhibitor" means a compound capable of inhibiting both PLTP activity and CETP activity.

Term "CETP selective inhibitor" means a compound capable of inhibiting CETP activity but having no inhibition action to PLTP activity.

SUMMARY OF THE INVENTION

The object of the present invention is to seek and develop phospholipids transfer protein inhibitors and/or cholesteryl ester transfer protein inhibitors, regulate the metabolism of relevant lipoproteins by inhibiting the activity of phospholipids transfer protein and/or the activity of cholesteryl ester transfer protein to treat and prevent diseases associated with the rise of plasma phospholipids transfer protein activity and/or the rise of plasma cholesteryl ester transfer protein activity.

The present inventors have discovered via study that a compound represented by following formula (I) exhibits the activity to inhibit phospholipids transfer protein and/or cholesteryl ester transfer protein, so as to reduce the secretion of liver VLDL and/or raise the level of HDL cholesterol, and thus can be used for treating and preventing various diseases associated with the rise of phospholipids transfer protein activity and/or the rise of plasma cholesteryl ester transfer protein activity, thereby the present invention is accomplished.

Therefore, in one aspect, the present invention relates to a compound of formula (I),

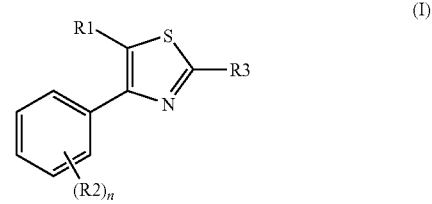

wherein:
R1 is phenyl-$C_1$-$C_6$alkyl, $C_1$-$C_{22}$alkyl, $C_3$-$C_{10}$cycloalkyl-$C_1$-$C_6$alkyl or $C_3$-$C_{10}$cycloalkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, O—($C_1$-$C_4$)-alkyl, oxo, amino, NH—($C_1$-$C_4$)-alkyl or N—[($C_1$-$C_6$)-alkyl]$_2$, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R3 is selected from the groups having following structures:

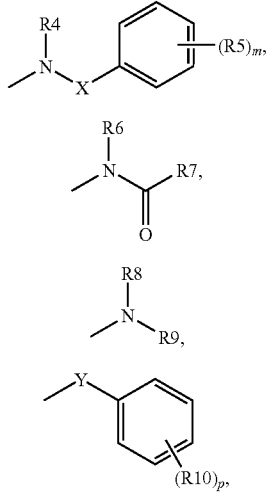

wherein,

R4 is hydrogen, $C_1$-$C_6$alkyl, alkylacyl, benzoyl or phenylsulfonyl; wherein the phenyl in benzoyl and phenylsulfonyl is optionally substituted with one or two substituents independently selected from hydroxyl, halogen, nitro, amino, cyano, $C_1$-$C_6$alkyl, $C_1$-$C_6$alkoxy and $C_{1-6}$haloalkyl;

each R5 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

R6 is hydrogen, $C_1$-$C_6$alkyl, alkylacyl, benzoyl or phenylsulfonyl group; wherein the phenyl in benzoyl and phenylsulfonyl is optionally substituted with one or two substituents independently selected from hydroxyl, halogen, nitro, amino, cyano, $C_1$-$C_6$alkyl, $C_1$-$C_6$alkoxy and $C_{1-6}$haloalkyl;

R7 is $C_1$-$C_6$alkyl, phenyl-$C_1$-$C_6$alkyl, wherein phenyl is optionally substituted with one, two or three hydroxyl, $C_1$-$C_6$alkyl, $C_1$-$C_6$alkoxy, $C_{1-6}$haloalkyl, amino, halogen, nitro, cyano, alkylacyl; and wherein alkyl may be substituted with hydroxyl, O—($C_1$-$C_4$)-alkyl, oxo, amino, NH—($C_1$-$C_4$)-alkyl or N—[($C_1$-$C_6$)-alkyl]$_2$, or optionally spaced with —O—, —S—, —NH—, —COO—, —CONH—;

R8 and R9 are independently selected from hydrogen; $C_1$-$C_{22}$ alkyl optionally substituted with hydroxyl, amino, carboxyl, $C_1$-$C_6$alkyl, $C_1$-$C_6$alkoxy and oxy and optionally spaced with —O—, —S— and —NH—, —COO—, —CONH—; phenyl-$C_1$-$C_6$alkyl, wherein phenyl is optionally substituted with one, two or three hydroxyl, $C_1$-$C_6$alkyl, $C_1$-$C_6$alkoxy, $C_{1-6}$haloalkyl, amino, halogen, nitro, cyano or alkylacyl; or R8 and R9, together with the nitrogen atom to which they are attached, form pyrrole, one five- or six-membered heterocycle, the heterocycle may contain additional one or two heteroatoms independently selected from N, O and S, and may form a fused heterocycle with phenyl ring, said heterocycle is, e.g., morpholine, piperazine, piperidine, pyrrole, imidazolidine, thiazolidine, oxazolidine, indole or indoline, said heterocycle may be optionally substituted with hydroxyl, $C_1$-$C_6$alkyl, $C_1$-$C_6$alkoxy, $C_{1-6}$haloalkyl, amino, halogen, nitro or cyano;

each R10 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

X is —(C=O)— or —(SO$_2$)—;

Y is $C_1$-$C_{10}$alkylene, $C_1$-$C_{10}$alkenylene or $C_1$-$C_{10}$alkynylene; said alkylene, alkenylene and alkynylene are optionally substituted with hydroxyl, amino, oxo, carboxyl, $C_1$-$C_6$alkyl, $C_1$-$C_6$alkoxy or optionally spaced with —O—, —S—, —NH—, —COO—, —CONH—;

n is 0, 1, 2, 3 or 4;

m is 0, 1, 2, 3 or 4;

p is 0, 1, 2, 3, or 4, or all possible isomers, prodrugs, pharmaceutically acceptable salts, solvates or hydrates thereof.

In another aspect, the present invention relates to a process for the preparation of a compound of formula (I).

In another aspect, the present invention relates to a pharmaceutical composition comprising a compound of formula (I) according to the present invention or all possible isomers, prodrugs, pharmaceutically acceptable salts, solvates or hydrates thereof as well as at least one pharmaceutically acceptable carrier.

In a further aspect, the present invention relates to use of a compound of formula (I) for the preparation of a medicament for the treatment and/or prevention of diseases associated with the increased plasma PLTP activity and/or the increased plasma CETP activity in a mammal, said diseases include but are not limited to: atherosclerosis, peripheral vascular diseases, dyslipidemia, hyperlipemia, hypercholesterolemia, hypertriglyceridemia, familial hypercholesterolemia, cardiovascular diseases, angina pectoris, ischemia, heart ischemia, stroke, myocardial infarction, reperfusion injury, hypertension, diabetes with vascular complications, obesity or endotoxemia, etc.

The term "$C_1$-$C_6$ alkyl" used herein means, no matter itself or as one part of other larger groups such as $C_1$-$C_6$ alkoxy, linear chain or branched chain atomic groups containing 1-6 carbon atoms, including but not limited to methyl, ethyl, n-propyl, isopropyl, n-butyl, sec-butyl, isobutyl and tert-butyl, etc.

The term "$C_1$-$C_6$-alkoxy" used herein means "$C_1$-$C_6$-alkyl-O—", the examples of alkoxy include but are not limited to methoxy, ethoxy, isopropoxy, etc.

The term "$C_1$-$C_6$-haloalkyl" used herein means $C_1$-$C_6$alkyl in which one or more hydrogen is substituted by halogen atom, herein trifluoromethyl (—CF$_3$) should be mentioned especially.

The term "halogen (halo-)" used herein means fluorine (fluoro-), chlorine (chloro-), bromine (bromo-) or iodine (iodo-).

The term "aryl" used herein means a 5-14-membered substituted or unsubstituted aromatic cyclic system, or an aromatic cyclic system possibly containing fused bicycles or tricycles, including but not limited to phenyl and naphthyl.

The following compounds are included in the formula (I) of the present invention:

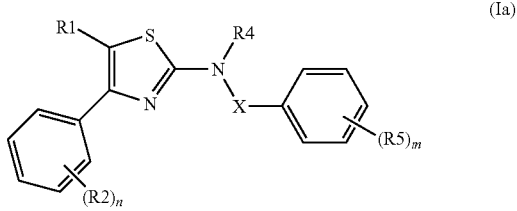

(Ia)

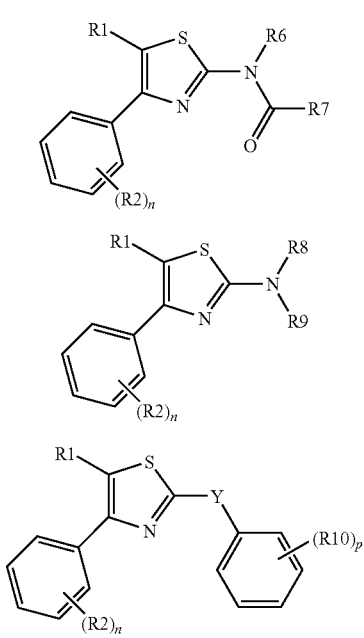

wherein R1-R10, X, Y, n, m, p are defined as above.

In one preferred embodiment of the present invention, said compounds are the compounds of formula (Ia):

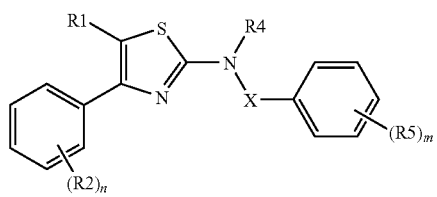

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R4 is hydrogen, benzoyl or phenylsulfonyl; wherein the phenyl in benzoyl and phenylsulfonyl is optionally substituted with one or two substituents independently selected from hydroxyl, halogen, nitro, amino, cyano, $C_1$-$C_6$alkyl, $C_1$-$C_6$alkoxy and $C_{1-6}$haloalkyl;

each R5 is independently selected from hydrogen, hydroxyl, $C_1$-$C_6$alkoxy, $C_{1-6}$haloalkyl, amino, halogen, nitro, cyano and alkylacyl;

X is —(C═O)—;

n is 0, 1, 2 or 3;

m is 0, 1, 2, 3 or 4.

In another preferred embodiment of the present invention, said compounds are the compounds of formula (Ib):

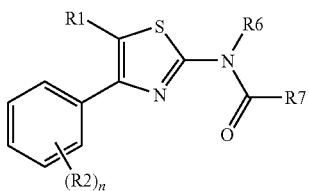

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R6 is hydrogen or $C_1$-$C_6$alkyl;

R7 is $C_1$-$C_6$alkyl, phenyl-$C_1$-$C_6$alkyl, wherein phenyl is optionally substituted with one, two or three hydroxyl, $C_1$-$C_6$alkyl, $C_1$-$C_6$alkoxy, $C_{1-6}$haloalkyl, amino, halogen, nitro, cyano, alkylacyl; and wherein alkyl may be substituted with hydroxyl, O—($C_1$-$C_4$)-alkyl, oxo, amino, NH—($C_1$-$C_4$)-alkyl or N—[($C_1$-$C_6$)-alkyl]$_2$, or optionally spaced with —O—, —S—, —NH—, —COO—, —CONH—;

n is 0, 1, 2 or 3.

In another preferred embodiment of the present invention, said compounds are the compounds of formula (Ic):

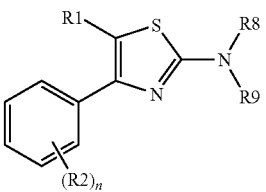

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R8 and R9 are independently selected from hydrogen; $C_1$-$C_{22}$ alkyl optionally substituted with hydroxyl, amino, carboxyl, $C_1$-$C_6$alkyl, $C_1$-$C_6$alkoxy or oxo and optionally spaced with —O—, —S— and —NH—, —COO—, —CONH—; or R8 and R9, together with the nitrogen atom to which they are attached, form pyrrole, one five- or six-membered heterocycle, the heterocycle may contain additional one or two heteroatoms independently selected from N, O and S, and may form a fused heterocycle with phenyl ring, said heterocycle is, e.g., morpholine, piperazine, piperidine, pyrrole, imidazolidine, thiazolidine, oxazolidine, indole or indoline, said heterocycle may be optionally substituted with hydroxyl, $C_1$-$C_6$alkyl, $C_1$-$C_6$alkoxy, $C_{1-6}$haloalkyl, amino, halogen, nitro or cyano;

n is 0, 1, 2 or 3.

In another preferred embodiment of the present invention, said compounds are the compounds of formula (Id):

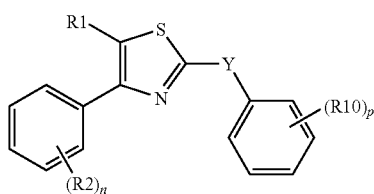

(Id)

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

each R10 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

Y is $C_1$-$C_{10}$alkylene, $C_1$-$C_{10}$alkenylene or $C_1$-$C_{10}$alkynylene; said alkylene, alkenylene and alkynylene are optionally substituted with hydroxyl, amino, oxo, carboxyl, $C_1$-$C_6$alkyl, $C_1$-$C_6$alkoxy or optionally spaced with —O—, —S—, —NH—, —COO—, —CONH—;

n is 0, 1, 2 or 3;

p is 0, 1, 2 or 3.

In one more preferred embodiment of the present invention, said compounds are the compounds of formula (Iaa):

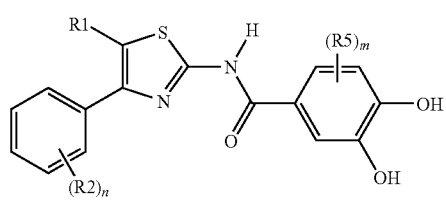

(Iaa)

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one or two substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

each R5 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

n is 0, 1 or 2;

m is 0, 1 or 2.

In one more preferred embodiment of the present invention, said compounds are the compounds of formula (Iba):

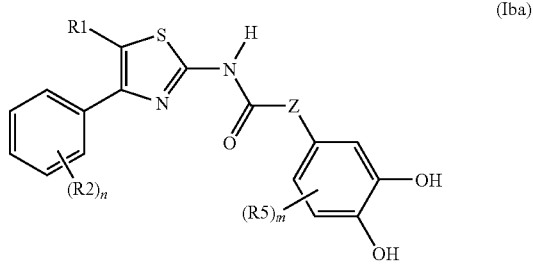

(Iba)

wherein,

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one or two substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

each R5 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

Z is $C_1$-$C_{10}$alkylene; said alkylene is optionally substituted with hydroxyl, amino, carboxyl, $C_1$-$C_6$alkyl or $C_1$-$C_6$alkoxy or optionally spaced with —O—, —S—, —NH—, —COO—, —CONH—;

n is 0, 1 or 2;

m is 0, 1 or 2.

In one more preferred embodiment of the present invention, said compounds are the compounds of formula (Ic), wherein R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one or two substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R8 and R9 are independently selected from hydrogen; $C_1$-$C_{22}$ alkyl optionally substituted with hydroxyl, amino, carboxyl, $C_1$-$C_6$alkyl, $C_1$-$C_6$alkoxy or oxo and optionally spaced with —O—, —S— and —NH—, —COO—, —CONH—; or R8 and R9, together with the nitrogen atom to which they are attached, form pyrrole, one five- or six-membered heterocycle, the heterocycle may contain additional one or two heteroatoms independently selected from N, O and S, and may form a fused heterocycle with phenyl ring, said heterocycle is, e.g., morpholine, piperazine, piperidine, pyrrole, imidazolidine, thiazolidine, oxazolidine, indole or indoline, said heterocycle may be optionally substituted with hydroxyl, $C_1$-$C_6$alkyl, $C_1$-$C_6$alkoxy, $C_{1-6}$haloalkyl, amino, halogen, nitro or cyano;

n is 0, 1 or 2.

In one more preferred embodiment of the present invention, said compounds are the compounds of formula (Ida):

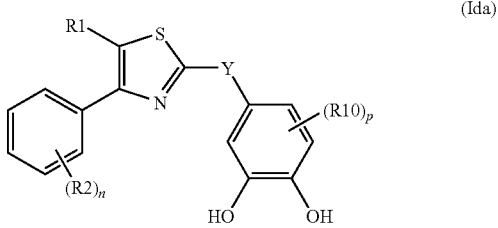

(Ida)

wherein

R1 is phenyl-$C_1$-$C_6$alkyl, $C_1$-$C_{22}$alkyl or $C_3$-$C_{10}$cycloalkyl-$C_1$-$C_6$alkyl, wherein phenyl is unsubstituted or substituted with one or two substituents independently selected from halogen, nitro, hydroxyl, amino, cyano, $C_1$-$C_6$alkyl, $C_1$-$C_6$alkoxy and $C_{1-6}$haloalkyl; and wherein alkyl and cycloalkyl may be optionally substituted with hydroxyl, oxo or amino, or optionally spaced with —O—, —S—, —NH—, —COO—, —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

each R10 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

Y is $C_1$-$C_{10}$alkylene, $C_1$-$C_{10}$alkenylene or $C_1$-$C_{10}$alkynylene; said alkylene, alkenylene and alkynylene are optionally substituted with hydroxyl, amino, oxo, carboxyl, $C_1$-$C_6$alkyl or $C_1$-$C_6$alkoxy, or optionally spaced with —O—, —S—, —NH—, —COO—, —CONH—;

n is 0, 1 or 2;

p is 0, 1 or 2.

The compounds of formula (Ia) are more preferably selected from:
(1) 5-benzyl-4-(4-methoxy-phenyl)-thiazol-2-ylamine;
(2) 5-benzyl-4-(4-hydroxy-phenyl)-thiazol-2-ylamine;
(3) N-[5-benzyl-4-(4-methoxy-phenyl)-thiazol-2-yl]-benzamide;
(4) N-[5-benzyl-4-(4-methoxy-phenyl)-thiazol-2-yl]-4-fluoro-benzamide;
(5) N-[5-benzyl-4-(4-methoxy-phenyl)-thiazol-2-yl]-4-chloro-benzamide;
(6) 4-(4-methoxy-phenyl)-5-(4-nitro-benzyl)-thiazol-2-ylamine;
(7) N-[5-benzyl-4-(4-hydroxy-phenyl)-thiazol-2-yl]-4-fluoro-benzamide;
(8) N-[5-benzyl-4-(4-hydroxy-phenyl)-thiazol-2-yl]-4-chloro-benzamide;
(9) 4-(4-fluoro-phenyl)-5-(4-nitro-benzyl)-thiazol-2-ylamine;
(10) 4-fluoro-N-[4-(4-methoxy-phenyl)-5-(4-nitro-benzyl)-thiazol-2-yl]-benzamide;
(11) 4-fluoro-N-[4-(4-fluoro-phenyl)-5-(4-nitro-benzyl)-thiazol-2-yl]-benzamide;
(12) N-[5-benzyl-4-(4-methoxy-phenyl)-thiazol-2-yl]-3,4-dimethoxy-benzamide;
(13) N-[5-benzyl-4-(4-methoxy-phenyl)-thiazol-2-yl]-4-cyano-benzamide;
(14) 4-cyano-N-[4-(4-methoxy-phenyl)-5-(4-nitro-benzyl)-thiazol-2-yl]-benzamide;
(15) 4-cyano-N-[4-(4-fluoro-phenyl)-5-(4-nitro-benzyl)-thiazol-2-yl]-benzamide;
(16) N-(5-benzyl-4-(4-methoxy-phenyl)-thiazol-2-yl]-3,5-difluoro-benzamide;
(17) 3,5-difluoro-N-[4-(4-methoxy-phenyl)-5-(4-nitro-benzyl)-thiazol-2-yl]-benzamide;
(18) 3,5-difluoro-N-[4-(4-fluoro-phenyl)-5-(4-nitro-benzyl)-thiazol-2-yl]-benzamide;
(19) N-[5-benzyl-4-(4-hydroxyl-phenyl)-thiazol-2-yl]-3,4-dihydroxyl-benzamide;
(20) N-[4-(4-fluoro-phenyl)-5-(4-nitro-benzyl)-thiazol-2-yl]-3,4-dimethoxy-benzamide;
(21) 5-(4-fluoro-benzyl)-4-(4-methoxy-phenyl)-thiazol-2-ylamine;
(22) 3,5-difluoro-N-[5-(4-fluoro-benzyl)-4-(4-methoxy-phenyl)-thiazol-2-yl]-benzamide;
(23) 4-fluoro-N-[5-(4-fluoro-benzyl)-4-(4-methoxy-phenyl)-thiazol-2-yl]-benzamide;
(24) N-[5-(4-fluoro-benzyl)-4-(4-methoxy-phenyl)-thiazol-2-yl]-N-(3,4-dimethoxy-benzamido)-3,4-dimethoxy-benzamide;
(25) 4-cyano-N-[5-(4-fluoro-benzyl)-4-(4-methoxy-phenyl)-thiazol-2-yl]-benzamide;
(26) 5-(4-nitro-benzyl)-4-phenyl-thiazol-2-ylamine;
(27) N-[5-benzyl-4-(4-methoxy-phenyl)-thiazol-2-yl]-4-methoxy-benzamide;
(28) 3,4-dimethoxy-N-[4-(4-methoxy-phenyl)-5-(4-nitro-benzyl)-thiazol-2-yl]-benzamide;
(29) 3,4-dimethoxy-N-[5-(4-nitro-benzyl)-4-phenyl-thiazol-2-yl]-benzamide;
(30) N-[5-(4-fluoro-benzyl)-4-(4-methoxy-phenyl)-thiazol-2-yl]-3,4-dimethoxy-benzamide;
(31) N-[4-(4-fluoro-phenyl)-5-(4-nitro-benzyl)-thiazol-2-yl]-3,4-dihydroxy-benzamide;
(32) 3,4-dihydroxy-N-[5-(4-nitro-benzyl)-4-phenyl-thiazol-2-yl]-benzamide;
(33) N-[5-(4-fluoro-benzyl)-4-(4-hydroxy-phenyl)-thiazol-2-yl]-3,4-dihydroxy-benzamide;
(34) 3,4-dihydroxy-N-[4-(4-hydroxy-phenyl)-5-(4-nitro-benzyl)-thiazol-2-yl]-benzamide;
(35) N-[5-benzyl-4-(4-methoxy-phenyl)-thiazol-2-yl]-2,4-dimethoxy-benzamide;
(36) N-[5-benzyl-4-(4-methoxy-phenyl)-thiazol-2-yl]-2-methoxy-benzamide;
(37) N-[5-benzyl-4-(4-methoxy-phenyl)-thiazol-2-yl]-3,4,5-trimethoxy-benzamide;
(38) N-[5-benzyl-4-(4-hydroxy-phenyl)-thiazol-2-yl]-2,4-dihydroxy-benzamide;
(39) N-[5-benzyl-4-(4-hydroxy-phenyl)-thiazol-2-yl]-2-hydroxy-benzamide;
(40) N-[5-benzyl-4-(4-hydroxy-phenyl)-thiazol-2-yl]-4-methoxy-benzamide;
(41) N-[5-benzyl-4-(4-hydroxy-phenyl)-thiazol-2-yl]-3,4,5-trihydroxy-benzamide;
(42) N-[5-benzyl-4-(4-methoxy-phenyl)-thiazol-2-yl]-3-methoxy-benzamide;
(43) N-[5-benzyl-4-(4-methoxy-phenyl)-thiazol-2-yl]-3,5-dimethoxy-benzamide;
(44) N-[5-benzyl-4-(4-hydroxy-phenyl)-thiazol-2-yl]-3-hydroxy-benzamide;

(45) N-[5-benzyl-4-(4-hydroxy-phenyl)-thiazol-2-yl]-3,5-dihydroxy-benzamide;
(46) N-[5-benzyl-4-(4-hydroxy-phenyl)-thiazol-2-yl]-4-hydroxy-benzamide;
(47) 5-cyclohexylmethyl-4-(4-methoxy-phenyl)-thiazol-2-ylamine;
(48) N-[5-cyclohexylmethyl-4-(4-methoxy-phenyl)-thiazol-2-yl]-3,4-dimethoxy-benzamide;
(49) N-[5-cyclohexylmethyl-4-(4-hydroxy-phenyl)-thiazol-2-yl]-3,4-dihydroxy-benzamide;
(50) N-[5-cyclohexylmethyl-4-(4-hydroxy-phenyl)-thiazol-2-yl]-3,4,5-trimethoxy-benzamide;
(51) N-[5-cyclohexylmethyl-4-(4-hydroxy-phenyl)-thiazol-2-yl]-3,4,5-trihydroxy-benzamide;
(52) 4-(4-methoxy-phenyl)-5-methyl-thiazol-2-ylamine;
(53) 3,4,5-trimethoxy-N-[4-(4-methoxy-phenyl)-5-methyl-thiazol-2-yl]-benzamide;
(54) 3,4-dimethoxy-N-[4-(4-methoxy-phenyl)-5-methyl-thiazol-2-yl]-benzamide;
(55) 3,4,5-trihydroxy-N-[4-(4-hydroxy-phenyl)-5-methyl-thiazol-2-yl]-benzamide;
(56) 3,4-dihydroxy-N-[4-(4-hydroxy-phenyl)-5-methyl-thiazol-2-yl]-benzamide;
(57) 4-(4-methoxy-phenyl)-5-phenylethyl-thiazol-2-ylamine;
(58) 3,4-dimethoxy-N-[4-(4-methoxy-phenyl)-5-phenyl-ethyl-thiazol-2-yl]-benzamide;
(59) 3,4,5-trimethoxy-N-[4-(4-methoxy-phenyl)-5-phenyl-ethyl-thiazol-2-yl]-benzamide;
(60) 3,4-dihydroxy-N-[4-(4-hydroxy-phenyl)-5-phenyl-ethyl-thiazol-2-yl]-benzamide;
(61) 3,4,5-trihydroxy-N-[4-(4-hydroxy-phenyl)-5-phenyl-ethyl-thiazol-2-yl]-benzamide;
(62) 4-(4-methoxy-phenyl)-5-n-butyl-thiazol-2-ylamine;
(63) N-[5-n-butyl-4-(4-methoxy-phenyl)-thiazol-2-yl]-3,4-dimethoxy-benzamide;
(64) N-[5-n-butyl-4-(4-methoxy-phenyl)-thiazol-2-yl]-3,4,5-trimethoxy-benzamide;
(65) N-[5-n-butyl-4-(4-hydroxy-phenyl)-thiazol-2-yl]-3,4-dihydroxy-benzamide;
(66) N-[5-n-butyl-4-(4-hydroxy-phenyl)-thiazol-2-yl]-3,4,5-trihydroxy-benzamide; and
(67) N-[5-benzyl-4-(4-methoxy-phenyl)-thiazol-2-yl]-N-p-tolylsulfonyl-p-tolylsulfonamide;
or all possible isomers, prodrugs, pharmaceutically acceptable salts, solvates or hydrates thereof.

The compounds of formula (Ib) are more preferably selected from:
(68) N-[5-benzyl-4-(4-methoxy-phenyl)-thiazol-2-yl]-3-(3,4-dimethoxy-phenyl)-propanamide; and
(69) N-[5-benzyl-4-(4-hydroxy-phenyl)-thiazol-2-yl]-3-(3,4-dihydroxy-phenyl)-propanamide;
or all possible isomers, prodrugs, pharmaceutically acceptable salts, solvates or hydrates thereof.

The compounds of formula (Ic) are more preferably selected from:
(70) 4-[5-benzyl-4-(4-methoxy-phenyl)-thiazol-2-yl]-morpholine;
(71) 1-[5-benzyl-4-(4-methoxy-phenyl)-thiazol-2-yl]-piperazine;
(72) 1-[5-benzyl-4-(4-methoxy-phenyl)-thiazol-2-yl]-piperazine trihydrochloride;
(73) 2-[[5-benzyl-4-(4-methoxy-phenyl)-thiazol-2-yl]-(2-hydroxy-ethyl)-amino]-ethanol;
(74) 4-(5-benzyl-2-morpholin-4-yl-thiazol-4-yl)-phenol;
(75) 4-(5-benzyl-2-piperazin-4-yl-thiazol-4-yl)-phenol; and
(76) 4-(5-benzyl-2-[bis-(2-hydroxy-ethyl)-amino]-thiazol-4-yl)-phenol;
or all possible isomers, prodrugs, pharmaceutically acceptable salts, solvates or hydrates thereof.

The compounds of formula (Id) are more preferably selected from:
(77) 5-benzyl-2-[2-(3,4-dimethoxy-phenyl)-ethyl]-4-(4-methoxy-phenyl)-thiazole; and
(78) 4-{2-[5-benzyl-4-(4-hydroxy-phenyl)-thiazol-2-yl]-ethyl}-benzene-1,2-diol; or all possible isomers thereof, prodrugs thereof, pharmaceutically acceptable salts thereof, solvates thereof or hydrates thereof.

The present invention also relates to suitable pharmaceutically acceptable salts, solvates or hydrates of the compounds represented by the formula (I), wherein the pharmaceutically acceptable salts include but are not limited to the salts of the compounds of formula (I) formed with an inorganic acid such as hydrochloric acid, sulfuric acid, phosphoric acid, phosphorous acid, hydrobromic acid and nitric acid, as well as the salts formed with various organic acids, such as maleic acid, malic acid, fumaric acid, succinic acid, tartaric acid, citric acid, acetic acid, lactic acid, methanesulfonic acid, toluene-p-sulfonic acid, palmic acid, etc.

Some compounds of the present invention may be crystallized or recrystallized with water or various organic solvents. Under this circumstance, various solvates may be formed. In the present invention, the solvates in stechiometry are involved, including hydrates and the compounds containing variable water formed in the preparation by lyophylization.

The present invention further relates to various isomers of the compounds of formula (I). Part of the compounds of the present invention may be present in the form of optical isomers or tautomers, their all possible presence forms are involved in the present invention, especially the forms of pure isomers. Different forms of isomers can be isolated or resolved from other forms of isomers by various conventional means, or some an isomer can be obtained by various conventional synthetic processes or stereospecificity or asymmetric synthesis. Since the compounds of formula (I) serve the purpose of medical use, it can be understood that they had better be provided in pure forms thereof, e.g., at least 60% purity, preferably at least 75%, more preferably at least 85%, most preferably at least 98% (by weight) purity. The preparation methods of impure compounds can be used for the form of purer compounds in the pharmaceutical composition. Those impure products at least contain 1%, preferably at least 5%, more preferably at least 10% of the compounds represented by formula (I) or their pharmaceutically acceptable derivatives.

On the other hand, the present invention relates to a process for the synthesis of the compounds of formula (I). The compounds of formula (I) can be prepared by artificial synthesis process with known or commercially available compounds as raw materials. If the raw materials are not commercially available, their preparation processes are provided in the present invention, or they can be prepared by the processes reported in the literatures.

Particularly, the present invention provides a process for preparing the compounds of formula (I) or pharmaceutically acceptable salts thereof, solvates thereof or hydrates thereof. Following preparation processes are directed to sub-structures, respectively.

The preparation process of the compound of formula (Ia) is as follows:
(i) Substituted acetic acid of formula (II) is allowed to react with excessive dichlorosulfoxide at room temperature to reflux temperature to give acyl chloride of formula (III), the substituted acetic acid of formula (II) is commercially available or prepared by the process reported in the literatures,

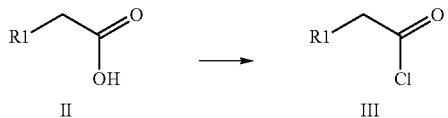

wherein, R1 is defined as above;

(ii) the acyl chloride of formula (III) is allowed to react with an arene of formula (IV) at a reaction temperature of −20° C. to 150° C. in a common solvent for friedel-crafts acylation, such as, dichloromethane, 1,2-dichloroethane, petroleum ether, nitrobenzene in the presence of a Lewis acid catalyst such as $AlCl_3$ to give a ketone of formula (V),

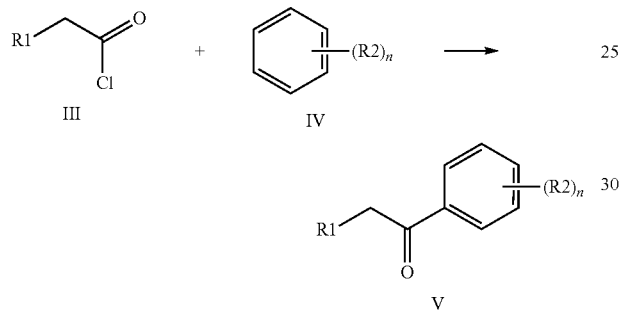

wherein, R1, R2 and n are defined as above;

(iii) the ketone of formula (V) is allowed to react with a bromide at a reaction temperature of 0° C. to 50° C. in an inert solvent such as trichloromethane or carbon tetrachloride in the presence of a Lewis acid catalyst such as $AlCl_3$ to obtain α-bromo-ketone of formula (VI),

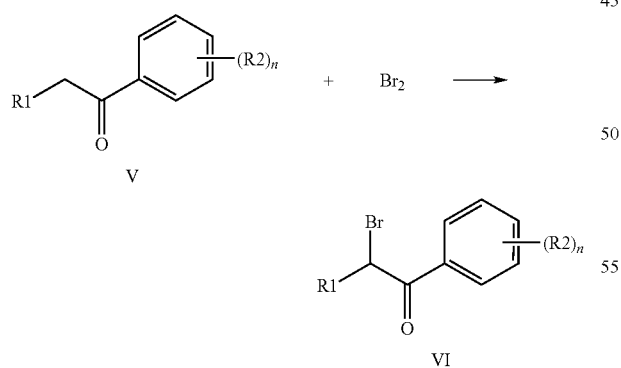

wherein, R1, R2 and n are defined as above;

(iv) the α-bromo-ketone of formula (VI) is allowed to react with thiourea at reflux temperature in a lower alcohol solvent such as ethanol in the presence of acid binding agent anhydrous sodium acetate to obtain 2-aminothiazole of formula VII,

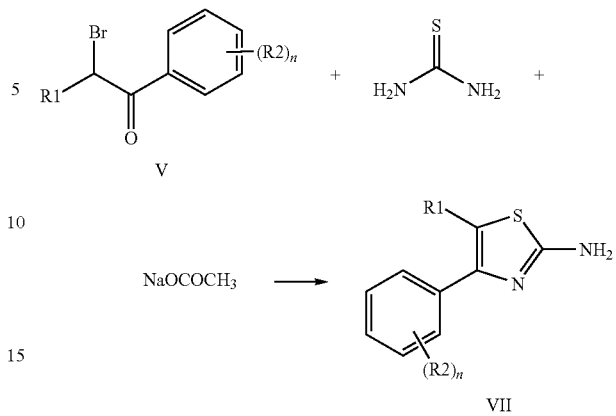

wherein, R1, R2 and n are defined as above;

(v) the 2-aminothiazole of formula VII is allowed to react with carboxylic acid halide (X=—CO—) or sulfonic acid halide (X=—$SO_2$—) of formula (VIII) (wherein A is Cl, Br or I) in an inert solvent such as tetrahydrofuran, ethyl acetate or dichloromethane, etc in the presence of a carbonyl activating agent such as N,N-dimethylaminopyridine and acid binding agent such as triethylamine to obtain a compound of formula (IX), wherein the compound VIII is prepared by reacting corresponding carboxylic acid or sulfonic acid with excessive $SOCl_2$,

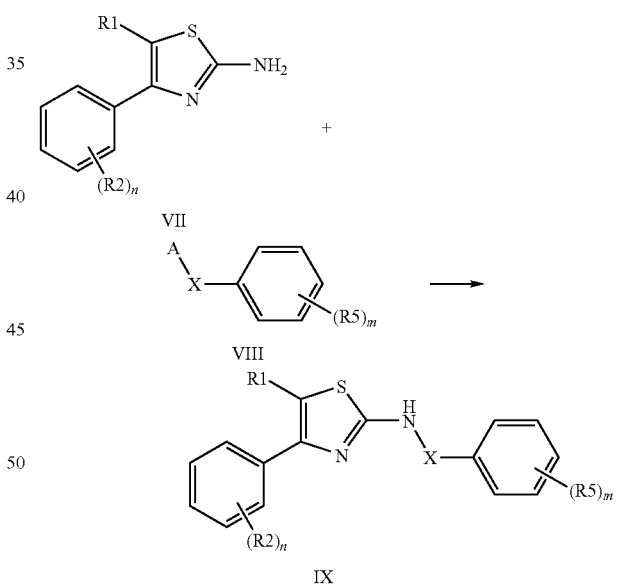

wherein, R1, R2, R5, X, n and m are defined as above;

(vi) in the step (v), when the compound VIII is excessive, the corresponding compounds substituted with diacyl or disulfonyl are isolated, and they can be also prepared with compound IX as raw material, in an inert solvent such as tetrahydrofuran, the compound IX is treated with a strong base such as sodium hydride or butyl lithium, etc., and the reacted with a halogenated compound or carboxylic acid halide R4-A (wherein A is Cl, Br or I) to obtain a compound of formula (Ia),

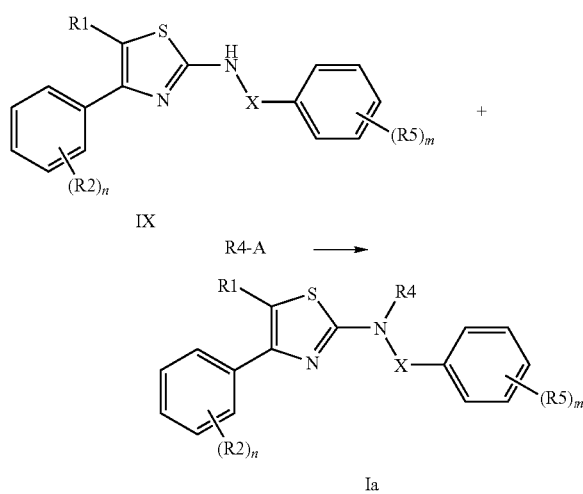

wherein, R1, R2, R4, R5, X, n and m are defined as above;
(vii) the substituents in the compounds of formula (Ia) are subjected to functional group conversion according to the processes known in the art, for example, for the compound in which methoxy is linked to the phenyl ring, they can be treated with boron tribromide at a temperature range of −78° C. to 50° C. in dichloromethane to remove methyl to obtain the corresponding hydroxyl compounds; for the compound in which multiple phenyl rings have methoxy group or phenyl ring has a plurality of methoxy groups, only the molar ratio of boron tribromide is correspondingly increased.

The preparation process of the compound of formula (Ib) is as follows:
(i) 2-aminothiazole of formula VII is allowed to react with carboxylic acid halide of formula (X) (wherein A is Cl, Br or I) in an inert solvent such as tetrahydrofuran, ethyl acetate or dichloromethane, etc. in the presence of a carbonyl activating agent such as N,N-dimethylamino-pyridine and a acid binding agent such as triethylamine to obtain a compound of formula (XI), wherein the compound X is prepared by reacting corresponding carboxylic acid with excessive $SOCl_2$,

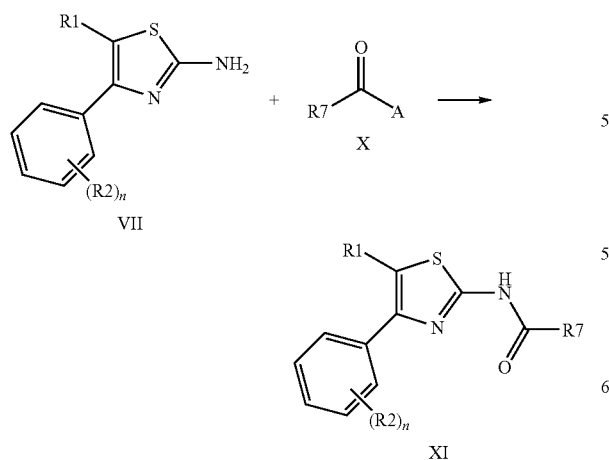

wherein, R1, R2, R7 and n are defined as above;
(ii) in the step (i), when the compound X is excessive, the corresponding compounds substituted with diacyl or disulfonyl are isolated, and they can be also prepared with compound XI as raw material, in an inert solvent such as tetrahydrofuran, the compound XI is treated with a strong base such as sodium hydride or butyl lithium, etc., and the reacted with a halogenated compound or carboxylic acid halide XII (wherein A is Cl, Br or I) to obtain a compound of formula (Ib),

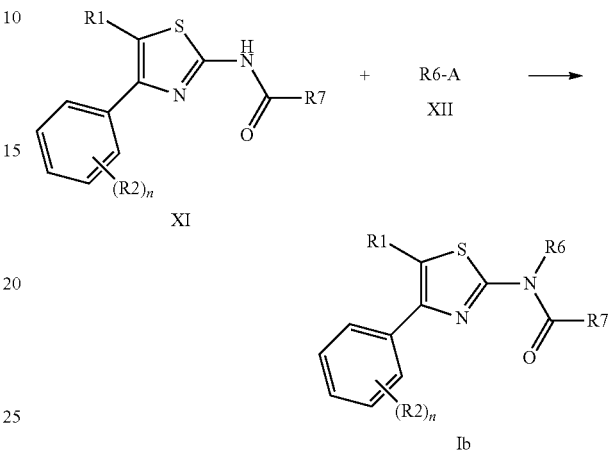

wherein, R1, R2, R6, R7 and n are defined as above;
(iii) the substituents in the compounds of formula (Ib) are subjected to functional group conversion according to the processes known in the art, for example, for the compound in which methoxy is linked to the phenyl ring, they can be treated with boron tribromide at a temperature range of −78° C. to 50° C. in dichloromethane to remove methyl to obtain the corresponding hydroxyl compounds; for the compound in which multiple phenyl rings have methoxy group or phenyl ring has a plurality of methoxy groups, only the molar ratio of boron tribromide is correspondingly increased.

The preparation process of the compound of formula (Ic) is as follows:
(i) 2-aminothiazole of formula VII is treated with iso-amyl nitrite and cupric chloride at a temperature range of 0° C. to 10° C. in an organic solvent such as acetonitrile to obtain a compound of formula (XIII),

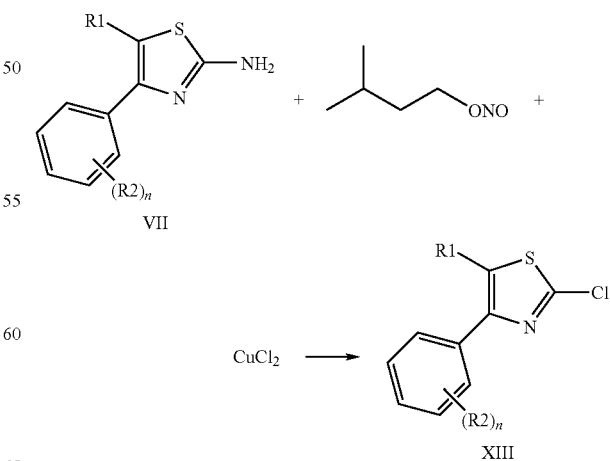

wherein, R1, R2 and n are defined as above;

(ii) the compound of formula (XIII) is treated with an amine of formula (XIV) or a nitrogen-containing heterocycle, lithium hydroxide monohydrate and potassium iodide at a temperature from 50° C. to 150° C. in an organic solvent such as N,N-dimethylformamide (DMF) to obtain a compound of formula (Ic),

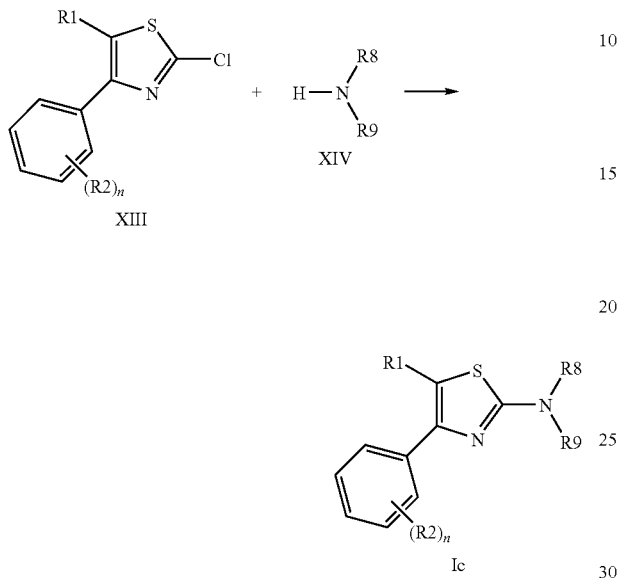

wherein, R1, R2, R8, R9 and n are defined as above;

(iii) the substituents in the compounds of formula (Ic) are subjected to functional group conversion according to the processes known in the art, for example, for the compound in which methoxy is linked to the phenyl ring, they can be treated with boron tribromide at a temperature of −78° C. to 50° C. in dichloromethane to remove methyl to obtain the corresponding hydroxyl compounds; for the compound in which multiple phenyl rings have methoxy group or phenyl ring has a plurality of methoxy groups, only the molar ratio of boron tribromide is correspondingly increased.

The preparation process of the compound of formula (Id) is as follows:

(i) Carboxylic acid of formula (XV) is allowed to react with excessive $SOCl_2$ at room temperature to reflux temperature to give acyl chloride of formula (XVI); or carboxylic acid of formula (XV) is allowed to react with equimolar isobutyl chlorocarbonate at a temperature range of −10° C. to 50° C. in an inert solvent such as tetrahydrofuran in the presence of acid binding agents such as triethylamine to obtain a mixture of acid anhydride of formula (XVII). The carboxylic acid of formula (XV) is commercially available or prepared by the process known by those skilled in the art,

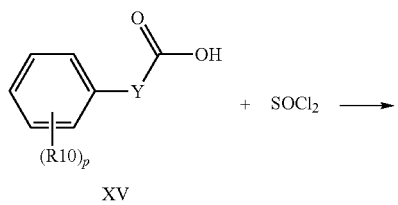

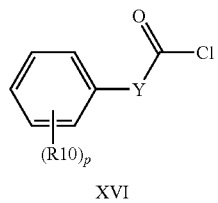

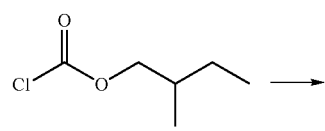

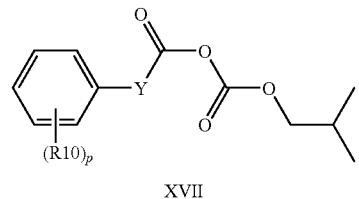

wherein, R10, Y and p are defined as above;

(ii) the acyl chloride of formula (XVI) or the mixture of acid anhydride of formula (XVII) is allowed to react with ammonia water or ammonia at a temperature range of −10° C. to 50° C. in an organic solvent such as tetrahydrofuran, methanol, ethanol, etc. to obtain an amide of formula (XVIII),

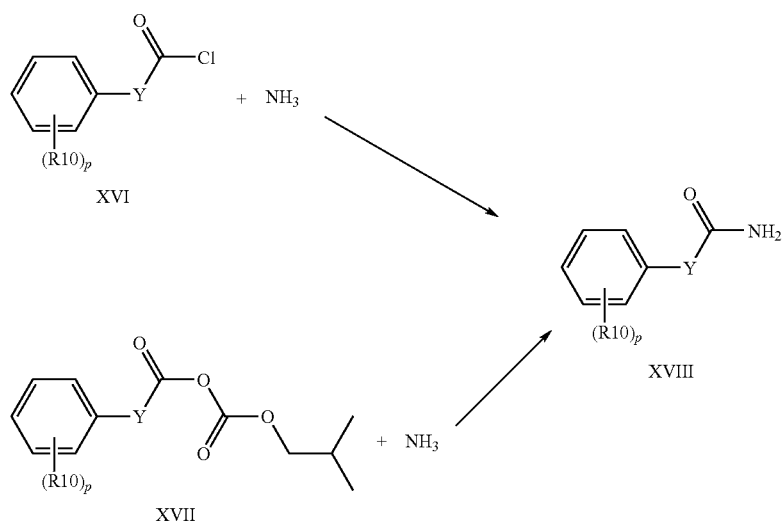

wherein, R10, Y and p are defined as above;

(iii) the amide of formula (XVIII) is allowed to react with P₂S₅ in an inert solvent such as tetrahydrofuran to obtain thioamide of formula (XIX),

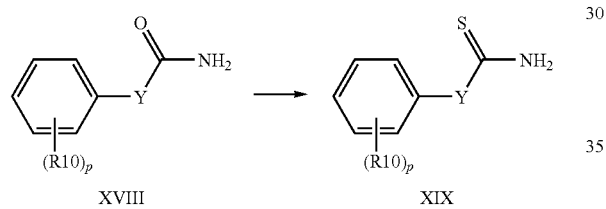

wherein, R10, Y and p are defined as above;

(iv) the thioamide of formula (XIX) is allowed to react with α-bromo-ketone of formula (VI) at reflux temperature in a lower alcohol solvent such as ethanol in the presence of acid binding agent anhydrous sodium acetate to obtain thiazole of formula (Id),

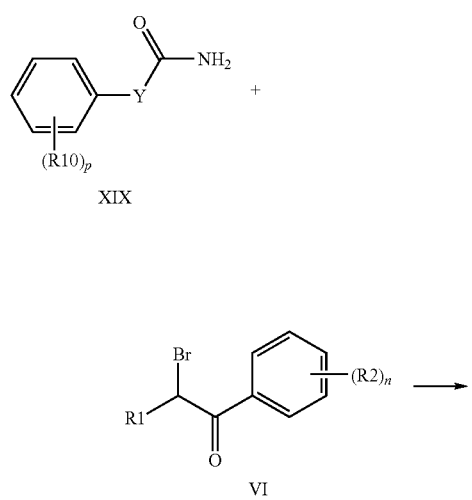

-continued

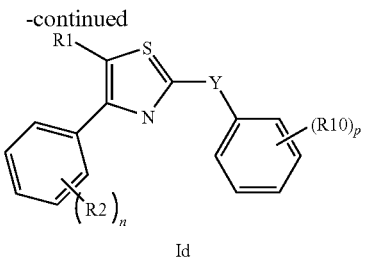

wherein, R1, R2, R10, Y, n and p are defined as above;

(v) the substituents in the compounds of formula (Id) are subjected to functional group conversion according to the processes known in the art, for example, for the compound in which methoxy is linked to the phenyl ring, they can be treated with boron tribromide at a temperature range of −78° C. to 50° C. in dichloromethane to remove methyl to obtain the corresponding hydroxyl compounds; for the compound in which multiple phenyl rings have methoxy group or phenyl ring has a plurality of methoxy groups, only the molar ratio of boron tribromide is correspondingly increased.

The compound of formula (I) can be synthesized individually by a conventional process, or synthesized in a library unit (each library contains at least two, or 5-1000, preferably 10-100 compounds) by mix and split process of combination chemistry or parallel synthesis process, i.e., it can be synthesized in liquid phase or by solid phase synthesis process.

The detailed data of the preparation of the compound of formula (I) are provided in the examples.

Further, the present invention relates to use of a compound of formula (I), or all possible isomers, prodrugs, pharmaceutically acceptable salts, solvates or hydrates thereof for the production of a medicament for the treatment and/or prevention of diseases associated with the increased plasma PLTP activity and/or the increased plasma CETP activity in a mammal, said diseases include but are not limited to: atherosclerosis, peripheral vascular diseases, dyslipidemia, hyperlipemia, hypercholesterolemia, hypertriglyceridemia, familial hypercholesterolemia, cardiovascular diseases, angina pectoris, ischemia, heart ischemia, stroke, myocardial infarction, reperfusion injury, hypertension, diabetes with vascular complications, obesity or endotoxemia.

The present invention also relates to a method for the treatment of diseases associated with the increased plasma PLTP activity and/or the increased plasma CETP activity in a mammal, comprising administering by a suitable manner an effective amount of a compound of formula (I) or all possible isomers, prodrugs, pharmaceutically acceptable salts, solvates or hydrates thereof to mammal in need of such treatment. The present invention further discloses a method to administer mammal in need of treatment, and an effective amount of the compound of formula (I) or its suitable pharmaceutically acceptable salts or hydrates.

Further, the present invention relates to use of a compound of formula (I), or all possible isomers, prodrugs, pharmaceutically acceptable salts, solvates or hydrates thereof for the production of a medicament capable of inhibiting the activity of plasma PLTP and/or the activity of plasma CETP in mammal.

The present invention also relates to a method of inhibiting the activity of plasma PLTP and/or the activity of plasma CETP in mammal, comprising administering by a suitable manner an effective amount of a compound of formula (I) or all possible isomers, prodrugs, pharmaceutically acceptable salts, solvates or hydrates thereof to mammal in need of inhibiting the activity of plasma PLTP and/or the activity of plasma CETP.

Furthermore, the compound of formula (I) according to the present invention or its pharmaceutically acceptable salts can be used separately or in the form of a pharmaceutical composition together with a pharmaceutically acceptable carrier or excipient. When used in the form of a pharmaceutical composition, it is usually to combine an effective amount of the compound of formula (I) according to the present invention or its pharmaceutically acceptable salts or hydrates and one or more pharmaceutically acceptable carriers or diluents to form a suitable administration form or dosage form. This procedure includes mixing ingredients, granulating, compressing or dissolving through a suitable manner. Therefore, the present invention provides a pharmaceutical composition comprising a compound of formula (I), all possible isomers, prodrugs, pharmaceutically acceptable salts, solvates or hydrates thereof as well as at least one pharmaceutically acceptable salt.

The pharmaceutical composition comprising the compound of the present invention can be administered by any one of following routes: oral, spray inhalation, rectal, nasal cavity, vaginal, topical, parenteral, such as subcutaneous, intravenous, intramuscular, intraperitoneally, intrathecal, intraventricular, intrasternal or intracal injection or importation, or administered by means of an explanted reservoir, preferably oral administration, intramuscular injection, intraperitoneal or intravenous administration.

The compound of the present invention or a pharmaceutical composition comprising the same can be administered in unit dose form. Administration dosage form can be a liquid or solid dosage form. Liquid dosage form can be true solutions, colloids, particulates, emulsions, suspensions. Other dosage forms include, e.g., tables, capsules, drop pills, aerosols, pills, powders, solutions, suspensions, emulsions, particulates, suppositories, lyophilized powders, clathrates, embeddings, patches, embrocations, and so on.

The pharmaceutical composition of the present invention further comprises conventional carriers, herein the pharmaceutically acceptable carriers include but are not limited to: an ion exchanger, alumina, aluminium stearate, lecithin, serum protein such as human serum protein, a buffer such as phosphate, glycerol, sorbic acid, potassium sorbate, partial glycerolipid mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinylpyrrolidone, cellulose materials, polyglycol, carboxylmethylcellulose sodium, polyacrylate, beeswax, lanolin, etc. The content of carrier in the pharmaceutical composition can be 1% to 98% by weight, generally about 80% by weight. For convenience, topical anesthetic, preservative and buffer, etc. can be directly dissolved in the carrier.

Oral tablets and capsules can contain excipients, such as binders, e.g., syrup, gum arabic, sorbitol, bassora gum, or polyvinyl pyrrolidone, fillers, e.g., lactose, sucrose, corn starch, calcium phosphate, sorbitol, aminoacetic acid, lubricants, e.g., magnesium stearate, talc, polyglycol, silica, disintegrants, e.g., potato starch, or pharmaceutically acceptable wetting agents, such as sodium lauryl sulfate. The tablets can be coated by the methods known in the field of pharmaceutics.

Oral liquids can be prepared into suspensions of water and oil, solutions, emulsions, syrups or elixirs, and can also be prepared into dried products, which are supplied with water or other suitable vehicle before use. This liquid preparation can contain routine additives, such as a suspending agent, sorbitol, cellulose methyl ether, glucose syrup, gel, hydroxyethylcellulose, carboxylmethylcellulose, aluminum stearate gel, hydrogenated edible fats, emulsifiers, such as lecithin, Span-80, arabic gum; or non-aqueous carriers (which may contain edible oils), such as almond oil, fats, such as glycerol, ethylene glycol, or ethanol; preservatives, such as methyl p-hydroxybenzoate or propyl p-hydroxybenzoate, sorbic acid. If required, flavoring agents or coloring agents can be added.

Suppositories can contain routine suppository matrix, such as cocoa butter or other glycerides.

For parenteral administration, liquid dosage forms are usually formulated with a compound and a sterile carrier. The carrier is principally selected from water. According to the difference of the carrier selected and the concentration of pharmaceutical, the compound can be dissolved in the carrier and prepared into a suspension. When an injection solution is prepared, the compound is dissolved in water, then filtrated, disinfected and packed into seal bottle or ampoule.

When it is administrated topically to the skin, the compound of the present invention can be prepared into a suitable form of ointment, lotion, or cream, in which the active ingredient is suspended or dissolved in one or more carriers. The carrier for use in ointment preparation includes but is not limited to: mineral oil, liquid paraffin, white paraffin, propanediol, polyethylene oxide, polyoxytrimethylene, emulsifying wax and water; the carrier for use in lotion and cream includes but is not limited to: mineral oil, sorbitan monostearate, Tween-60, cetearyl ester wax, hexadecylene aromatic alcohol, 2-octyldodecanol, benzyl alcohol and water.

According to different administration manners, the composition can comprises active ingredients at a weight ratio of 0.1%, or preferably of 10-60%. However, when the composition contains unit dosage, each unit dosage preferably contains 50-500 mg of active ingredients. According to the difference in administration route and administration frequency, a suitable therapeutic dosage for adult is 100-3000 mg per day, for example, 1500 mg per day. This dosage corresponds to 1.5-50 mg/kg/day, the suitable dosage is 5-20 mg/kg/day.

It should be recognized that the optimal administration dosage and interval of the compound of formula (I) depend on the property of the compound and external conditions such as administration form, route and position as well as special mammal animals to be treated, whereas this optimal administration dosage can be determined by conventional techniques. At the same time, it should be also recognized that optimal course of treatment, namely, the dosage per day of the compound of formula (I) in a specified time, can be determined by a method well known in the art.

CONCRETE MODES FOR CARRYING OUT THE INVENTION

Following specific examples are preferred embodiments of the present invention, which should not be understood to form a restriction to the present invention in any way.

The melting point of compounds was determined by RY-1 melting point apparatus, and the thermometer was not revised. The mass spectrum of compounds was determined by Micromass ZabSpec high resolution mass spectrometer (a resolution of 1000). The $^1$H-NMR of compounds was determined by means of JNM-ECA-400 superconductive NMR instrument, operation frequency $^1$H-NMR 400 MHz.

Example 1

Preparation of 5-benzyl-4-(4-methoxy-phenyl)-thiazol-2-ylamine

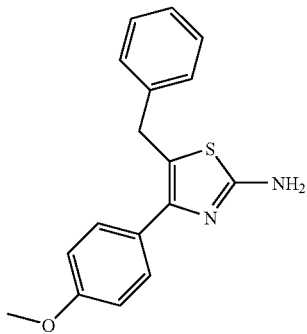

Step 1: Preparation of 3-phenylpropionyl chloride

To a 100 ml eggplant-shaped flask were added 20.0 g (133.2 mmol) 3-phenylpropionic acid and 24.5 g (205.9 mmol) thionyl chloride, a reflux condenser pipe carrying a calcium chloride drying pipe and a sodium hydroxide acidic gas absorption device was mounted, the mixture was refluxed for 1 hour under magnetic agitation, distilled under reduced pressure to remove excessive thionyl chloride to give crude 3-phenylpropionyl chloride as a pale yellow oil, which was directly used in the reaction of following step without purification.

Step 2: Preparation of 1-(4-methoxy-phenyl)-3-phenyl-propan-1-one

To a 500 ml three-necked flask provided with a mechanical agitator and a thermometer were added a solution of 22.4 g (133.2 mmol) in theoretical amount of 3-phenylpropionyl chloride which was prepared in the step 1, dissolved in 100 ml dichloromethane, 14.4 g (205.9 mmol) methylphenyl ether and 150 ml dichloromethane, the mixture was cooled in an ice salt bath to lower than −5° C., while maintaining the inside temperature at −5° C. to −10° C., 17.8 g (133.2 mmol) anhydrous AlCl$_3$ was added portionwise, upon the completion of addition. The mixture was stirred at this temperature for 1 hour and then at room temperature for 1 hour, the resultant was poured under stirring into a mixture of 100 g ice, 100 g water and 40 ml concentrated hydrochloric acid, the organic layer was separated, and the aqueous layer was extracted with dichloromethane twice ×20 ml, the organic layers were combined and washed with saturated brine, then with saturated aqueous sodium bicarbonate solution, and then with saturated brine until neutrality, dried over anhydrous magnesium sulfate, filtrated and concentrated under a reduced pressure to obtain a crude product, which was recrystallized with petroleum ether and ethyl acetate (2:1) to obtain a 23.5 g product, the mother liquid was concentrated and recrystallized to obtain a 3.3 g product in a yield of 83.7% in total, mp: 96-97☐. $^1$H-NMR (CDCl$_3$, 400 MHz) δ: 3.05 (2H, t, J=8.16 Hz), 3.25 (2H, t, J=8.16 Hz), 3.86 (3H, s, OCH3), 6.92 (2H, d, J=9.00 Hz, ArH), 7.18~7.32 (5H, m, ArH), 7.94 (2H, d, J=9.00 Hz, ArH); EI-MS m/e (%): 240.1 (M+, 37), 135 (100).

Step 3: Preparation of 2-bromo-1-(4-methoxy-phenyl)-3-phenyl-propan-1-one

To a 500 ml three-necked flask equipped with a thermometer were added 23.0 g (95.7 mmol) 1-(4-methoxy-phenyl)-3-phenyl-propan-1-one prepared in the step 2, 0.30 g (2.25 mmol) anhydrous AlCl$_3$ and 150 ml chloroform, the resulting mixture was agitated, upon the completion of the dissolution, to the mixture was added dropwise a bromide dissolved in 30 ml chloroform maintaining at 5-10° C. in an ice-bath, the dripping was controlled to make the color of bromide disappear quickly. Upon the completion of addition, the mixture was agitated at room temperature for 30 minutes, and then placed into a separating funnel, washed with water, then with saturated aqueous sodium bicarbonate solution, and then with water, dried over anhydrous sodium sulfate, filtrated and concentrated under a reduced pressure to a obtain a crude product, which was subjected to a silica gel column chromatography eluted with petroleum ether/ethyl acetate (13:1) to obtain a 28.7 g colorless liquid product, which was recrystallized with anhydrous ethanol to obtain a white solid in a yield of 93.9%, mp: 57-58☐. $^1$H-NMR (CDCl$_3$, 400 MHz) δ: 3.34 (1H, dd, J=14.28, 7.00 Hz), 3.66 (1H, dd, J=14.28, 7.00 Hz), 3.13 (3H, s, OCH3), 5.29 (1H, t, J=7.32 Hz, CHBr), 6.91 (2H, d, J=9.00 Hz, ArH), 7.18~7.32 (5H, m, ArH), 7.94 (2H, d, J=9.00 Hz, ArH); ESI-MS m/e (%): 320.8 (M+1, 100), 239.2 (M-Br, 18).

Step 4: Preparation of 5-benzyl-4-(4-methoxy-phenyl)-thiazol-2-ylamine

To a 500 ml eggplant-shaped flask were added 25.00 g (78.32 mmol) 2-bromo-1-(4-methoxy-phenyl)-3-phenyl-propan-1-one prepared in the step 3 and 150 ml anhydrous ethanol, then added 5.96 g (78.32 mmol) thiourea and 6.42 g (78.32 mmol) anhydrous sodium acetate under stirring, the resulting mixture was stirred at room temperature for 1 hour, then refluxed for 2 hours, and cooled to room temperature, and a solid was precipitated, filtered, washed with water, dried to obtain 18.01 g of a product, a single spot was shown by TLC, the product was not further purified in a yield of 77.6%, mp: 177-178☐. 1H-NMR (DMSO-d$_6$, 400 MHz) δ: 3.76 (3H, s, OCH3), 4.04 (2H, s, CH2), 6.82 (2H, s, NH2), 6.93 (2H, d, J=9.00 Hz, ArH), 7.18~7.35 (5H, m, ArH), 7.46 (2H, d, J=9.00 Hz, ArH); EI-MS m/e (%): 296.1 (M, 100), 219.0 (19); HREI-MS Calcd. for C$_{17}$H$_{16}$N$_2$OS: 296.0983.

found: 296.0978. Anal. Calcd. for $C_{17}H_{16}N_2OS$: C, 68.89; H, 5.44; N, 9.45. found: C, 69.08; H, 5.32; N, 9.57.

Example 2

Preparation of 5-benzyl-4-(4-hydroxy-phenyl)-thiazol-2-ylamine

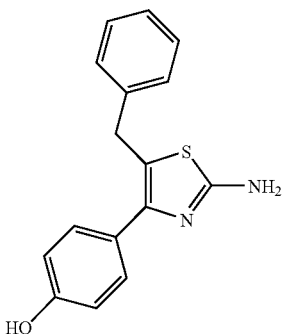

To a 50 ml eggplant-shaped flask were added 0.50 g (1.69 mmol) 5-benzyl-4-(4-methoxy-phenyl)-thiazol-2-ylamine prepared in Example 1 and 15 ml dichloromethane, and then added dropwise 2.9 ml (5.06 mmol) of 1.76 M BBR3 solution in dichloromethane. The resulting mixture was stirred at room temperature for 2 hours, the resultant was poured into 20 ml of a saturated aqueous sodium bicarbonate solution, a solid was precipitated, filtered, washed with water, and dried to obtain a crude product, which was subjected to a silica gel column chromatography eluted with petroleum ether/ethyl acetate (3:2) to obtain a 0.46 g product as a white solid in a yield of 95.8%, mp: 170-172□. 1H-NMR (DMSO-$d_6$, 400 MHz) δ: 4.02 (2H, s, CH2), 6.74~6.76 (4H, m, 2ArH+NH2), 7.15~7.40 (7H, m, ArH), 9.49 (1H, s, OH); EI-MS m/e (%): 282.0 ($M^+$, 100), 205.0 (37); HREI-MS Calcd. for $C_{16}H_{14}N_2OS$: 282.0827. found: 282.0824.

Example 3

Preparation of N-[5-benzyl-4-(4-methoxy-phenyl)-thiazol-2-yl]-benzamide

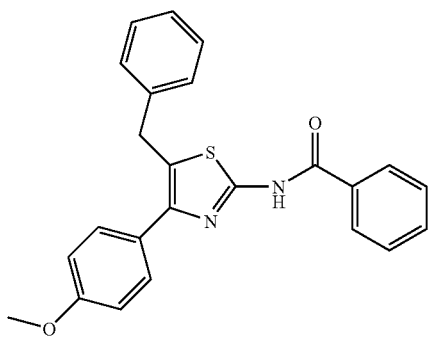

To a 100 ml three-necked flask were added 0.50 g (1.69 mmol) 5-benzyl-4-(4-methoxy-phenyl)-thiazol-2-ylamine prepared in Example 1, 1.42 g (10.12 mmol) triethylamine and 40 ml ethyl acetate, and then added dropwise 0.48 g (3.38 mmol) benzoyl chloride dissolved in 10 ml ethyl acetate. The resulting mixture was magnetically stirred overnight at room temperature, filtrated, washed with ethyl acetate, the filtrate was washed with 1N aqueous sodium hydroxide solution, then washed with water until neutrality, dried over anhydrous sodium sulfate, filtered and concentrated under a reduced pressure to give a crude product, which was subjected to a silica gel column chromatography eluted with petroleum ether/ethyl acetate (5:1) to obtain a 0.39 g product as a white solid in a yield of 57.4%, mp: 146-147 ⌊. $^1$H-NMR (CDCl$_3$, 400 MHz) δ: 3.88 (3H, s, OCH$_3$), 4.20 (2H, s, CH$_2$), 7.01 (2H, d, J=8.72 Hz, ArH), 7.31 (2H, d, J=8.72 Hz, ArH), 7.42~7.65 (7H, m, 6ArH+CONH), 8.09 (2H, d, J=7.28 Hz, ArH), 8.17 (2H, d, J=7.28 Hz, ArH); EI-MS m/e (%): 400.0 ($M^+$, 94), 104.9 (100); HREI-MS Calcd. for $C_{24}H_{20}N_2O_2S$: 400.1245. found: 400.1235.

Example 4

Preparation of N-[5-benzyl-4-(4-methoxy-phenyl)-thiazol-2-yl]-4-fluoro-benzamide

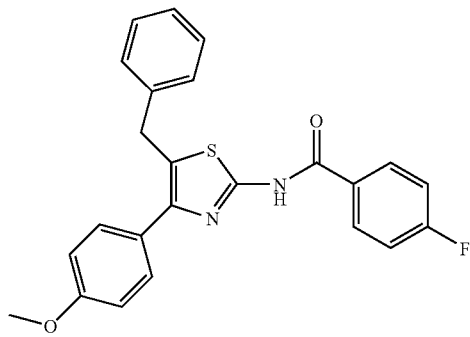

To a 50 ml eggplant-shaped flask were added 1.00 g (3.37 mmol) 5-benzyl-4-(4-methoxy-phenyl)-thiazol-2-ylamine prepared in Example 1, 0.68 g (6.75 mmol) triethylamine, 30 mg (0.25 mmol) DMAP and 25 ml THF, and then added dropwise 0.53 g (3.37 mmol) p-fluorobenzoyl chloride dissolved in 5 ml THF. The resulting mixture was stirred at room temperature for 2 hours, elevated to 35-40° C. and allowed to react for 10 hours, filtrated, washed with THF, the mother liquid was concentrated under a reduced pressure to give a pale brown oily crude product, separated with 50 ml ethyl acetate and 10 ml 1N HCl, the organic layer separated was washed with saturated aqueous sodium bicarbonate solution and then with saturated brine, dried over anhydrous sodium sulfate, filtered and concentrated to give a crude product, which was recrystallized with ethyl acetate/petroleum ether (1:2) to obtain a 1.10 g product as a white solid in a yield of 78.0%, mp: 164-165 ⌊. $^1$H-NMR (CDCl$_3$, 400 MHz) δ: 3.77 (3H, s, OCH$_3$), 4.22 (2H, s, CH$_2$), 6.76 (2H, d, J=7.84 Hz, ArH), 6.94 (2H, t, $^3J_{FH}$=$^3J_{HH}$=8.40 Hz, ArH), 7.24~7.36 (7H, m, ArH), 7.71 (2H, dd, $^3J_{HH}$=7.56, $^4J_{FH}$=5.32 Hz, ArH), 11.62 (1H, br, CONH); EI-MS m/e (%): 418.2 ($M^+$, 100), 123.0 (86); HREI-MS Calcd. for $C_{24}H_{19}FN_2O_2S$: 418.1151.

found: 418.1138. Anal. Calcd. for $C_{24}H_{19}FN_2O_2S$: C, 68.88; H, 4.58; N, 6.69. found: C, 68.77; H, 4.48; N, 6.84.

Example 5

Preparation of N-[5-benzyl-4-(4-methoxy-phenyl)-thiazol-2-yl]-4-chloro-benzamide

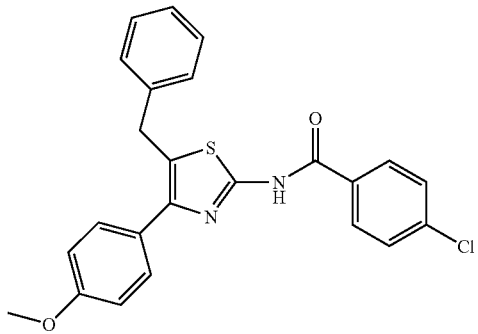

A procedure similar to that in Example 4 was used, 5-benzyl-4-(4-methoxy-phenyl)-thiazol-2-ylamine prepared in Example 1 and p-chlorobenzoyl chloride were used as starting materials, the resulting crude product was recrystallized with acetone to obtain a product as a white solid in a yield of 69.4%, mp: 182-183 ⌊. $^1$H-NMR (CDCl$_3$, 400 MHz) δ: 3.78 (3H, s, OCH$_3$), 4.21 (2H, s, CH$_2$), 6.75 (2H, d, J=7.56 Hz, ArH), 7.22~7.35 (9H, m, ArH), 7.60 (2H, d, J=7.56 Hz, ArH), 11.70 (1H, br, CONH); EI-MS m/e (%): 434.2 (M$^+$, 100), 123.0 (83); HREI-MS Calcd. for $C_{24}H_{19}ClN_2O_2S$: 434.0856. found: 434.0859. Anal. Calcd. for $C_{24}H_{19}ClN_2O_2S$: C, 66.28; H, 4.40; N, 6.44. found: C, 65.91; H, 4.22; N, 6.50.

Example 6

Preparation of 4-(4-methoxy-phenyl)-5-(4-nitro-benzyl)-thiazol-2-ylamine

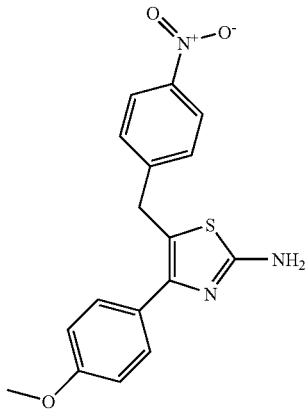

Step 1: Preparation of 3-(4-nitro-phenyl)-propionic acid

To a 1000 ml three-necked flask equipped with a thermometer were added 50.0 g (332.9 mmol) 3-phenylpropionic acid, 225 ml glacial acetic acid and 125 ml concentrated sulfuric acid, and added dropwise an acid mixture of 25.7 ml 65% nitric acid (366.2 mmol) and 35 ml concentrated sulfuric acid, premixed and cooled to about 5° C. The mixture was placed in ice-bath to keep the inside temperature at 18-25° C., maintained at 20-25° C. and stirred for 5 hours. The reaction was poured into 500 g ice, the precipitated solid was filtered, washed with water until neutrality, dried and recrystallized with ethanol to obtain a 35.8 g product as a white solid in a yield of 55.1%, 166-167 ⌊. $^1$H-NMR (CDCl$_3$, 400 MHz) δ: 2.62 (2H, t, J=7.56 Hz), 2.96 (2H, t, J=7.56 Hz), 7.53 (2H, d, J=8.68 Hz, ArH), 8.15 (2H, d, J=8.68 Hz, ArH), 12.22 (1H, s, COOH); ESI-MS m/e (%): 218.0 (M+Na, 27), 213.4 (M+NH$_3$, 3), 196.1 (M+1, 100).

Step 2: Preparation of 3-(4-nitro-phenyl)-propionyl chloride 3-(4-nitro-phenyl)-propionic acid was converted into 3-(4-nitro-phenyl)-propionyl chloride by a procedure similar to that in step 1 of Example 1, the resultant was a white solid and directly used in the following step without purification.

Step 3: Preparation of 1-(4-methoxy-phenyl)-3-(4-nitro-phenyl)-propan-1-one

A procedure similar to step 2 of Example 1 was used, the 3-(4-nitro-phenyl)-propionyl chloride prepared in the step 2 and methylphenyl ether were used as starting materials, and anhydrous AlCl$_3$ was used as catalyst, the obtained product was white solid in a yield of 81.3%, mp: 123-125 ⌊. $^1$H-NMR (CDCl$_3$, 400 MHz) δ: 3.18 (2H, t, J=7.00 Hz), 3.30 (2H, t, J=7.00 Hz), 3.87 (3H, s, OCH$_3$), 6.93 (2H, d, J=8.96 Hz, ArH), 7.42 (2H, d, J=8.60 Hz, ArH), 7.93 (2H, d, J=8.96 Hz, ArH), 8.15 (2H, d, J=8.60 Hz, ArH); EI-MS m/e (%): 285.0 (M$^+$, 62), 134 (100).

Step 4: Preparation of 2-bromo-1-(4-methoxy-phenyl)-3-(4-nitro-phenyl)-propan-1-one A procedure similar to step 3 of Example 1 was used, 1-(4-methoxy-phenyl)-3-(4-nitro-phenyl)-propan-1-one prepared in the step 3 and bromide were used as starting materials, and anhydrous AlCl$_3$ was used as catalyst, the obtained product was white crystal in a yield of 96.1%, mp: 120-122 ⌊. $^1$H-NMR (CDCl$_3$, 400 MHz) δ: 3.46 (1H, dd, J=14.28, 7.28 Hz), 3.74 (1H, dd, J=14.28, 7.28 Hz), 3.88 (3H, s, OCH$_3$), 5.27 (1H, t, J=7.28 Hz, CHBr), 6.94 (2H, d, J=8.96 Hz, ArH), 7.46 (2H, d, J=8.60 Hz, ArH), 7.96 (2H, d, J=8.96 Hz, ArH), 8.16 (2H, d, J=8.60 Hz, ArH); ESI-MS: 366.1 (M+2, 93), 364.2 (M, 100).

Step 5: Preparation of 4-(4-methoxy-phenyl)-5-(4-nitro-benzyl)-thiazol-2-ylamine To a 50 ml eggplant-shaped flask were added 0.45 g (1.24 mmol) 2-bromo-1-(4-methoxy-phenyl)-3-(4-nitro-phenyl)-propan-1-one prepared in the step 4 and 15 ml anhydrous ethanol, added 94 mg (1.24 mmol) thiourea and 101 mg (1.24 mmol) anhydrous sodium acetate under stirring. The resulting mixture was refluxed for 3 hours, distilled under a reduced pressure to remove the solvent, added 20 ml ethyl acetate and 20 ml 5% NaHCO$_3$ aqueous solution, the organic layer was separated, washed with saturated brine until neutrality, dried over anhydrous sodium sulfate, filtered and concentrated to give a crude product, which was recrystallized with ethyl acetate to obtain a 0.34 product in a yield of 79.1%, mp:

209-210 [(Dec.). $^1$H-NMR (DMSO-d$_6$, 400 MHz) δ: 3.34 (3H, s, OCH$_3$), 4.20 (2H, s, CH$_2$), 6.93 (2H, s, NH$_2$), 6.95 (2H, d, J=8.72 Hz, ArH), 7.43~7.46 (4H, m, ArH), 8.19 (2H, d, J=8.72 Hz, ArH); EI-MS m/e (%): 341.2 (M$^+$, 100), 219.1 (14); HREI-MS Calcd. for C$_{17}$H$_{15}$N$_3$O$_3$S: 341.0834. found: 341.0834. Anal. Calcd. for C$_{17}$H$_{15}$N$_3$O$_3$S: C, 59.81; H, 4.43; N, 12.31. found: C, 59.76; H, 4.36; N, 12.05.

Example 7

Preparation of N-[5-benzyl-4-(4-hydroxy-phenyl)-thiazol-2-yl]-4-fluoro-benzamide

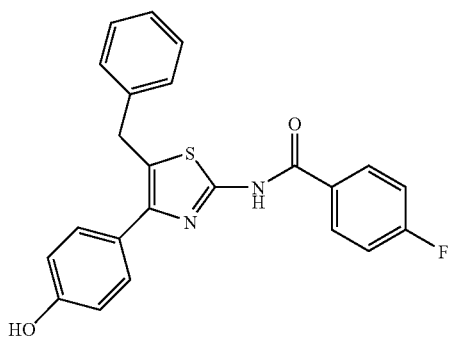

To a 100 ml three-necked flask were added 0.60 g (1.43 mmol) N-[5-benzyl-4-(4-methoxy-phenyl)-thiazol-2-yl]-4-fluoro-benzamide prepared in Example 4 and 15 ml dichloromethane, maintaining the temperature at lower than −10° C. in ice salt bath, and then added dropwise 1.7 ml of 1.763 mol/L BBr$_3$ solution in dichloromethane. Upon the completion of addition, the resulting mixture was stirred at that temperature for 1 hour and then at room temperature for 1 hour, added 2 g ice, distilled under a reduced pressure to remove dichloromethane, and then added 20 ml ethyl acetate. The organic layer was separated, washed with saturated brine, dried over anhydrous sodium sulfate, filtered and concentrated under a reduced pressure to give a crude product, which was recrystallized with ethyl acetate/petroleum ether to obtain a 0.39 product as a white solid in a yield of 67.2%, mp: 205-206 [. $^1$H-NMR (DMSO-d$_6$, 400 MHz) δ: 4.22 (2H, s, CH$_2$), 6.84 (2H, d, J=8.68 Hz, ArH), 7.23~7.39 (7H, m, ArH), 7.47 (2H, d, J=8.68 Hz, ArH), 8.15 (2H, dd, $^3$J$_{HH}$=9.00, $^4$J$_{FH}$=5.64 Hz, ArH), 9.62 (1H, s, OH), 12.66 (1H, s, CONH); EI-MS m/e (%): 404.1 (M$^+$, 100), 123.0 (70); HREI-MS Calcd. for C$_{23}$H$_{17}$FN$_2$O$_2$S: 404.0995. found: 404.0988.

Example 8

Preparation of N-[5-benzyl-4-(4-hydroxy-phenyl)-thiazol-2-yl]-4-chloro-benzamide

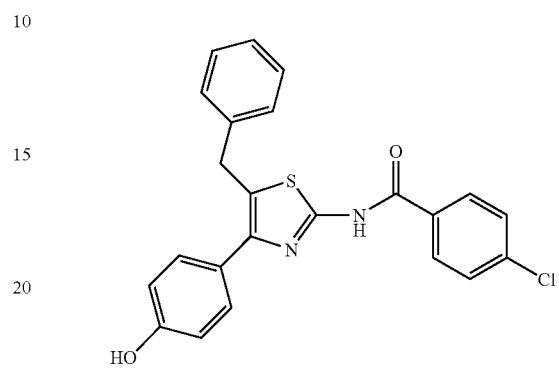

N-[5-benzyl-4-(4-methoxy-phenyl)-thiazol-2-yl]-4-chloro-benzamide prepared in Example 5 was converted into N-[5-benzyl-4-(4-hydroxy-phenyl)-thiazol-2-yl]-4-chloro-benzamide by similar procedure of Example 7, the product was a white solid in a yield of 65.1%, mp: 109-110[. $^1$H-NMR (DMSO-d$_6$, 400 MHz) δ: 4.20 (2H, s, CH$_2$), 6.83 (2H, d, J=8.68 Hz, ArH), 7.26~7.36 (7H, m, ArH), 7.42 (2H, d, J=7.56 Hz, ArH), 7.88 (2H, d, J=8.68 Hz, ArH), CONH and OH disappear; EI-MS m/e (%): 420.1 (M$^+$, 100), 123.0 (94); HREI-MS Calcd. for C$_{23}$H$_{17}$ClN$_2$O$_2$S: 420.0699. found: 420.0703.

Example 9

Preparation of 4-(4-fluoro-phenyl)-5-(4-nitro-phenyl)-thiazol-2-yl amine

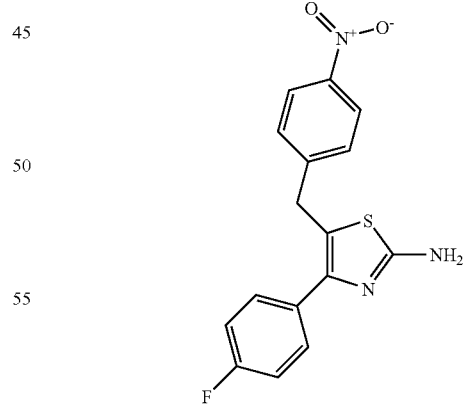

Step 1: Preparation of 1-(4-fluoro-phenyl)-3-(4-nitro-phenyl)-propan-1-one

A procedure similar to step 2 of Example 1 was used. 3-(4-nitro-phenyl)-propionyl chloride prepared in the step 2 of Example 6 and fluorobenzene were used as starting materials, and anhydrous AlCl₃ was used as catalyst. The obtained product was a white solid in a yield of 61.2%, mp: 122-124 ⌊. ¹H-NMR (CDCl₃, 400 MHz) δ: 3.19 (2H, t, J=7.28 Hz), 3.32 (2H, t, J=7.28 Hz), 7.14 (2H, t, $^3J_{FH}=^3J_{HH}$=8.40 Hz, ArH), 7.42 (2H, d, J=8.40 Hz, ArH), 7.99 (2H, dd, $^3J_{HH}$=7.84, $^4J_{FH}$=5.60 Hz, ArH), 8.16 (2H, d, J=8.40 Hz, ArH); EI-MS m/e (%): 273.1 (M⁺, 55), 123.0 (100).

Step 2: Preparation of 2-bromo-1-(4-fluoro-phenyl)-3-(4-nitro-phenyl)-propan-1-one A procedure similar to step 3 of Example 1 was used. 1-(4-fluoro-phenyl)-3-(4-nitro-phenyl)-propan-1-one prepared in the step 1 and bromide were used as starting materials, and anhydrous AlCl₃ was used as catalyst, the obtained product was a pale yellow crystal in a yield of 95.3%, mp: 126-128 ⌊. ¹H-NMR (CDCl₃, 400 MHz) δ: 3.47 (1H, dd, J=14.28, 7.28 Hz), 3.74 (1H, dd, J=14.28, 7.28 Hz), 5.25 (1H, t, J=7.28 Hz, CHBr), 7.15 (2H, t, $^3J_{FH}=^3J_{HH}$=8.40 Hz, ArH), 7.46 (2H, d, J=8.40 Hz, ArH), 8.03 (2H, dd, $^3J_{HH}$=8.72, $^4J_{FH}$=5.36 Hz, ArH), 8.17 (2H, d, J=8.40 Hz, ArH); ESI-MS (negative ion): 352.2 (M−1, 54), 350.2 (M−3, 52), 256.2 (100).

Step 3: Preparation of 4-(4-fluoro-phenyl)-5-(4-nitro-benzyl)-thiazol-2-ylamine

A procedure similar to step 5 of Example 6 was used. 2-bromo-1-(4-fluoro-phenyl)-3-(4-nitro-phenyl)-propan-1-one prepared in the step 2, thiourea and anhydrous sodium acetate were used as starting materials. The obtained crude product was recrystallized with a solvent mixture of ethyl acetate and acetone to give a product, which was a yellow solid in a yield of 71.4%, mp: 217-218 ⌊. ¹H-NMR (DMSO-d₆, 400 MHz) δ: 4.22 (2H, s, CH₂), 6.99 (2H, s, NH₂), 7.21 (2H, t, $^3J_{FH}=^3J_{HH}$=8.72 Hz, ArH), 7.47 (2H, d, J=8.96 Hz, ArH), 8.03 (2H, dd, $^3J_{HH}$=9.02, $^4J_{FH}$=5.60 Hz, ArH), 8.19 (2H, d, J=8.68 Hz, ArH); EI-MS m/e (%): 329.1 (M⁺, 100), 207.0 (21); HREI-MS Calcd. for C₁₆H₁₂FN₃O₂S: 329.0634. found: 329.0627. Anal. Calcd. for C₁₆H₁₂FN₃O₂S: C, 58.35; H, 3.67; N, 12.76. found: C, 58.61; H, 3.52; N, 12.61.

Example 10

Preparation of 4-fluoro-N-[4-(4-methoxy-phenyl)-5-(4-nitro-benzyl)-thiazol-2-yl]-benzamide

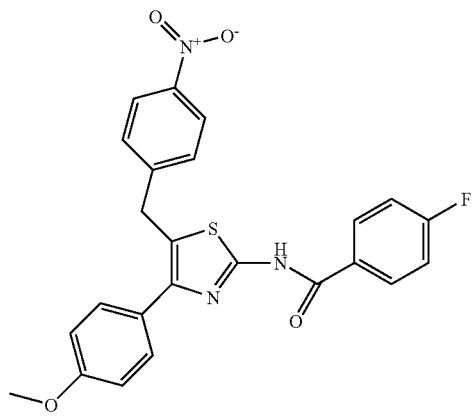

A procedure similar to that in Example 4 was used. 4-(4-methoxy-phenyl)-5-(4-nitro-benzyl)-thiazol-2-ylamine prepared in Example 6 and p-fluorobenzoyl chloride were used as starting materials, allowed to react at 35-40° C. for 48 hours, followed by post-treatment to obtain a crude product, which was purified by a silica gel column chromatography eluted with petroleum ether and ethyl acetate (4:1) to obtain a product as a yellow solid in a yield of 81.3%, mp: 188-189 ⌊. ¹H-NMR (CDCl₃, 400 MHz) δ: 3.82 (3H, s, OCH₃), 4.33 (2H, s, CH₂), 6.87 (2H, d, J=8.68 Hz, ArH), 7.10 (2H, t, $^3J_{FH}=^3J_{HH}$=8.68 Hz, ArH), 7.37 (2H, d, J=8.40 Hz, ArH), 7.39 (2H, d, J=8.68 Hz, ArH), 7.89 (2H, dd, $^3J_{HH}$=8.68, $^4J_{FH}$=5.02 Hz, ArH), 8.19 (2H, d, J=8.68 Hz, ArH); EI-MS m/e (%): 463.1 (M⁺, 60), 123.0 (100); HREI-MS Calcd. for C₂₄H₁₈FN₃O₄S: 463.1002. found: 463.1000. Anal. Calcd. for C₂₄H₁₈FN₃O₄S: C, 62.19; H, 3.91; N, 9.07. found: C, 62.21; H, 3.82; N, 9.02.

Example 11

Preparation of 4-fluoro-N-[4-(4-fluoro-phenyl)-5-(4-nitro-benzyl)-thiazol-2-yl]-benzamide

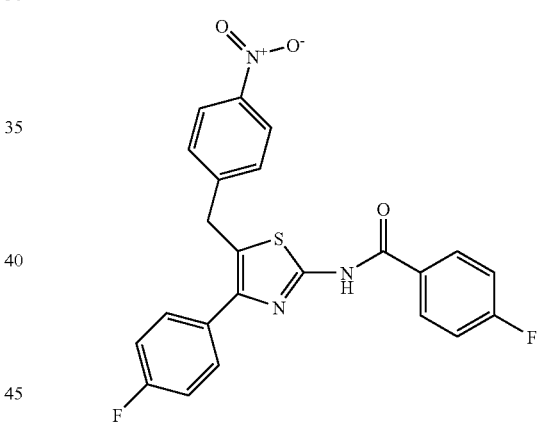

A procedure similar to that in Example 4 was used. 4-(4-fluoro-phenyl)-5-(4-nitro-benzyl)-thiazol-2-ylamine prepared in Example 9 and p-fluorobenzoyl chloride were used as starting materials, allowed to react at 35-40° C. for 24 hours, followed by post-treatment to obtain a crude product, which was purified by a silica gel column chromatography eluted with petroleum ether and ethyl acetate (4:1) to obtain a product as a pale yellow solid in a yield of 69.6%, mp: 120-122 ⌊. ¹H-NMR (CDCl₃, 400 MHz) δ: 4.33 (2H, s, CH₂), 7.12 (2H, t, $^3J_{FH}=^3J_{HH}$=8.44 Hz, ArH), 7.18 (2H, t, $^3J_{FH}=^3J_{HH}$=8.40 Hz, ArH), 7.38 (2H, d, J=8.68 Hz, ArH), 7.49 (2H, dd, $^3J_{HH}$=8.72, $^4J_{FH}$=5.32 Hz, ArH), 7.99 (2H, dd, $^3J_{HH}$=8.96, $^4J_{FH}$=5.32 Hz, ArH); 8.20 (2H, d, J=8.68 Hz, ArH); EI-MS m/e (%): 451.0 (M⁺, 32), 123.0 (100); HREI-MS Calcd. for C₂₃H₁₅F₂N₃O₃S: 451.0802. found: 451.0818.

Anal. Calcd. for $C_{23}H_{15}F_2N_3O_3S$: C, 61.19; H, 3.35; N, 9.31. found: C, 61.16; H, 3.08; N, 9.35.

Example 12

Preparation of N-[5-benzyl-4-(4-methoxy-phenyl)-thiazol-2-yl]-3,4-dimethoxy-benzamide

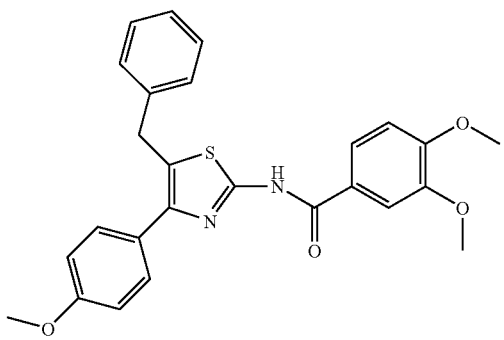

Step 1: Preparation of 3,4-dimethoxy-benzoyl chloride 3,4-dimethoxy-benzoic acid was converted into 3,4-dimethoxy-benzoyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-3,4-dimethoxy-benzamide A procedure similar to that in Example 4 was used. 5-benzyl-4-(4-methoxy-phenyl)-thiazol-2-ylamine prepared in Example 1 and 3,4-dimethoxy-benzoyl chloride prepared in the step 1 were used as starting materials, allowed to react at room temperature overnight, followed by post-treatment to obtain a crude product, which was purified by a silica gel column chromatography eluted with petroleum ether and ethyl acetate (10:1) to obtain a product as a white solid in a yield of 46.5%, mp: 179-180[. $^1$H-NMR (CDCl$_3$, 400 MHz) δ: 3.79 (3H, s, OCH$_3$), 3.83 (3H, s, OCH$_3$), 3.89 (3H, s, OCH$_3$), 4.22 (2H, s, CH$_2$), 6.73 (1H, d, J=8.40 Hz, ArH), 6.78 (2H, d, J=8.40 Hz, ArH), 7.26~7.35 (9H, m, ArH), 11.03 (1H, br, CONH); EI-MS m/e (%): 460.1 (M$^+$, 99), 164.9 (100); HREI-MS Calcd. for $C_{26}H_{24}N_2O_4S$: 460.1457. found: 460.1463. Anal. Calcd. for $C_{26}H_{24}N_2O_4S$: C, 67.81; H, 5.25; N, 6.08. found: C, 67.62; H, 5.20; N, 6.50.

Example 13

Preparation of N-[5-benzyl-4-(4-methoxy-phenyl)-thiazol-2-yl]-4-cyano-benzamide

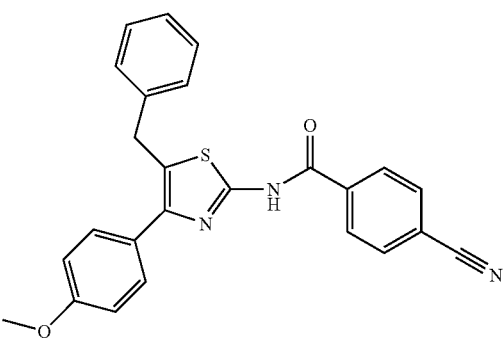

Step 1: Preparation of p-cyanobenzoyl chloride p-Cyanobenzoic acid was converted into p-cyanobenzoyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-4-cyano-benzamide A procedure similar to that in Example 4 was used. 5-benzyl-4-(4-methoxy-phenyl)-thiazol-2-ylamine prepared in Example 1 and p-cyanobenzoyl chloride prepared in the step 1 were used as starting materials, allowed to react at room temperature overnight, followed by post-treatment to obtain a crude product, which was purified by a silica gel column chromatography eluted with a gradient of petroleum ether and ethyl acetate (20:1-10:1) to obtain a product as a white solid in a yield of 39.5%, mp: 194-196 [. $^1$H-NMR (CDCl$_3$, 400 MHz) δ: 3.77 (3H, s, OCH$_3$), 4.21 (2H, s, CH$_2$), 6.69 (2H, d, J=8.68 Hz, ArH), 7.23~7.32 (5H, m, ArH), 7.36 (2H, d, J=8.68 Hz, ArH), 7.48 (2H, d, J=8.16 Hz, ArH), 7.72 (2H, d, J=8.16 Hz, ArH); EI-MS m/e (%): 425.2 (M$^+$, 100), 130.0 (40); HREI-MS Calcd. for $C_{25}H_{19}N_3O_2S$: 425.1198. found: 425.1191. Anal. Calcd. for $C_{25}H_{19}N_3O_2S$: C, 70.57; H, 4.50; N, 9.88. found: C, 70.50; H, 4.39; N, 9.99.

Example 14

Preparation of 4-cyano-N-[4-(4-methoxy-phenyl)-5-(4-nitro-benzyl)-thiazol-2-yl]-benzamide

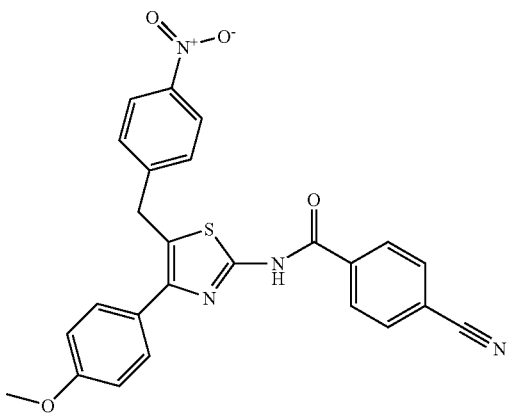

A procedure similar to that in Example 4 was used. 4-(4-methoxy-phenyl)-5-(4-nitro-benzyl)-thiazol-2-ylamine prepared in Example 6 and p-cyanobenzoyl chloride prepared in the step 1 of Example 13 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a yellow solid in a yield of 26.8%, mp: 190-192⌊. $^1$H-NMR (CDCl$_3$, 400 MHz) δ: 3.80 (3H, s, OCH$_3$), 4.32 (2H, s, CH$_2$), 6.75 (2H, d, J=8.72 Hz, ArH), 7.25 (2H, d, J=8.68 Hz, ArH), 7.37 (2H, d, J=8.68 Hz, ArH), 7.59 (2H, d, J=8.40 Hz, ArH), 7.82 (2H, d, J=8.40 Hz, ArH), 8.19 (2H, d, J=8.72 Hz, ArH); EI-MS m/e (%): 470.1 (M$^+$, 100), 130.0 (76); HREI-MS Calcd. for C$_{25}$H$_{18}$N$_4$O$_4$S: 470.1049. found: 470.1050. Anal. Calcd. for C$_{25}$H$_{18}$N$_4$O$_4$S: C, 63.82; H, 3.86; N, 11.91. found: C, 64.16; H, 3.68; N, 12.19.

Example 15

Preparation of 4-cyano-N-[4-(4-fluoro-phenyl)-5-(4-nitro-benzyl)-thiazol-2-yl]-benzamide

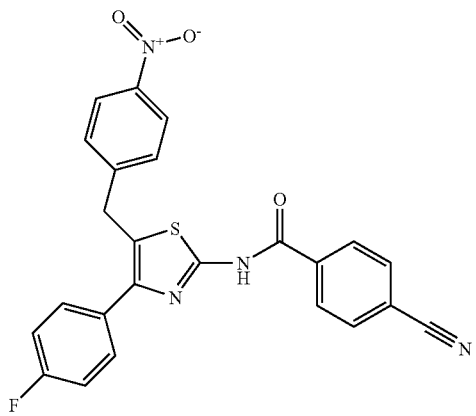

A procedure similar to that in Example 4 was used. 4-(4-fluoro-phenyl)-5-(4-nitro-benzyl)-thiazol-2-ylamine prepared in Example 9 and p-cyanobenzoyl chloride prepared in the step 1 of Example 13 were used as starting materials, allowed to react at room temperature overnight, followed by post-treatment to obtain a crude product, which was recrystallized with a solvent mixture of ethyl acetate and petroleum ether to obtain a product as a off-white solid in a yield of 62.9%, mp: 244-245⌊. $^1$H-NMR (CDCl$_3$, 400 MHz) δ: 4.33 (2H, s, CH$_2$), 7.07 (2H, t, $^3J_{FH}$=$^3J_{HH}$=8.44 Hz, ArH), 7.38 (2H, d, J=8.40 Hz, ArH), 7.43 (2H, dd, $^3J_{HH}$=8.72, $^4J_{FH}$=5.32 Hz, ArH), 7.75 (2H, d, J=7.84 Hz, ArH), 7.98 (2H, d, J=8.12 Hz, ArH), 8.20 (2H, d, J=8.40 Hz, ArH); EI-MS m/e (%): 458.3 (M$^+$, 79), 129.9 (100); HREI-MS Calcd. for C$_{24}$H$_{15}$FN$_4$O$_3$S: 458.0849. found: 458.0850. Anal. Calcd. for C$_{24}$H$_{15}$FN$_4$O$_3$S: C, 62.88; H, 3.30; N, 12.22. found: C, 62.52; H, 2.96; N, 12.04.

Example 16

Preparation of N-[5-benzyl-4-(4-methoxy-phenyl)-thiazol-2-yl]-3,5-difluoro-benzamide

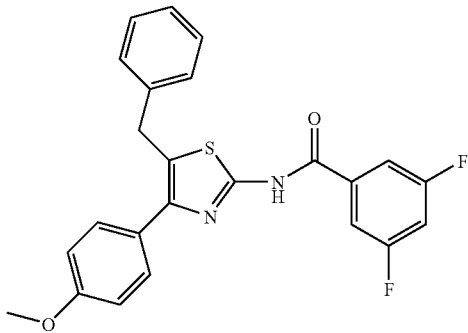

Step 1: Preparation of 3,5-difluorobenzoyl chloride 3,5-difluorobenzoic acid was converted into 3,5-difluorobenzoyl chloride by similar procedure of the step 1 of Example 1, the resultant was a colorless liquid and directly used in the following step without purification.

Step 2: Preparation of N-[5-benzyl-4-(4-methoxy-phenyl)-thiazol-2-yl]-3,5-difluoro-benzamide A procedure similar to that in Example 4 was used. 5-benzyl-4-(4-methoxy-phenyl)-thiazol-2-ylamine prepared in Example 1 and 3,5-difluorobenzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a white solid in a yield of 59.1%, mp: 154-155⌊. $^1$H-NMR (CDCl$_3$, 400 MHz) δ: 3.77 (3H, s, OCH$_3$), 4.23 (2H, s, CH$_2$), 6.72 (2H, d, J=8.44 Hz, ArH), 6.82 (1H, t, $^3J_{FH}$=8.40 Hz, ArH), 7.17~7.37 (9H, m, ArH), 11.97 (1H, br, CONH); EI-MS m/e (%): 436.1 (M$^+$, 100), 141.0 (36); HREI-MS Calcd. for C$_{24}$H$_{18}$F$_2$N$_2$O$_2$S: 436.1057. found: 436.1053. Anal. Calcd. for C$_{24}$H$_{18}$F$_2$N$_2$O$_2$S: C, 66.04; H, 4.16; N, 6.42. found: C, 66.02; H, 4.08; N, 6.44.

Example 17

Preparation of 3,5-difluoro-N-[4-(4-methoxy-phenyl)-5-(4-nitro-benzyl)-thiazol-2-yl]-benzamide

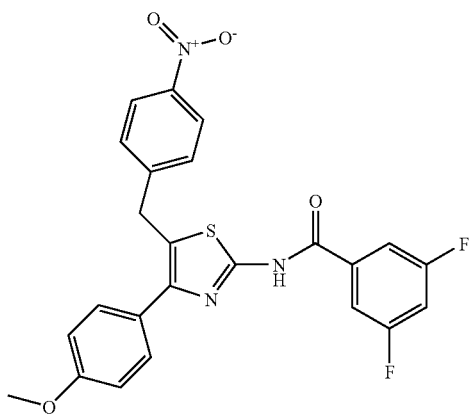

A procedure similar to that in Example 4 was used. 4-(4-methoxy-phenyl)-5-(4-nitro-benzyl)-thiazol-2-ylamine prepared in Example 6 and 3,5-difluorobenzoyl chloride prepared in the step 1 of Example 16 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a white solid in a yield of 66.7%, mp: 189-190⌊. $^1$H-NMR (CDCl$_3$, 400 MHz) δ: 3.76 (3H, s, OCH$_3$), 4.34 (2H, s, CH$_2$), 6.72 (2H, d, J=8.68 Hz, ArH), 6.85 (1H, t, $^3J_{FH}$=8.40 Hz, ArH), 7.18 (2H, d, $^3J_{FH}$=5.32 Hz, ArH), 7.25 (2H, d, J=8.68 Hz, ArH), 7.40 (2H, d, J=8.40 Hz, ArH), 8.21 (2H, d, J=8.40 Hz, ArH), 12.05 (1H, br, CONH); EI-MS m/e (%): 481.1 (M$^+$, 100), 141.0 (63); HREI-MS Calcd. for C$_{24}$H$_{17}$F$_2$N$_3$O$_4$S: 481.0908. found: 481.0902. Anal. Calcd. for C$_{24}$H$_{17}$F$_2$N$_3$O$_4$S: C, 59.87; H, 3.56; N, 8.73. found: C, 59.98; H, 3.80; N, 8.67.

Example 18

Preparation of 3,5-difluoro-N-[4-(4-fluoro-phenyl)-5-(4-nitro-benzyl)-thiazol-2-yl]-benzamide

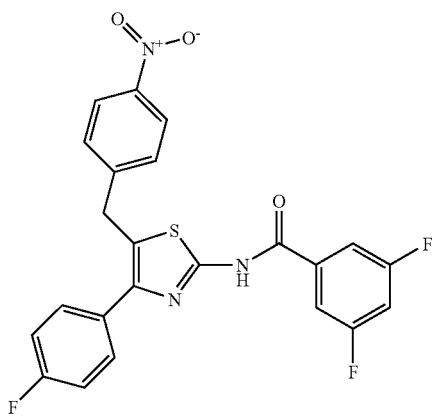

A procedure similar to that in Example 4 was used. 4-(4-fluoro-phenyl)-5-(4-nitro-benzyl)-thiazol-2-ylamine prepared in Example 9 and 3,5-difluorobenzoyl chloride prepared in the step 1 of Example 16 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a white solid in a yield of 58.0%, mp: 216-218⌊. $^1$H-NMR (DMSO-d$_6$, 400 MHz) δ: 4.44 (2H, s, CH$_2$), 7.30 (2H, t, $^3J_{FH}$=$^3J_{HH}$=8.96 Hz, ArH), 7.51 (2H, d, J=8.68 Hz, ArH), 7.30 (1H, t, $^3J_{FH}$=9.00 Hz, ArH), 7.68 (2H, dd, $^3J_{HH}$=8.68 Hz, $^4J_{FH}$=5.60 Hz, ArH), 7.30 (2H, d, $^3J_{FH}$=6.16 Hz, ArH), 8.20 (2H, d, J=8.68 Hz, ArH), 12.95 (1H, br, CONH); EI-MS m/e (%): 469.1 (M$^+$, 77), 141.1 (100); HREI-MS Calcd. for C$_{23}$H$_{14}$F$_3$N$_3$O$_3$S: 469.0708. found: 469.0710. Anal. Calcd. for C$_{23}$H$_{14}$F$_3$N$_3$O$_3$S: C, 58.85; H, 3.01; N, 8.95. found: C, 58.42; H, 2.64; N, 8.80.

Example 19

Preparation of N-[5-benzyl-4-(4-hydroxy-phenyl)-thiazol-2-yl]-3,4-dihydroxy-benzamide

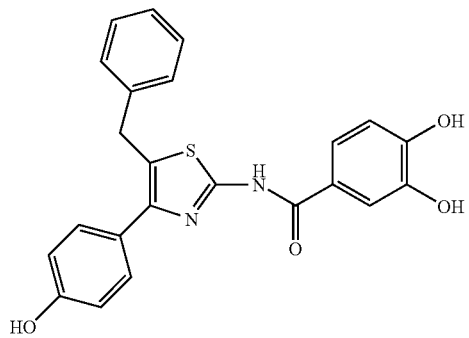

A procedure similar to that in Example 7 was used. N-[5-benzyl-4-(methoxy-phenyl)-thiazol-2-yl]-3,4-dimethoxy-benzamide prepared in Example 12 and boron tribromide were used as starting materials. The obtained crude product was purified on chromatographic column, and eluted with dichloromethane and methanol (20:1) to obtain a product as a pale yellow solid in a yield of 38.9%, mp: 240-241 ⌊(Dec). $^1$H-NMR (DMSO-d$_6$, 400 MHz) δ: 4.13 (2H, s, CH$_2$), 6.79~6.86 (3H, m, ArH), 7.21~7.36 (5H, m, ArH), 7.44~7.56 (4H, m, ArH), 9.33 (1H, br, OH), 9.61 (1H, br, OH), 9.79 (1H, br, OH), 12.26 (1H, br, CONH); EI-MS m/e (%): 418.3 (M$^+$, 39), 282.4 (100); HREI-MS Calcd. for C$_{23}$H$_{18}$N$_2$O$_4$S: 418.0987. found: 418.0976.

Example 20

Preparation of N-[4-(4-fluoro-phenyl)-5-(4-nitro-benzyl)-thiazol-2-yl]-3,4-dimethoxy-benzamide

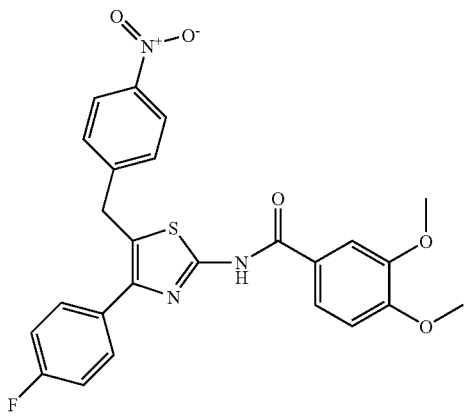

A procedure similar to that in Example 4 was used. 4-(4-fluoro-phenyl)-5-(4-nitro-benzyl)-thiazol-2-ylamine prepared in Example 9 and 3,4-dimethoxy-benzoyl chloride prepared in the step 1 of Example 12 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a white solid in a yield of 24.0%, mp: 128-129⌊. $^1$H-NMR (DMSO-$d_6$, 400 MHz) δ: 3.91 (3H, s, OCH$_3$), 3.95 (3H, s, OCH$_3$), 4.31 (2H, s, CH$_2$), 6.90 (1H, d, J=9.00 Hz, ArH), 7.08 (2H, t, J=8.68 Hz, ArH), 7.38 (2H, d, J=8.68 Hz, ArH), 7.25~7.47 (4H, m, ArH), 8.19 (2H, d, J=8.68 Hz, ArH), 10.04 (1H, br, CONH); EI-MS m/e (%): 493.2 (M$^+$, 17), 165.3 (100); HREI-MS Calcd. for C$_{25}$H$_{20}$FN$_3$O$_5$S: 493.1108. found: 493.1105.

Example 21

Preparation of 5-(4-fluoro-benzyl)-4-(4-methoxy-phenyl)-thiazol-2-ylamine

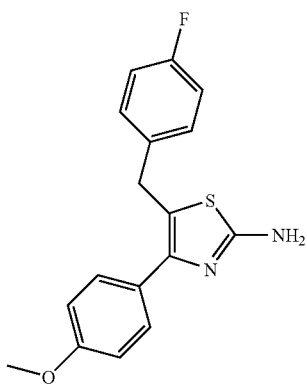

Step 1: Preparation of 3-(4-fluoro-phenyl)-propionyl chloride 3-(4-fluoro-phenyl)-propionic acid was converted into 3-(4-fluorophenyl)-propionyl chloride by similar procedure of the step 1 of Example 1, the resultant was a colorless liquid and directly used in the following step without purification.

Step 2: Preparation of 3-(4-fluoro-phenyl)-1-(4-methoxy-phenyl)-propan-1-one A procedure similar to step 2 of Example 1 was used. 3-(4-fluoro-phenyl)-propionyl chloride prepared in the step 1 and methylphenyl ether were used as starting materials, and anhydrous AlCl$_3$ was used as catalyst. The obtained product was a white solid in a yield of 100%, mp: 80-81 ⌊. $^1$H-NMR (CDCl$_3$, 400 MHz) δ: 3.05 (2H, t, J=7.84 Hz, ArH), 3.23 (2H, t, J=7.84 Hz, ArH), 3.87 (3H, s, OCH$_3$), 6.92 (2H, d, J=8.68 Hz, ArH), 6.97 (2H, t, $^3J_{FH}$=$^3J_{HH}$=8.72 Hz, ArH), 7.21 (2H, dd, $^3J_{HH}$=8.68 Hz, $^4J_{FH}$=5.60 Hz, ArH), 7.93 (2H, d, J=8.68 Hz, ArH); EI-MS m/e (%): 258.0 (M$^+$, 27), 135.0 (100).

Step 3: Preparation of 2-bromo-3-(4-fluoro-phenyl)-1-(4-methoxy-phenyl)-propan-1-one A procedure similar to step 3 of Example 1 was used. 3-(4-fluoro-phenyl)-1-(4-methoxy-phenyl)-propan-1-one prepared in the step 2 and bromide were used as starting materials, and anhydrous AlC$_3$ was used as catalyst. The obtained product was a white solid in a yield of 95.0%, mp: 76-77 ⌊. $^1$H-NMR (CDCl$_3$, 400 MHz) δ: 3.31 (1H, dd, J=14.28, 7.00 Hz), 3.66 (1H, dd, J=14.28, 7.28 Hz), 3.87 (3H, s, OCH$_3$), 5.23 (1H, t, J=7.56 Hz, CHBr), 6.93 (2H, d, J=8.96 Hz, ArH), 6.96 (2H, t, $^3J_{FH}$=$^3J_{HH}$=8.72 Hz, ArH), 7.23 (2H, dd, $^3J_{HH}$=8.68 Hz, $^4J_{FH}$=5.60 Hz, ArH), 7.95 (2H, d, J=8.96 Hz, ArH); ESI-MS: 339.2 (M+2, 89), 337.0 (M, 70), 257.2 (100).

Step 4: Preparation of 5-(4-fluoro-benzyl)-4-(4-methoxy-phenyl)-thiazol-2-ylamine A procedure similar to step 5 of Example 6 was used. 2-bromo-3-(4-fluoro-phenyl)-1-(4-methoxy-phenyl)-propan-1-one prepared in the step 3, thiourea and anhydrous sodium acetate were used as starting materials, refluxed for 2 hours, hold overnight, filtered, washed with water, and dried to obtain a product. A single spot was shown by TLC. The product was not further purified. The product was a white solid in a yield of 81.9%, mp: 199-201 ⌊. $^1$H-NMR (DMSO-$d_6$, 400 MHz) δ: 3.76 (3H, s, OCH$_3$), 4.03 (2H, s, CH$_2$), 6.84 (2H, s, NH$_2$), 6.94 (2H, d, J=8.96 Hz, ArH), 7.13 (2H, t, $^3J_{FH}$=$^3J_{HH}$=8.96 Hz, ArH), 7.23 (2H, dd, $^3J_{HH}$=8.72, $^4J_{FH}$=5.64 Hz, ArH), 7.46 (2H, d, J=8.96 Hz, ArH); EI-MS m/e (%): 314.2 (M$^+$, 100), 109.1 (12); HREI-MS Calcd. for $C_{17}H_{15}FN_2OS$: 314.0889. found: 314.0890. Anal. Calcd. for $C_{17}H_{15}FN_2OS$: C, 64.95; H, 4.81; N, 8.91. found: C, 65.10; H, 5.24; N, 8.98.

Example 22

Preparation of 3,5-difluoro-N-[5-(4-fluoro-benzyl)-4-(4-methoxy-phenyl)-thiazol-2-yl]-benzamide

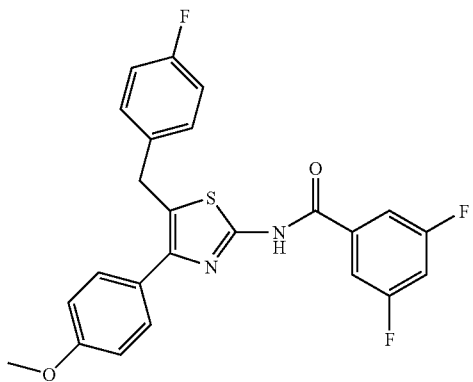

A procedure similar to that in Example 4 was used. 5-(4-fluoro-benzyl)-4-(4-methoxy-phenyl)-thiazol-2-ylamine prepared in Example 21 and p-fluorobenzoyl chloride were used as starting materials, allowed to react at room temperature overnight, followed by post-treatment to obtain a crude product, which was purified by a silica gel column chromatography, and recrystallized with petroleum ether and ethyl acetate (2:1) to obtain a product as a white solid in a yield of 75.4%, mp: 175-176 ⌊. $^1$H-NMR (CDCl$_3$, 400 MHz) δ: 3.76 (3H, s, OCH$_3$), 4.20 (2H, s, CH$_2$), 6.73 (2H, d, J=8.68 Hz, ArH), 6.83 (1H, t, $^3J_{FH}$=8.96 Hz, ArH), 6.83 (2H, t, $^3J_{FH}$=8.72 Hz, ArH), 7.15~7.22 (4H, m, ArH), 7.30 (2H, d, J=8.68 Hz, ArH); EI-MS m/e (%): 454.1 (M$^+$, 100), 140.9 (48); HREI-MS Calcd. for $C_{24}H_{17}F_3N_2O_2S$: 454.0963. found: 454.0966. Anal. Calcd. for $C_{24}H_{17}F_3N_2O_2S$: C, 63.43; H, 3.77; N, 6.16. found: C, 63.70; H, 3.70; N, 6.26.

Example 23

Preparation of 4-fluoro-N-[5-(4-fluoro-benzyl)-4-(4-methoxy-phenyl)-thiazol-2-yl]-benzamide

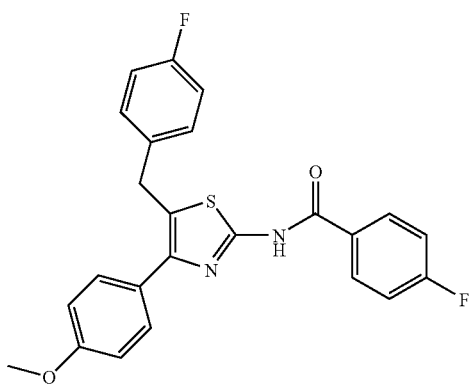

A procedure similar to that in Example 4 was used. 5-(4-fluoro-benzyl)-4-(4-methoxy-phenyl)-thiazol-2-ylamine prepared in Example 21 and 3,5-difluorobenzoyl chloride prepared in the step 1 of Example 16 were used as starting materials, allowed to react at room temperature overnight, followed by post-treatment to obtain a crude product, which was purified by a silica gel column chromatography eluted with dichloromethane and ethyl acetate (10:1) to obtain a product as a white solid in a yield of 44.5%, mp: 184-185 ⌊. $^1$H-NMR (CDCl$_3$, 400 MHz) δ: 3.80 (3H, s, OCH$_3$), 4.19 (2H, s, CH$_2$), 6.80 (2H, d, J=8.96 Hz, ArH), 6.98~7.04 (4H, m, ArH), 7.20 (2H, dd, $^3J_{HH}$=8.68, $^4J_{FH}$=5.32 Hz, ArH), 7.35 (2H, d, J=8.96 Hz, ArH), 7.77 (2H, dd, $^3J_{HH}$=8.68, $^4J_{FH}$=5.32 Hz, ArH); EI-MS m/e (%): 436.0 (M$^+$, 100), 122.9 (87); HREI-MS Calcd. for $C_{24}H_{18}F_2N_2O_2S$: 436.1057. found: 436.1056. Anal. Calcd. for $C_{24}H_{18}F_2N_2O_2S$: C, 66.04; H, 4.16; N, 6.42. found: C, 66.08; H, 4.02; N, 6.53.

Example 24

Preparation of N-[5-(4-fluoro-benzyl)-4-(4-methoxy-phenyl)-thiazol-2-yl]-N-(3,4-dimethoxy-benzamido)-3,4-dimethoxy-benzamide

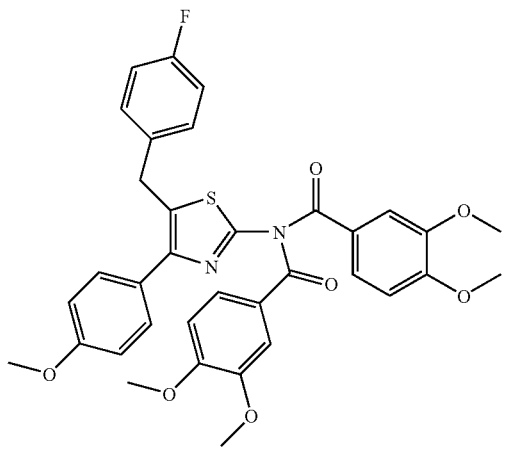

A procedure similar to that in Example 4 was used. 5-(4-fluoro-benzyl)-4-(4-methoxy-phenyl)-thiazol-2-ylamine prepared in Example 21 and 3,4-dimethoxy-benzoyl chloride prepared in the step 1 of Example 12 were used as starting materials, allowed to react at room temperature overnight, followed by post-treatment to obtain a crude product, which was purified by a silica gel column chromatography eluted with a gradient of dichloromethane and ethyl acetate (20:1-10:1) to obtain a product as a white solid in a yield of 34.2%, mp: 136-137 ⌊. $^1$H-NMR (CDCl$_3$, 400 MHz) δ: 3.70 (3H, s, OCH$_3$), 3.80 (3H, s, OCH$_3$), 3.87 (3H, s, OCH$_3$), 3.89 (6H, s, 2×OCH$_3$), 3.95 (2H, s, CH$_2$), 6.75 (1H, d, J=8.72 Hz, ArH), 6.88 (3H, d, J=8.68 Hz, ArH), 7.01 (2H, t, $^3J_{FH}$=$^3J_{HH}$=8.68 Hz, ArH), 7.18 (2H, dd, $^3J_{HH}$=8.68, $^4J_{FH}$=5.32 Hz, ArH), 7.24 (2H, d, J=8.68 Hz, ArH), 7.41~7.49 (3H, m, ArH), 7.52 (1H, d, J=8.68 Hz, ArH); EI-MS m/e (%): 642.2 (M, 7), 165.1 (100); HREI-MS Calcd. for $C_{35}H_{31}FN_2O_7S$: 642.1836. found: 642.1867.

Example 25

Preparation of 4-cyano-N-[5-(4-fluoro-benzyl)-4-(4-methoxy-phenyl)-thiazol-2-yl]-benzamide

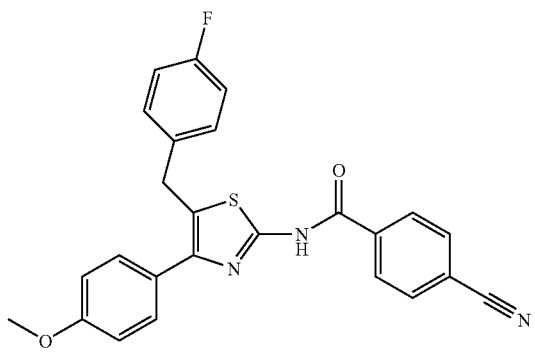

A procedure similar to that in Example 4 was used. 5-(4-fluoro-benzyl)-4-(4-methoxy-phenyl)-thiazol-2-ylamine prepared in Example 13 and p-cyanobenzoyl chloride prepared in the step 1 of Example 12 were used as starting materials, allowed to react at room temperature overnight, followed by post-treatment to obtain a crude product, which was purified by a silica gel column chromatography, and recrystallized with petroleum ether and ethyl acetate to obtain a product as a white solid in a yield of 85.9%, mp: 191-192 [. $^1$H-NMR (CDCl$_3$, 400 MHz) δ: 3.79 (3H, s, OCH$_3$), 4.18 (2H, s, CH$_2$), 6.73 (2H, d, J=8.96 Hz, ArH), 7.03 (2H, t, $^3J_{FH}=^3J_{HH}=8.68$ Hz, ArH), 7.19 (2H, dd, $^3J_{HH}=8.96$, $^4J_{FH}=5.60$ Hz, ArH), 7.24 (2H, d, J=8.96 Hz, ArH), 7.53 (2H, d, J=8.40 Hz, ArH), 7.76 (2H, d, J=8.40 Hz, ArH), 11.74 (1H, br, CONH); EI-MS m/e (%): 443.1 (M, 100), 130.0 (48); HREI-MS Calcd. for $C_{25}H_{18}FN_3O_2S$: 443.1104. found: 443.1108. Anal. Calcd. for $C_{25}H_{18}FN_3O_2S$: C, 67.71; H, 4.09; N, 9.47. found: C, 67.89; H, 3.97; N, 9.42.

Example 26

Preparation of 5-(4-nitro-benzyl)-4-phenyl-thiazol-2-ylamine

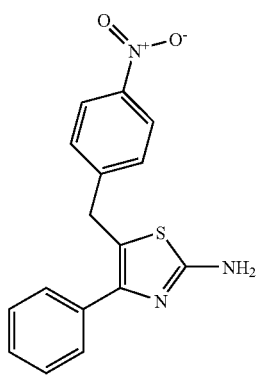

Step 1: Preparation of 3-(4-nitro-phenyl)-1-phenyl-propan-1-one

A procedure similar to step 2 of Example 1 was used. 3-(4-nitro-phenyl)-benzoyl chloride prepared in the step 2 of Example 6 and benzene were used as starting materials, and anhydrous AlC$_3$ was used as catalyst. The obtained product was a white solid in a yield of 70.3%, mp: 100-102 [. $^1$H-NMR (CDCl$_3$, 400 MHz) δ: 3.19 (2H, t, J=7.28 Hz), 3.36 (2H, t, J=7.28 Hz), 7.42~7.60 (5H, m, ArH), 7.96 (2H, d, J=7.56 Hz, ArH), 8.16 (2H, d, J=7.56 Hz, ArH); ESI-MS: 278.2 (M+Na, 100), 273.3 (M+NH$_3$+H, 49), 256.3 (M+1, 47).

Step 2: Preparation of 2-bromo-3-(4-nitro-phenyl)-1-phenyl-propan-1-one

A procedure similar to step 3 of Example 1 was used. 3-(4-nitro-phenyl)-1-phenyl-propan-1-one prepared in the step and bromide were used as starting materials, and anhydrous AlCl$_3$ was used as catalyst. The obtained product was a white solid in a yield of 90.4%, mp: 97-98 [. $^1$H-NMR (CDCl$_3$, 400 MHz) δ: 3.48 (1H, dd, J=14.28, 7.28 Hz), 3.75 (1H, dd, J=14.28, 7.28 Hz), 5.31 (1H, t, J=7.28 Hz, CHBr), 7.46~7.51 (4H, m, ArH), 7.61 (1H, t, J=8.00 Hz, ArH), 7.98 (2H, d, J=8.68 Hz, ArH), 8.17 (2H, d, J=8.68 Hz, ArH); FAB-MS: 336.1 (M+2, 90), 334.1 (M, 90), 254.2 (58), 238.2 (36), 105.1 (100).

Step 3: Preparation of 5-(4-nitro-benzyl)-4-phenyl-thiazol-2-ylamine

A procedure similar to step 5 of Example 6 was used. 2-bromo-3-(4-nitro-phenyl)-1-phenyl-propan-1-one prepared in the step 1 was used as starting material, refluxed for 2 hours, hold at room temperature overnight, the precipitated solid was filtered, washed with water, dried, and recrystallized with anhydrous ethanol to give a product in a yield of 79.5%, mp: 215-216 [. $^1$H-NMR (DMSO-d$_6$, 400 MHz) δ: 4.23 (2H, s, CH$_2$), 6.97 (2H, s, NH$_2$), 7.30 (1H, t, J=7.32 Hz, ArH), 7.38 (2H, t, J=7.28 Hz, ArH), 7.47 (2H, d, J=8.68 Hz, ArH), 7.51 (2H, d, J=7.56 Hz, ArH), 8.19 (2H, d, J=8.68 Hz, ArH); EI-MS m/e (%): 311.1 (M$^+$, 100), 189.0 (14); HREI-MS Calcd. for $C_{16}H_{13}N_3O_2S$: 311.0728. found: 311.0721. Anal. Calcd. for $C_{16}H_{13}N_3O_2S$: C, 61.72; H, 4.21; N, 13.50. found: C, 62.05; H, 4.13; N, 13.07.

Example 27

Preparation of N-[5-benzyl-4-(4-methoxy-phenyl)-thiazol-2-yl]-4-methoxy-benzamide

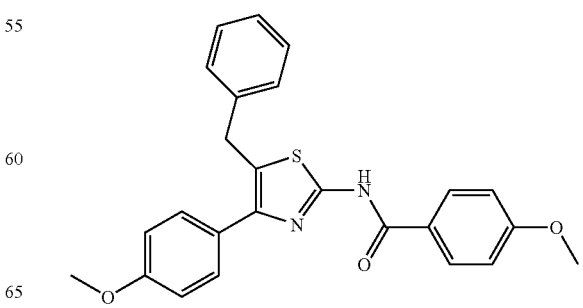

Step 1: Preparation of p-methoxybenzoyl chloride

Methoxybenzoic acid was converted into p-methoxybenzoyl chloride by similar procedure of the step 1 of Example 1, the resultant was a colorless liquid and directly used in the following step without purification.

Step 2: Preparation of N-[5-benzyl-4-(4-methoxyphenyl)-thiazol-2-yl]-4-methoxy-benzamide A procedure similar to that in Example 4 was used. 5-benzyl-4-(4-methoxy-phenyl)-thiazol-2-ylamine prepared in Example 1 and p-methoxybenzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 58.7%, mp: 58-59 ⌊. $^1$H-NMR (CDCl$_3$, 400 MHz) δ: 3.73 (3H, s, OCH$_3$), 3.85 (3H, s, OCH$_3$), 4.22 (2H, s, CH$_2$), 6.89 (4H, t, J=8.44 Hz, ArH), 7.22~7.35 (5H, m, ArH), 7.45 (2H, t, J=8.68 Hz, ArH), 7.82 (2H, t, J=8.68 Hz, ArH), 10.27 (1H, br, CONH); EI-MS m/e (%): 430.1 (M, 89), 135.0 (100); HREI-MS Calcd. for C$_{25}$H$_{22}$N$_2$O$_3$S: 430.1351. found: 430.1361.

Example 28

Preparation of 3,4-dimethoxy-N-[4-(4-methoxyphenyl)-5-(4-nitro-benzyl)-thiazol-2-yl]-benzamide

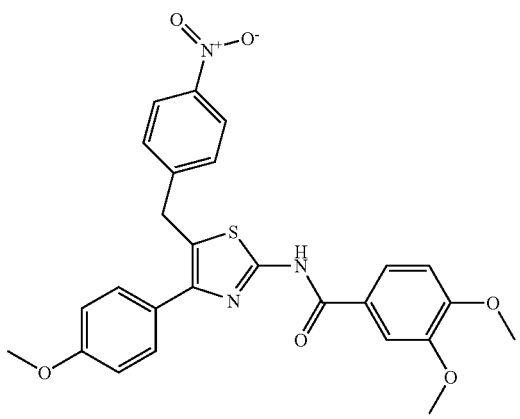

A procedure similar to that in Example 4 was used. 4-(4-methoxy-phenyl)-5-(4-nitro-benzyl)-thiazol-2-ylamine prepared in Example 6 and 3,4-dimethoxy-benzoyl chloride prepared in the step 1 of Example 12 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 60.8%, mp: 106-108⌊. $^1$H-NMR (CDCl$_3$, 400 MHz) δ: 3.83 (3H, s, OCH$_3$), 3.92 (3H, s, OCH$_3$), 3.97 (3H, s, OCH$_3$), 4.33 (2H, s, CH$_2$), 6.85~6.89 (3H, m, ArH), 7.37~7.45 (6H, m, ArH), 8.18 (2H, t, J=8.68 Hz, ArH), 10.48 (1H, br, CONH, exchangable); EI-MS m/e (%): 505.0 (M$^+$, 54), 165.0 (100); HREI-MS Calcd. for C$_{26}$H$_{23}$N$_3$O$_6$S: 505.1308. found: 505.1315. Anal. Calcd. for C$_{26}$H$_{23}$N$_3$O$_6$S: C, 61.77; H, 4.59; N, 8.31. found: C, 61.90; H, 4.70; N, 8.05.

Example 29

Preparation of 3,4-dimethoxy-N-[5-(4-nitro-benzyl)-4-phenyl-thiazol-2-yl]-benzamide

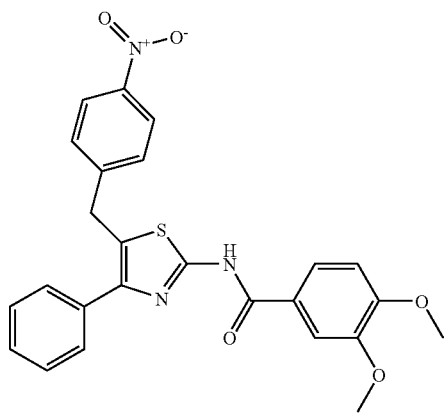

A procedure similar to that in Example 4 was used. 5-(4-nitro-benzyl)-4-phenyl-thiazol-2-ylamine prepared in Example 26 and 3,4-dimethoxy-benzoyl chloride prepared in the step 1 of Example 12 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 64.7%, mp: 105-106 ⌊. $^1$H-NMR (CDCl$_3$, 400 MHz) δ: 3.90 (3H, s, OCH$_3$), 3.96 (3H, s, OCH$_3$), 4.35 (2H, s, CH$_2$), 6.85 (1H, t, J=8.68 Hz, ArH), 7.30~7.48 (9H, m, ArH), 8.18 (2H, t, J=8.68 Hz, ArH), 10.21 (1H, br, CONH); EI-MS m/e (%): 475.0 (M$^+$, 20), 165.0 (100); HREI-MS Calcd. for C$_{25}$H$_{21}$N$_3$O$_5$S: 475.1202. found: 475.1210.

Example 30

Preparation of N-[5-(4-fluoro-benzyl)-4-(4-methoxyphenyl)-thiazol-2-yl]-3,4-dimethoxy-benzamide

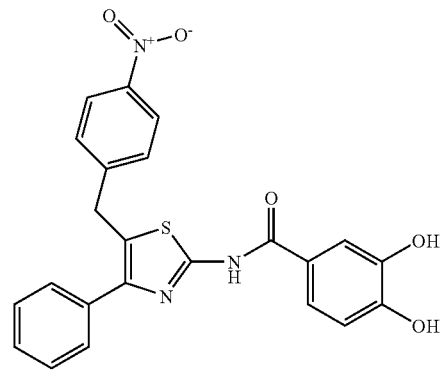

A procedure similar to that in Example 4 was used. 5-(4-fluoro-benzyl)-4-(4-methoxy-phenyl)-thiazol-2-ylamine prepared in Example 21 and 3,4-dimethoxy-benzoyl chloride prepared in the step 1 of Example 12 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 69.1%, mp: 140-142⌊. $^1$H-NMR (CDCl$_3$, 400 MHz) δ: 3.80 (3H, s, OCH$_3$), 3.84 (3H, s, OCH$_3$), 3.91 (3H, s, OCH$_3$), 4.18 (2H, s, CH$_2$), 6.79 (1H, d, J=8.68 Hz, ArH), 6.82 (2H, d, J=8.68 Hz, ArH), 7.00 (2H, t, $^3J_{FH}$=$^3J_{HH}$=8.68 Hz, ArH), 7.21 (2H, dd, $^3J_{HH}$=8.12 Hz, $^4J_{FH}$=5.32 Hz, ArH), 7.35 (4H, d, J=9.28 Hz, ArH), 11.00 (1H, br, CONH, exchangable); EI-MS m/e (%): 478.2 (M$^+$, 88), 165.0 (100); HREI-MS Calcd. for C$_{26}$H$_{23}$FN$_2$O$_4$S: 478.1363. found: 478.1361. Anal. Calcd. for C$_{26}$H$_{23}$FN$_2$O$_4$S: C, 65.26; H, 4.84; N, 5.85. found: C, 65.11; H, 4.68; N, 5.96.

Example 31

Preparation of N-[4-(4-fluoro-phenyl)-5-(4-nitro-benzyl)-thiazol-2-yl]-3,4-dihydroxy-benzamide

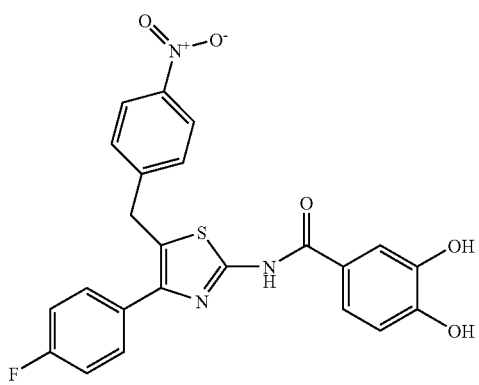

A procedure similar to that in Example 7 was used. N-[4-(4-fluoro-phenyl)-5-(4-nitro-benzyl)-thiazol-2-yl]-3,4-dimethoxy-benzamide prepared in Example 20 and boron tribromide were used as starting materials. The obtained crude product was recrystallized with acetone to give a product as a pale yellow solid in a yield of 63.3%, mp: 276-278⌊(Dec). $^1$H-NMR (DMSO-d$_6$, 400 MHz) δ: 4.41 (2H, s, CH$_2$), 6.81 (1H, d, J=8.12 Hz, ArH), 7.29 (2H, t, $^3J_{FH}$=$^3J_{HH}$=8.96 Hz, ArH), 7.47~7.54 (4H, m, ArH), 7.67 (2H, dd, $^3J_{HH}$=8.68 Hz, $^4J_{FH}$=5.60 Hz, ArH), 8.20 (2H, d, J=8.40 Hz, ArH), 9.32 (1H, br, OH), 9.81 (1H, br, OH), 12.38 (1H, br, CONH); EI-MS m/e (%): 465.0 (M$^+$, 28), 329.0 (100); HREI-MS Calcd. for C$_{23}$H$_{16}$FN$_3$O$_5$S: 465.0795. found: 465.0798.

Example 32

Preparation of 3,4-dihydroxy-N-[5-(4-nitro-benzyl)-4-phenyl-thiazol-2-yl]-benzamide

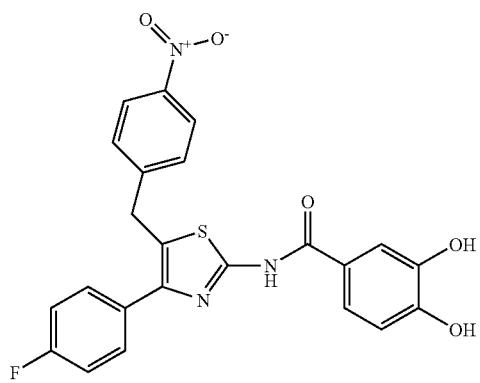

A procedure similar to that in Example 7 was used. 3,4-dimethoxy-N-[5-(4-nitro-benzyl)-4-phenyl-thiazol-2-yl]-benzamide prepared in Example 29 and boron tribromide were used as starting materials. The obtained crude product was recrystallized with acetone and ethyl acetate to give a product as a white solid in a yield of 62.8%, mp: 244⌊(Dec.). $^1$H-NMR (DMSO-d$_6$, 400 MHz) δ: 4.42 (2H, s, CH$_2$), 6.81 (1H, d, J=8.40 Hz, ArH), 7.38 (1H, t, J=7.60 Hz, ArH), 7.44~7.55 (6H, m, ArH), 7.64 (2H, d, J=8.44 Hz, ArH), 8.20 (2H, d, J=8.68 Hz, ArH), 9.32 (1H, br, OH), 9.81 (1H, br, OH), 12.38 (1H, br, CONH); EI-MS m/e (%): 447.1 (M$^+$, 16), 311.1 (100); HREI-MS Calcd. for C$_{23}$H$_{17}$N$_3$O$_5$S: 447.0889. found: 447.0887.

Example 33

Preparation of N-[5-(4-fluoro-benzyl)-4-(4-hydroxy-phenyl)-thiazol-2-yl]-3,4-dihydroxy-benzamide

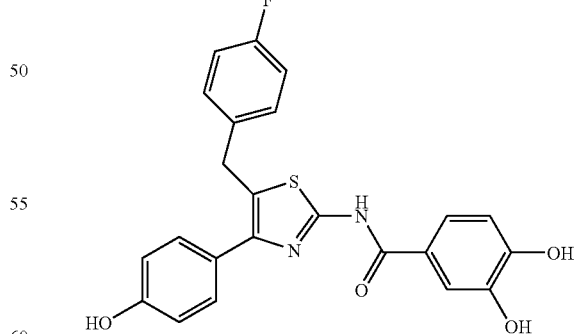

A procedure similar to that in Example 7 was used. N-[5-(4-fluoro-benzyl)-4-(4-methoxy-phenyl)-thiazol-2-yl]-3,4-dimethoxy-benzamide prepared in Example 30 and boron tribromide were used as starting materials. The obtained crude product was recrystallized with acetone to give a product of while solid in a yield of 64.4%, mp: 154-155⌊. $^1$H-NMR (DMSO-d$_6$, 400 MHz) δ: 4.19 (2H, s, CH$_2$), 6.80~6.86 (3H, m, ArH), 7.15 (2H, t, $^3J_{FH}$=$^3J_{HH}$=9.00 HZ, ArH), 7.27 (2H, dd, $^3J_{HH}$=8.72 Hz, $^4J_{FH}$=5.64 Hz, ArH), 7.43~7.56 (4H, m, ArH), 12.25 (1H, br, CONH); EI-MS m/e (%): 436.1 (M, 24), 300.1 (100); HREI-MS Calcd. for C$_{23}$H$_{17}$FN$_2$O$_4$S: 436.0893. found: 436.0900.

Example 34

Preparation of 3,4-dihydroxy-N-[4-(4-hydroxy-phenyl)-5-(4-nitro-benzyl)-thiazol-2-yl]-benzamide

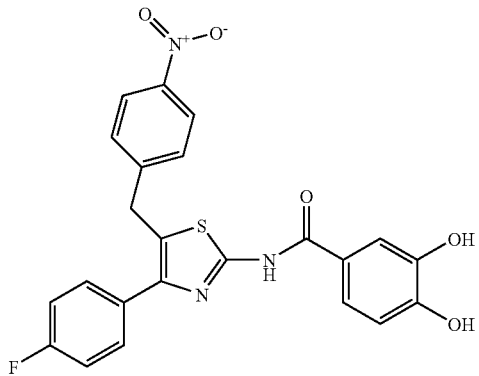

A procedure similar to that in Example 7 was used. 3,4-dimethoxy-N-[4-(4-methoxy-phenyl)-5-(4-nitro-benzyl)-thiazol-2-yl]-benzamide prepared in Example 28 and boron tribromide were used as starting materials. The obtained crude product was recrystallized with acetone to give a product as a white solid in a yield of 66.7%, mp: 195-196 ⌊. $^1$H-NMR (DMSO-d$_6$, 400 MHz) δ: 4.33 (2H, s, CH$_2$), 6.74~6.81 (3H, m, ArH), 7.37~7.50 (6H, m, ArH), 8.16 (2H, d, J=8.80 Hz, ArH), 9.30 (1H, br, OH), 9.59 (1H, br, OH), 9.77 (1H, br, OH), 12.30 (1H, br, CONH); EI-MS m/e (%): 463.1 (M$^+$, 1), 327.1 (100); HREI-MS Calcd. for C$_{23}$H$_{17}$N$_3$O$_6$S: 463.0838. found: 463.0822.

Example 35

Preparation of N-[5-benzyl-4-(4-methoxy-phenyl)-thiazol-2-yl]-2,4-dimethoxy-benzamide

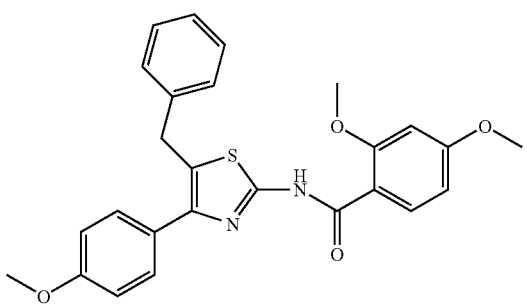

Step 1: Preparation of 2,4-dimethoxy-benzoyl chloride 2,4-dimethoxy-benzoic acid was converted into 2,4-dimethoxy-benzoyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-2,4-dimethoxy-benzamide A procedure similar to that in Example 4 was used. 5-benzyl-4-(4-methoxy-phenyl)-thiazol-2-ylamine prepared in Example 1 and 2,4-dimethoxy-benzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 71.0%, mp: 196-197 ⌊. $^1$H-NMR (CDCl$_3$, 400 MHz) δ: 3.85 (3H, s, OCH$_3$), 3.88 (3H, s, OCH$_3$), 4.08 (3H, s, OCH$_3$), 4.20 (2H, s, CH$_2$), 6.54 (1H, d, J=2.24 Hz, ArH), 6.65 (1H, dd, J=8.96 Hz, 2.24 Hz, ArH), 6.97 (2H, d, J=8.96 Hz, ArH), 7.22~7.34 (5H, m, ArH), 7.56 (2H, d, J=8.96 Hz, ArH), 8.22 (1H, d, J=8.68 Hz, ArH), 11.01 (1H, br, CONH); EI-MS m/e (%): 460.1 (M$^+$, 58), 165.0 (100); HREI-MS Calcd. for C$_{26}$H$_{24}$N$_2$O$_4$S: 460.1457. found: 460.1454. Anal. Calcd. for C$_{26}$H$_{24}$N$_2$O$_4$S: C, 67.81; H, 5.25; N, 6.08. found: C, 68.04; H, 5.16; N, 6.19.

Example 36

Preparation of N-[5-benzyl-4-(4-methoxy-phenyl)-thiazol-2-yl]-2-methoxy-benzamide

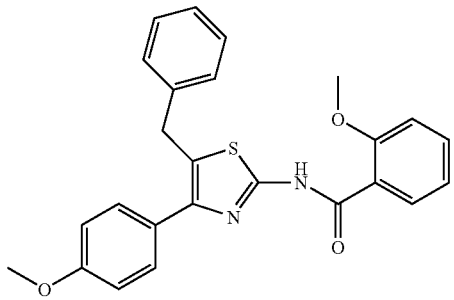

Step 1: Preparation of o-methoxybenzoyl chloride o-Methoxybenzoic acid was converted into o-methoxybenzoyl chloride by similar procedure of the step 1 of Example 1. The resultant was a colorless liquid and directly used in the following step without purification.

Step 2: Preparation of N-[5-benzyl-4-(4-methoxy-phenyl)-thiazol-2-yl]-2-methoxy-benzamide A procedure similar to that in Example 4 was used. 5-benzyl-4-(4-methoxy-phenyl)-thiazol-2-ylamine prepared in Example 1 and o-methoxybenzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 65.6%, mp: 147-148⌊. $^1$H-NMR (CDCl$_3$, 400 MHz) δ: 3.84 (3H, s, OCH$_3$), 4.09 (3H, s, OCH$_3$), 4.21 (2H, s, CH$_2$), 6.97 (2H, d, J=8.68 Hz, ArH), 7.05 (1H, d, J=8.12 Hz, ArH), 7.14 (1H, t, J=8.12 Hz, ArH), 7.22~7.32 (5H, m, ArH), 7.53~7.56 (3H, m, ArH), 8.28 (1H, dd, J=7.84 Hz, 1.68 Hz, ArH), 11.05 (1H, br, CONH); EI-MS m/e (%): 430.2 (M+, 89), 135.1 (100); HREI-MS Calcd. for $C_{25}H_{22}N_2O_3S$: 430.1351. found: 430.1357.

Example 37

Preparation of N-[5-benzyl-4-(4-methoxy-phenyl)-thiazol-2-yl]-3,4,5-trimethoxy-benzamide

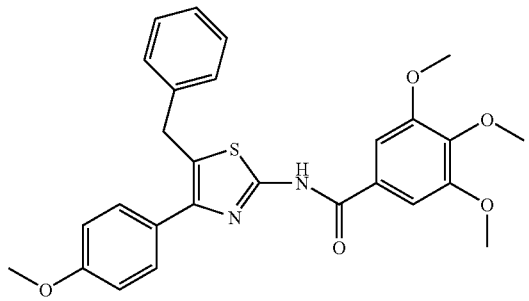

Step 1: Preparation of 3,4,5-trimethoxy-benzoyl chloride 3,4,5-trimethoxy-benzoic acid was converted into 3,4,5-trimethoxy-benzoyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-3,4,5-trimethoxy-benzamide A procedure similar to that in Example 4 was used. 5-benzyl-4-(4-methoxy-phenyl)-thiazol-2-ylamine prepared in Example 1 and 3,4,5-trimethoxy-benzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 61.7%, mp: 157-158 ⌊. ¹H-NMR (CDCl₃, 400 MHz) δ: 3.75 (6H, s, 2×OCH₃), 3.77 (3H, s, OCH₃), 3.87 (3H, s, OCH₃), 4.21 (2H, s, CH₂), 6.75 (2H, d, J=8.96 Hz, ArH), 6.92 (2H, s, ArH), 7.23~7.35 (7H, m, ArH), 11.72 (1H, br, CONH); EI-MS m/e (%): 490.3 (M, 82), 195.1 (100); HREI-MS Calcd. for $C_{27}H_{26}N_2O_5S$: 490.1562. found: 490.1560.

Example 38

Preparation of N-[5-benzyl-4-(4-hydroxy-phenyl)-thiazol-2-yl]-2,4-dihydroxy-benzamide

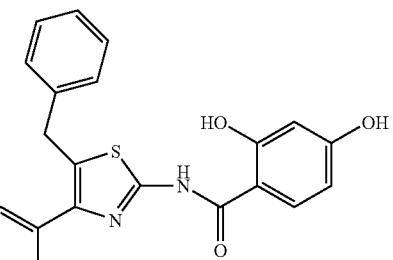

A procedure similar to that in Example 7 was used. N-[5-benzyl-4-(4-methoxy-phenyl)-thiazol-2-yl]-2,4-dimethoxy-benzamide prepared in Example 35 and boron tribromide were used as starting materials. The obtained crude product was recrystallized with acetone to give a product as a white solid in a yield of 67.1%, mp: 217-219 ⌊. ¹H-NMR (400 Hz, Acetone-d₆) δ: 4.40 (2H, s, CH₂), 6.53 (1H, d, J=2.24 Hz, ArH), 6.58 (1H, dd, J=8.96 Hz, 2.24 Hz, ArH), 7.04 (2H, d, J=8.68 Hz, ArH), 7.32~7.40 (5H, m, ArH), 7.65 (2H, d, J=8.68 Hz, ArH), 8.29 (1H, d, J=8.72 Hz, ArH); EI-MS m/e (%): 418.2 (M+, 33), 282.1 (100); HREI-MS Calcd. for $C_{23}H_{18}N_2O_4S$: 418.0987. found: 418.0970.

Example 39

Preparation of N-[5-benzyl-4-(4-hydroxy-phenyl)-thiazol-2-yl]-2-hydroxy-benzamide

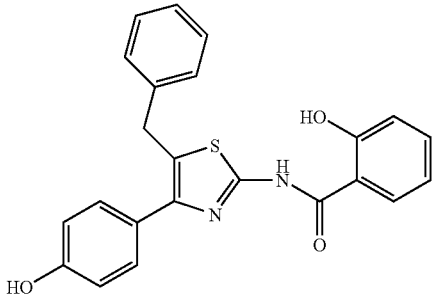

A procedure similar to that in Example 7 was used. N-[5-benzyl-4-(4-methoxy-phenyl)-thiazol-2-yl]-2-methyoxy-benzamide prepared in Example 36 and boron tribromide were used as starting materials. The obtained crude product was recrystallized with acetone to give a product as a white solid in a yield of 64.4%, mp: 279-280 ⌊. ¹H-NMR (DMSO-d₆, 400 MHz) δ: 4.19 (2H, s, CH₂), 6.85 (2H, d, J=8.40 Hz, ArH), 6.94~7.02 (2H, m, ArH), 7.22~7.28 (3H, m, ArH), 7.34 (2H, t, J=7.84 Hz, ArH), 7.42~7.48 (3H, m, ArH), 7.96 (1H, d, J=7.84 Hz, ArH), 9.70 (1H, br, OH), 12.15 (1H, br, CONH); EI-MS m/e (%): 402.2 (M+, 63), 282.1 (100); HREI-MS

Example 40

Preparation of N-[5-benzyl-4-(4-hydroxy-phenyl)-thiazol-2-yl]-4-methoxy-benzamide

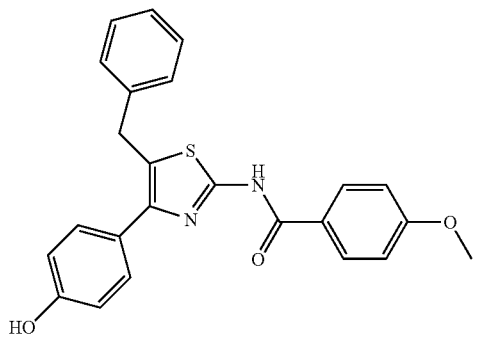

A procedure similar to that in Example 7 was used. N-[5-benzyl-4-(4-methoxy-phenyl)-thiazol-2-yl]-4-methyoxy-benzamide prepared in Example 27 and boron tribromide were used as starting materials. The obtained crude product was recrystallized with acetone to give a product as a white solid in a yield of 41.3%, mp: 124-125 [. $^1$H-NMR (DMSO-$d_6$, 400 MHz) δ: 3.84 (3H, s, $CH_3O$), 4.21 (2H, s, $CH_2$), 6.84 (2H, t, J=8.68 Hz, ArH), 7.06 (2H, t, J=8.68 Hz, ArH), 7.23~7.26 (3H, m, ArH), 7.32~7.36 (2H, m, ArH), 7.47 (2H, t, J=8.68 Hz, ArH), 8.08 (2H, t, J=8.96 Hz, ArH), 12.45 (1H, br, CONH); EI-MS m/e (%): 416.2 ($M^+$, 62), 282.1 (4), 135.1 (100); HREI-MS Calcd. for $C_{24}H_{20}N_2O_3S$: 416.1195. found: 416.1194.

Example 41

Preparation of N-[5-benzyl-4-(4-hydroxy-phenyl)-thiazol-2-yl]-3,4,5-trihydroxy-benzamide

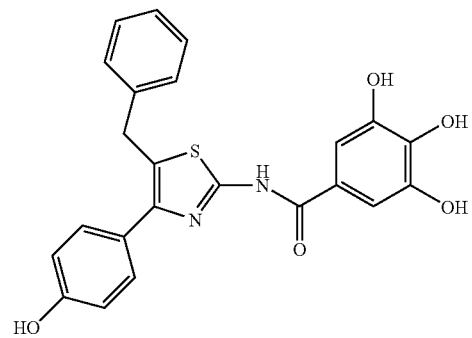

A procedure similar to that in Example 7 was used. N-[5-benzyl-4-(4-methoxy-phenyl)-thiazol-2-yl]-3,4,5-trimethoxy-benzamide prepared in Example 37 and boron tribromide were used as starting materials. The obtained crude product was recrystallized with acetone to give a product as a pale yellow solid in a yield of 61.3%, mp: 245-246 [. $^1$H-NMR (DMSO-$d_6$, 400 MHz) δ: 4.19 (2H, s, $CH_2$), 6.83 (2H, d, J=8.68 Hz, ArH), 7.06 (2H, s, ArH), 7.22~7.35 (5H, m, ArH), 7.46 (2H, d, J=8.68 Hz, ArH), 12.15 (1H, br, CONH); EI-MS m/e (%): 434.1 ($M^+$, 6), 282.1 (100); HREI-MS Calcd. for $C_{23}H_{18}N_2O_5S$: 434.0936. found: 434.0936.

Example 42

Preparation of N-[5-benzyl-4-(4-methoxy-phenyl)-thiazol-2-yl]-3-methoxy-benzamide

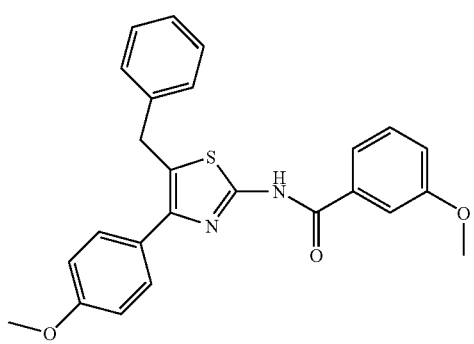

Step 1: Preparation of m-methoxybenzoyl chloride m-Methoxybenzoic acid was converted into m-methoxybenzoyl chloride by similar procedure of the step 1 of Example 1, the resultant was a colorless liquid and directly used in the following step without purification.

Step 2: Preparation of N-[5-benzyl-4-(4-methoxy-phenyl)-thiazol-2-yl]-3-methoxy-benzamide A procedure similar to that in Example 4 was used. 5-benzyl-4-(4-methoxy-phenyl)-thiazol-2-ylamine prepared in Example 1 and m-methoxybenzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 56.8%, mp: 71-72 [. $^1$H-NMR (CDCl$_3$, 400 MHz) δ: 3.80 (3H, s, OCH$_3$), 3.81 (3H, s, OCH$_3$), 4.23 (2H, s, CH$_2$), 6.85 (2H, d, J=8.80 Hz, ArH), 7.05 (1H, d, J=2.30 Hz, ArH), 7.20~7.42 (10H, m, ArH); EI-MS m/e (%): 430.1 ($M^+$, 100), 135.0 (85); HREI-MS Calcd. for $C_{25}H_{22}N_2O_3S$: 430.1351. found: 430.1352.

Calcd. for $C_{23}H_{18}N_2O_3S$: 402.1038. found: 402.1037. Anal. Calcd. for $C_{23}H_{18}N_2O_3S$: C, 68.64; H, 4.51; N, 6.96. found: C, 68.45; H, 4.38; N, 6.80.

Example 43

Preparation of N-[5-benzyl-4-(4-methoxy-phenyl)-thiazol-2-yl]-3,5-dimethoxy-benzamide

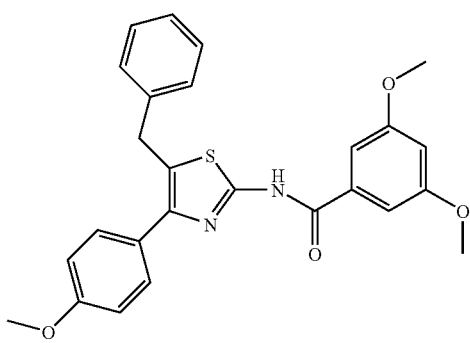

Step 1: Preparation of 3,5-dimethoxy-benzoyl chloride 3,5-dimethoxy-benzoic acid was converted into 3,5-dimethoxy-benzoyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-3,5-dimethoxy-benzamide A procedure similar to that in Example 4 was used. 5-benzyl-4-(4-methoxy-phenyl)-thiazol-2-ylamine prepared in Example 1 and 3,5-dimethoxy-benzoyl chloride prepared in the step 1 were used as starting materials, allowed to react at room temperature overnight, followed by post-treatment to obtain a crude product, which was purified by a silica gel column chromatography eluted with a gradient of dichloromethane and ethyl acetate (100:0-10:1) to obtain a product as a white solid in a yield of 65.7%, mp: 152-153 [. $^1$H-NMR (CDCl$_3$, 400 MHz) δ: 3.78 (6H, s, 2×OCH$_3$), 3.80 (3H, s, OCH$_3$), 4.22 (2H, s, CH$_2$), 6.55 (1H, t, J=2.12 Hz, ArH), 6.83 (2H, d, J=8.68 Hz, ArH), 6.90 (2H, t, J=2.12 Hz, ArH), 7.25~7.33 (5H, m, ArH), 7.39 (2H, d, J=8.68 Hz, ArH), 10.75 (1H, br, CONH); EI-MS m/e (%): 460.2 (M$^+$, 100), 165.0 (84); HREI-MS Calcd. for C$_{26}$H$_{24}$N$_2$O$_4$S: 460.1457. found: 460.1464.

Example 44

Preparation of N-[5-benzyl-4-(4-hydroxy-phenyl)-thiazol-2-yl]-3-hydroxy-benzamide

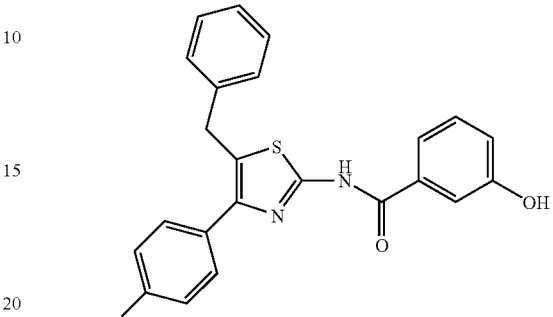

A procedure similar to that in Example 7 was used. N-[5-benzyl-4-(4-methoxy-phenyl)-thiazol-2-yl]-3-methyoxy-benzamide prepared in Example 42 and boron tribromide were used as starting materials. The obtained crude product was recrystallized with acetone to give a product as a white solid in a yield of 65.0%, mp: 233-234 [. $^1$H-NMR (DMSO-d$_6$, 400 MHz) δ: 4.23 (2H, s, CH$_2$), 6.83 (2H, d, J=7.28 Hz, ArH), 6.98~7.02 (1H, m, ArH), 7.22~7.35 (6H, m, ArH), 7.40 (1H, s, ArH), 7.46 (2H, d, J=7.28 Hz, ArH), 7.52 (1H, d, J=7.56 Hz, ArH), 9.50 (1H, br, OH), 12.50 (1H, br, CONH); EI-MS m/e (%): 402.1 (M$^+$, 83), 121.0 (100); HREI-MS Calcd. for C$_{23}$H$_{18}$N$_2$O$_3$S: 402.1038, found: 402.1042.

Example 45

Preparation of N-[5-benzyl-4-(4-hydroxy-phenyl)-thiazol-2-yl]-3,5-dihydroxy-benzamide

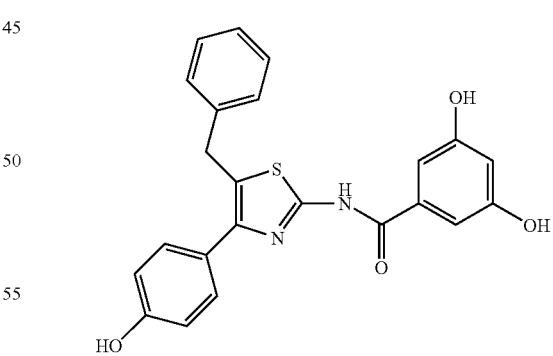

A procedure similar to that in Example 7 was used. N-[5-benzyl-4-(4-methoxy-phenyl)-thiazol-2-yl]-3,5-dimethoxy-benzamide prepared in Example 43 and boron tribromide were used as starting materials. The obtained crude product was recrystallized with acetone to give a product as a white solid in a yield of 48.2%, mp: 262-263 [. $^1$H-NMR (DMSO-d$_6$, 400 MHz) δ: 4.21 (2H, s, CH$_2$), 6.44 (1H, t, J=2.12 Hz, ArH), 6.83 (2H, d, J=8.40 Hz, ArH), 6.88 (2H, d, J=2.24 Hz, ArH), 7.22~7.26 (3H, m, ArH), 7.32~7.35 (2H, m, ArH), 7.46 (2H, d, J=8.68 Hz, ArH), 9.52 (2H, br, OH), 12.39 (1H, br, CONH); EI-MS m/e (%): 418.1 (M+, 82), 282.1 (66), 137.0 (100); HREI-MS Calcd. for $C_{23}H_{18}N_2O_4S$: 418.0987. found: 418.0981.

Example 46

Preparation of N-[5-benzyl-4-(4-hydroxy-phenyl)-thiazol-2-yl]-4-hydroxy-benzamide

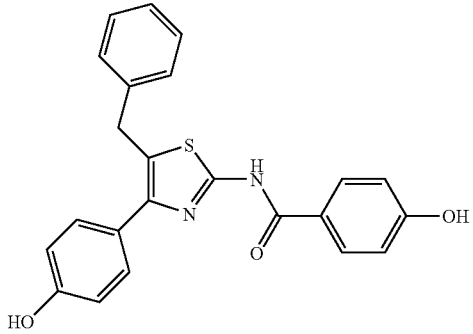

A procedure similar to that in Example 7 was used. N-[5-benzyl-4-(4-methoxy-phenyl)-thiazol-2-yl]-4-methyoxy-benzamide prepared in Example 27 and boron tribromide were used as starting materials. The obtained crude product was recrystallized with acetone to give a product as a white solid in a yield of 67.9%, mp: 254-255 [. $^1$H-NMR (DMSO-$d_6$, 400 MHz) δ: 4.20 (2H, s, $CH_2$), 6.84 (4H, t, J=7.80 Hz, ArH), 7.20~7.28 (3H, m, ArH), 7.33 (2H, t, J=8.08 Hz, ArH), 7.47 (2H, d, J=8.64 Hz, ArH), 7.97 (2H, d, J=8.60 Hz, ArH), 9.61 (1H, s, OH), 10.29 (1H, s, OH), 12.34 (1H, s, CONH); EI-MS m/e (%): 402.0 (M+, 82), 282.1 (74), 121.0 (100); HREI-MS Calcd. for $C_{23}H_{18}N_2O_3S$: 402.1038. found: 402.1027.

Example 47

Preparation of 5-cyclohexylmethyl-4-(4-methoxy-phenyl)-thiazol-2-ylamine

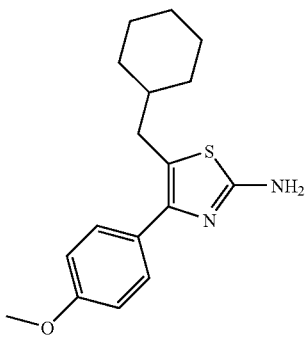

Step 1: Preparation of 3-cyclohexylpropionyl chloride 3-cyclohexylpropionic acid was converted into 3-cyclohexylpropionyl chloride by similar procedure of the step 1 of Example 1. The resultant was a colorless liquid and directly used in the following step without purification.

Step 2: Preparation of 3-cyclohexyl-1-(4-methoxy-phenyl)-propan-1-one

To a 250 ml three-necked flask were added 5.00 g (28.74 mmol) in theoretical amount of 3-cyclohexylpropionyl chloride prepared in the step 1, 3.11 g (28.74 mmol) methylphenyl ether and 150 ml dichloromethane. The resulting mixture was cooled in ice salt bath to −5° C., added portionwise 3.83 g (28.74 mmol) anhydrous $AlCl_3$ under stirring, upon the completion of addition. The mixture was stirred at room temperature for 2 hours, poured into a mixture (150 g ice+5 ml concentrated hydrochloric acid), the organic layer was separated, concentrated under a reduced pressure to about 10 ml, the aqueous layer was extracted with ethyl acetate 2×50 ml, the organic phase was combined, washed with saturated aqueous sodium bicarbonate solution and then with saturated brine, dried over anhydrous magnesium sulfate, filtrated and concentrated to obtain a pale brown solid, which was recrystallized with petroleum ether to obtain a 5.6 g product as a white solid in a yield of 79.1%, mp: 64-65 [. $^1$H-NMR ($CDCl_3$, 400 MHz) δ: 0.85~1.00 (2H, m, $CH_2$), 1.10~1.40 (4H, m, 2×$CH_2$), 1.61~1.1.82 (7H, m), 2.92 (2H, t, J=7.56 Hz, $COCH_2$), 3.87 (3H, s, $OCH_3$), 6.23 (2H, d, J=8.68 Hz, ArH), 7.94 (2H, d, J=8.68 Hz, ArH); ESI-MS m/e (%): 269.2 (M+Na, 100), 247.2 (M+1, 71).

Step 3: Preparation of 2-bromo-3-cyclohexyl-1-(4-methoxy-phenyl)-propan-1-one

A procedure similar to step 3 of Example 1 was used. 3-cyclohexyl-1-(4-methoxy-phenyl)-propan-1-one prepared in the step 2 and bromide were used as starting materials, and anhydrous $AlCl_3$ was used as catalyst, a colorless oily product was obtained in a yield of 96.6%. $^1$H-NMR ($CDCl_3$, 400 MHz) δ: 0.85~1.30 (5H, m), 1.45~1.85 (6H, m), 2.04 (2H, t, J=8.08 Hz, $CH_2CHBr$), 3.89 (3H, s, $OCH_3$), 5.24 (1H, t, J=7.48 Hz, CHBr), 6.96 (2H, d, J=9.16 Hz, ArH), 8.02 (2H, d, J=8.68 Hz, ArH); ESI-MS m/e (%): 346.9 (M+Na, 100), 327.3 (M+1, 71).

Step 4: Preparation of 5-cyclohexylmethyl-4-(4-methoxy-phenyl)-thiazol-2-ylamine A procedure similar to step 5 of Example 6 was used. 2-bromo-3-cyclohexyl-1-(4-methoxy-phenyl)-propan-1-one prepared in the step 3, thiourea and anhydrous sodium acetate were used as starting materials, refluxed for 3 hours, followed by post-treatment to give a crude product, which was purified under a reduced pressure by silica gel column chromatography eluted with petroleum ether and ethyl acetate at a ratio of 3:1 (V:V) to obtain a product as a white solid in a yield of 79.8%, mp: 118-119 [. $^1$H-NMR ($CDCl_3$, 400 MHz) δ: 0.80~0.92 (2H, m), 1.05~1.25 (3H, m), 1.40~1.50 (1H, m, CH), 1.60~1.80 (5H, m), 2.59 (2H, d, J=7.04 Hz, $CHCH_2Ar$), 3.83 (3H, s, $OCH_3$), 5.55 (2H, br, $NH_2$), 6.93 (2H, d, J=6.72 Hz, ArH), 7.44 (2H, d, J=6.72 Hz, ArH); EI-MS m/e (%): 302.2 (M+, 59), 219.1 (100), 177.1 (44); HREI-MS Calcd. for $C_{17}H_{22}N_2OS$: 302.1453. found: 302.1450. Anal. Calcd. for $C_{17}H_{22}N_2OS$: C, 67.51; H, 7.33; N, 9.26. found: C, 67.41; H, 7.47; N, 9.24.

Example 48

Preparation of N-[5-cyclohexylmethyl-4-(4-methoxy-phenyl)-thiazol-2-yl]-3,4-dimethoxy-benzamide

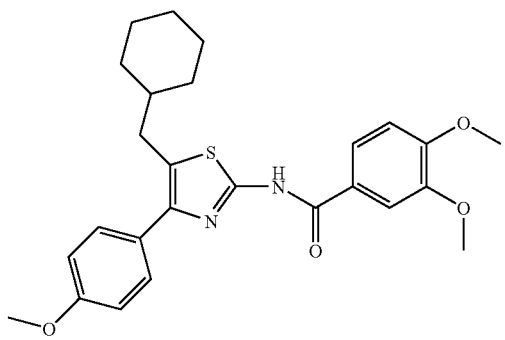

A procedure similar to that in Example 4 was used. 5-cyclohexylmethyl-4-(4-methoxy-phenyl)-thiazol-2-ylamine prepared in Example 47 and 3,4-dimethoxy-benzoyl chloride prepared in the step 1 of Example 12 were used as starting materials, allowed to react at room temperature overnight, followed by post-treatment to give a crude product, which was purified by a silica gel column chromatography eluted with a gradient of dichloromethane and ethyl acetate (20:1) to obtain a product as a white solid in a yield of 67.5%, mp: 171-172 [. $^1$H-NMR (CDCl$_3$, 400 MHz) δ: 0.82~0.98 (2H, m), 1.08~1.28 (3H, m), 1.58~1.88 (6H, m), 2.74 (2H, d, J=7.28 Hz, CHCH$_2$Ar), 3.82 (3H, s, OCH$_3$), 3.89 (3H, s, OCH$_3$), 3.94 (3H, s, OCH$_3$), 6.82~6.89 (3H, m, ArH), 7.35~7.47 (4H, m, ArH), 11.00 (1H, br, CONH); EI-MS m/e (%): 466.2 (M$^+$, 46), 383.2 (29), 165.1 (100); HREI-MS Calcd. for $C_{26}H_{30}N_2O_4S$: 466.1926. found: 466.1920. Anal. Calcd. for $C_{26}H_{30}N_2O_4S$: C, 66.93; H, 6.48; N, 6.00. found: C, 66.88; H, 6.68; N, 6.02.

Example 49

Preparation of N-[5-cyclohexylmethyl-4-(4-hydroxy-phenyl)-thiazol-2-yl]-3,4-dihydroxy-benzamide

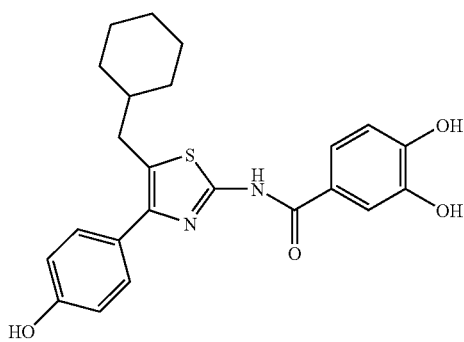

A procedure similar to that in Example 7 was used. N-[5-cyclohexylmethyl-4-(4-methoxy-phenyl)-thiazol-2-yl]-3,4-dimethoxy-benzamide prepared in Example 48 and boron tribromide were used as starting materials. The obtained crude product was recrystallized with ethyl acetate to obtain a product as a white solid in a yield of 60.5%, mp: 133-134 [. $^1$H-NMR (DMSO-d$_6$, 400 MHz) δ: 0.75~0.90 (2H, m), 0.95~1.18 (3H, m), 1.15~1.17 (6H, m), 2.65 (2H, d, J=7.0 Hz), 6.75 (1H, d, J=8.0 Hz, ArH), 6.76 (2H, d, J=8.4 Hz, ArH), 7.32 (2H, d, J=8.4 Hz, ArH), 7.41 (1H, d, J=2.4 Hz, ArH), 7.46 (1H, dd, J=8.4, 2.4 Hz, ArH), 9.52 (1H, br, OH), 12.15 (1H, br, CONH); EI-MS m/e (%): 424.1 (M$^+$, 21), 288.1 (36), 205.1 (100); HREI-MS Calcd. for $C_{23}H_{24}N_2O_4S$: 424.1457. found: 424.1458.

Example 50

Preparation of N-[5-cyclohexylmethyl-4-(4-hydroxy-phenyl)-thiazol-2-yl]-3,4,5-trimethoxy-benzamide

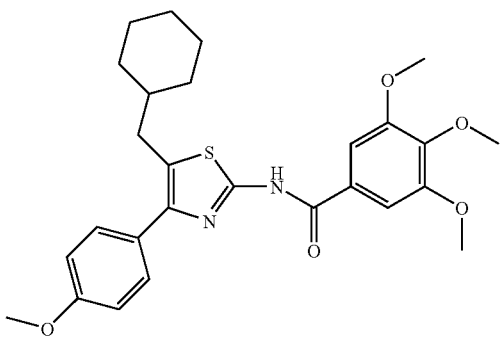

A procedure similar to that in Example 4 was used. 5-cyclohexylmethyl-4-(4-methoxy-phenyl)-thiazol-2-ylamine prepared in Example 47 and 3,4,5-trimethoxy-benzoyl chloride prepared in the step 1 of Example 37 were used as starting materials, allowed to react at room temperature overnight, followed by post-treatment to give a crude product, which was purified by a silica gel column chromatography eluted with a gradient of dichloromethane and ethyl acetate (20:1) to obtain a product as a white solid in a yield of 60.1%, mp: 193-194[. $^1$H-NMR (CDCl$_3$, 400 MHz) δ: 0.85~0.98 (2H, m), 1.05~1.28 (3H, m), 1.58~1.88 (6H, m), 2.75 (2H, d, J=7.28 Hz, CHCH$_2$Ar), 3.74 (3H, s, OCH$_3$), 3.77 (3H, s, OCH$_3$), 3.79 (3H, s, OCH$_3$), 3.97 (3H, s, OCH$_3$), 6.77 (2H, d, J=8.44 Hz, ArH), 6.98 (2H, s, ArH), 7.29 (2H, d, J=8.44 Hz, ArH); EI-MS m/e (%): 496.1 (M$^+$, 64), 413.1 (48), 195.1 (100); HREI-MS Calcd. for $C_{27}H_{32}N_2O_5S$: 496.2032. found:

496.2040. Anal. Calcd. for $C_{27}H_{32}N_2O_5S$: C, 65.30; H, 6.49; N, 5.64. found: C, 65.11; H, 6.55; N, 5.70.

Example 51

Preparation of N-[5-cyclohexylmethyl-4-(4-hydroxy-phenyl)-thiazol-2-yl]-3,4,5-trihydroxy-benzamide

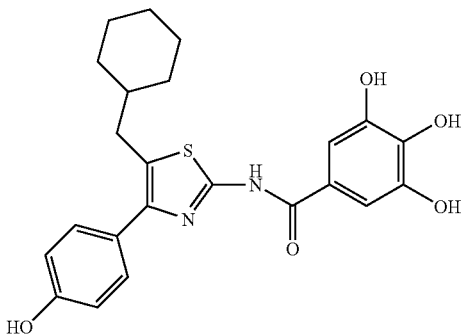

A procedure similar to that in Example 7 was used. N-[5-cyclohexylmethyl-4-(4-hydroxy-phenyl)-thiazol-2-yl]-3,4,5-trimethoxy-benzamide prepared in Example 50 and boron tribromide were used as starting materials. The obtained crude product was recrystallized with acetone to obtain a product as a white solid in a yield of 55.8%, mp: 238-239 [. $^1$H-NMR (DMSO-$d_6$, 400 MHz) δ: 0.80~0.90 (2H, m), 1.00~1.23 (3H, m), 1.45~1.75 (6H, m), 2.70 (2H, d, J=7.00 Hz, CHCH$_2$Ar), 6.84 (2H, d, J=8.68 Hz, ArH), 7.09 (2H, s, ArH), 7.38 (2H, d, J=8.68 Hz, ArH), 9.17 (4H, br, 4×OH), 12.20 (1H, br, CONH); EI-MS m/e (%): 440.0 (M$^+$, 6), 288.1 (38), 205.1 (100), 163.0 (28); HREI-MS Calcd. for $C_{23}H_{24}N_2O_5S$: 440.1406. found: 440.1406.

Example 52

Preparation of 4-(4-methoxy-phenyl)-5-methyl-thiazol-2-ylamine

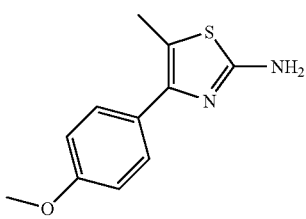

Step 1: Preparation of propionyl chloride

Propionic acid was converted into propionyl chloride by similar procedure of the step 1 of Example 1. The resultant was a colorless liquid and directly used in the following step without purification.

Step 2: Preparation of 1-(4-methoxy-phenyl)-propan-1-one

A procedure similar to step 2 of Example 47 was used. Propionyl chloride prepared in the step 1 and methylphenyl ether were used as starting materials, allowed to react in dichloromethane with AlCl$_3$ as catalyst, stirred at −5° C. to −10° C. for 30 minutes and then at room temperature for 1 hour, a crude product was obtained, purified under a reduced pressure by silica gel column chromatography eluted with petroleum ether and ethyl acetate at a ratio of 25:1 (V:V) to obtain a product of colorless liquid in a yield of 71.8%, $^1$H-NMR (CDCl$_3$, 400 MHz) δ: 1.22 (3H, t, J=7.00 Hz, CH$_2$CH$_3$), 2.96 (2H, q, J=7.00 Hz, CH$_2$CH$_3$), 3.87 (3H, s, OCH$_3$), 6.93 (2H, d, J=8.72 Hz, ArH), 7.95 (2H, d, J=8.72 Hz, ArH); ESI-MS: 187.2 (M+Na, 20), 165.2 (M+1, 100).

Step 3: Preparation of 2-bromo-1-(4-methoxy-phenyl)-propan-1-one

A procedure similar to step 3 of Example 1 was used. 1-(4-methoxy-phenyl)-propan-1-one prepared in the step 2 and bromide were used as starting materials, and anhydrous AlCl$_3$ was used as catalyst. A white solid product was obtained in a yield of 90.7%, mp: 69-70 [. $^1$H-NMR (CDCl$_3$, 400 MHz) δ: 1.89 (3H, d, J=6.44 Hz, CHBrCH$_3$), 3.88 (3H, s, OCH$_3$), 5.27 (1H, q, J=6.44 Hz, CHBrCH$_3$), 6.96 (2H, d, J=8.72 Hz, ArH), 8.02 (2H, d, J=8.72 Hz, ArH); ESI-MS m/e (%): 242.0 (M+2, 11), 241.0 (M, 11), 135.0 (100).

Step 4: Preparation of 4-(4-methoxy-phenyl)-5-methyl-thiazol-2-ylamine

A procedure similar to step 5 of Example 6 was used. 2-bromo-1-(4-methoxy-phenyl)-propan-1-one prepared in the step 3, thiourea and anhydrous sodium acetate were used as starting materials, refluxed for 4 hours, followed by post-treatment to give a crude product, which was recrystallized with anhydrous ethanol to obtain a product as a white solid in a yield of 66.8%, mp: 139-140 [. $^1$H-NMR (CDCl$_3$, 400 MHz) δ: 2.37 (3H, s, ArCH$_3$), 3.84 (3H, s, OCH$_3$), 5.09 (2H, br, NH$_2$), 6.93 (2H, d, J=8.68 Hz, ArH), 7.50 (2H, d, J=8.68 Hz, ArH); EI-MS m/e (%): 220.1 (M$^+$, 100), 205.1 (18), 163.1 (31); HREI-MS Calcd. for $C_{11}H_{12}N_2OS$: 220.0670. found: 220.0672. Anal. Calcd. for $C_{11}H_{12}N_2OS$: C, 59.98; H, 5.49; N, 12.72. found: C, 59.90; H, 5.52; N, 12.55.

Example 53

Preparation of 3,4,5-trimethoxy-N-[4-(4-methoxy-phenyl)-5-methyl-thiazol-2-yl]-benzamide

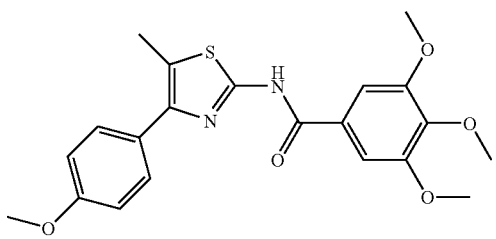

A procedure similar to that in Example 4 was used. 4-(4-methoxy-phenyl)-5-methyl-thiazol-2-ylamine prepared in Example 52 and 3,4,5-trimethoxy-benzoyl chloride prepared in the step 1 of Example 37 were used as starting materials, allowed to react at room temperature overnight, followed by post-treatment to give a crude product, which was purified by a silica gel column chromatography eluted with a gradient of dichloromethane and ethyl acetate (15:1) to obtain a product as a white solid in a yield of 63.0%, mp: 105-106 [. $^1$H-NMR (CDCl$_3$, 400 MHz) δ: 2.51 (3H, s, ArCH$_3$), 3.78 (3H, s, OCH$_3$), 3.79 (3H, s, OCH$_3$), 3.80 (3H, s, OCH$_3$), 3.89 (3H, s, OCH$_3$), 6.78 (2H, d, J=8.44 Hz, ArH), 6.98 (2H, s, ArH), 7.35 (2H, d, J=8.44 Hz, ArH); EI-MS m/e (%): 414.1 (M$^+$, 70), 195.1 (100); HREI-MS Calcd. for C$_{21}$H$_{22}$N$_2$O$_5$S: 414.1249. found: 414.1258.

Example 54

Preparation of 3,4-dimethoxy-N-[4-(4-methoxy-phenyl)-5-methyl-thiazol-2-yl]-benzamide

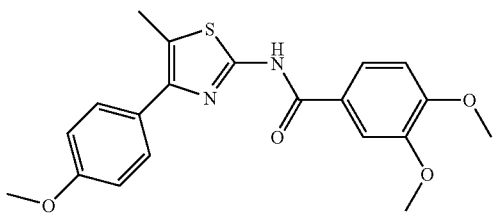

A procedure similar to that in Example 4 was used. 4-(4-methoxy-phenyl)-5-methyl-thiazol-2-ylamine prepared in Example 52 and 3,4-dimethoxy-benzoyl chloride prepared in the step 1 of Example 12 were used as starting materials, allowed to react at room temperature overnight, followed by post-treatment to give a crude product, which was purified by a silica gel column chromatography eluted with a gradient of dichloromethane and ethyl acetate (20:1) to obtain a product as a white solid in a yield of 63.5%, mp: 174-175 [. $^1$H-NMR (CDCl$_3$, 400 MHz) δ: 2.51 (3H, s, ArCH$_3$), 3.83 (3H, s, OCH$_3$), 3.92 (3H, s, OCH$_3$), 3.95 (3H, s, OCH$_3$), 6.82~6.92 (3H, m, ArH), 7.42~7.56 (4H, m, ArH), 10.83 (1H, br, CONH); EI-MS m/e (%): 384.0 (M$^+$, 66), 165.0 (100); HREI-MS Calcd. for C$_{20}$H$_{20}$N$_2$O$_4$S: 384.1144. found: 384.1143. Anal. Calcd. for C$_{20}$H$_{20}$N$_2$O$_4$S: C, 62.48; H, 5.24; N, 7.29. found: C, 62.30; H, 5.19; N, 7.30.

Example 55

Preparation of 3,4,5-trihydroxy-N-[4-(4-hydroxy-phenyl)-5-methyl-thiazol-2-yl]-benzamide

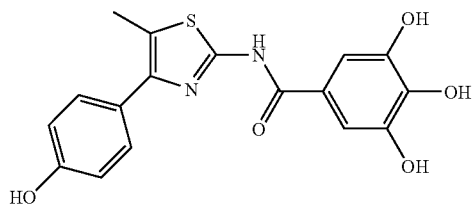

A procedure similar to that in Example 7 was used. 3,4,5-trimethoxy-N-[4-(4-methoxy-phenyl)-5-methyl-thiazol-2-yl]-benzamide prepared in Example 53 and boron tribromide were used as starting materials. The obtained crude product was recrystallized with acetone to give a product as a white solid in a yield of 60.5%, mp: 262-263 [. $^1$H-NMR (DMSO-d$_6$, 400 MHz) δ: 2.36 (3H, s, CH$_3$), 6.76 (2H, d, J=8.80 Hz, ArH), 7.02 (2H, s, ArH), 7.41 (2H, d, J=8.80 Hz, ArH), 9.10 (2H, br, OH), 9.50 (1H, br, OH), 12.06 (1H, br, CONH); EI-MS m/e (%): 358.1 (M$^+$, 25), 206.2 (100), 153.1 (20); HREI-MS Calcd. for C$_{17}$H$_{14}$N$_2$O$_5$S: 358.0623. found: 358.0621.

Example 56

Preparation of 3,4-dihydroxy-N-[4-(4-hydroxy-phenyl)-5-methyl-thiazol-2-yl]-benzamide

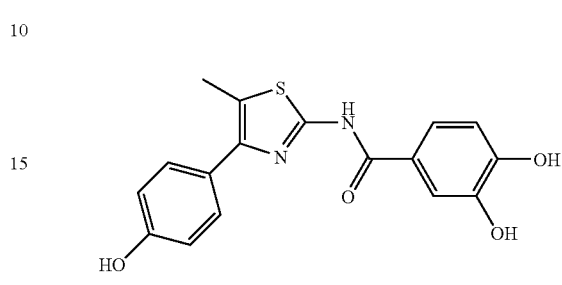

A procedure similar to that in Example 7 was used. 3,4-dimethoxy-N-[4-(4-methoxy-phenyl)-5-methyl-thiazol-2-yl]-benzamide prepared in Example 54 and boron tribromide were used as starting materials. The obtained crude product was recrystallized with acetone to give a product as a white solid in a yield of 61.2%, mp: 285[(Dec.). $^1$H-NMR (CD$_3$OD, 400 MHz) δ: 2.46 (3H, s, ArCH$_3$), 6.88~6.98 (3H, m, ArH), 7.40~7.51 (4H, m, ArH); EI-MS m/e (%): 342.1 (M$^+$, 29), 206.2 (100), 137.1 (36); HREI-MS Calcd. for C$_{17}$H$_{14}$N$_2$O$_4$S: 342.0674. found: 342.0670.

Example 57

Preparation of 4-(4-methoxy-phenyl)-5-phenylethyl-thiazol-2-ylamine

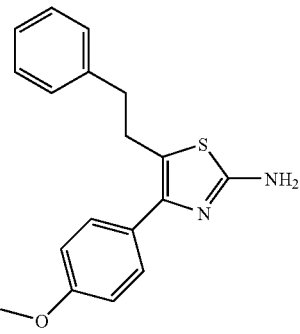

Step 1: Preparation of 4-phenylbutyryl chloride

4-Phenylbutyric acid was converted into 4-phenylbutyryl chloride by similar procedure of the step 1 of Example 1. The resultant was a colorless liquid and directly used in the following step without purification.

Step 2: Preparation of 1-(4-methoxy-phenyl)-4-phenyl-butan-1-one

A procedure similar to step 2 of 5.3.1 was used. 4-Phenylbutyryl chloride prepared in the step 1 and methylphenyl ether were used as starting materials, allowed to react in dichloromethane with AlCl$_3$ as catalyst, stirred at −10° C. to −15° C. for 30 minutes and then at room temperature for 3 hours, a crude product was obtained, purified under a reduced pressure by silica gel column chromatography eluted with a gradient of petroleum ether and ethyl acetate at a ratio of 20:1-10:1 (V:V) to obtain a product as a white crystal in a yield of 57.5%, mp: 60-61 [. $^1$H-NMR (CDCl$_3$, 400 MHz) δ: 2.07 (2H, quintuple, J=7.56 Hz), 2.72 (2H, t, J=7.56 Hz), 2.93 (2H, t, J=7.56 Hz), 3.86 (3H, s, OCH$_3$), 6.91 (2H, d, J=7.00 Hz, ArH), 7.16~7.21 (5H, m, ArH), 7.91 (2H, d, J=7.00 Hz, ArH); FAB-MS: 255.2 (M+1, 100), 150.1 (27), 135.1 (22), 91.1 (7).

Step 3: Preparation of 2-bromo-1-(4-methoxy-phenyl)-4-phenyl-butan-1-one

A procedure similar to step 3 of Example 1 was used. 1-(4-methoxy-phenyl)-4-phenyl-butan-1-one prepared in the step 2 and bromide were used as starting materials, and anhydrous AlCl$_3$ was used as catalyst. The crude product obtained was recrystallized with a mixture of petroleum ether and ethyl acetate (2:1) to give a product as a white solid in a yield of 89.4%, mp: 65-66 [. $^1$H-NMR (CDCl$_3$, 400 MHz) δ: 2.38~2.52 (2H, m, CH$_2$), 2.75~2.90 (2H, m, CH$_2$), 3.88 (3H, s, OCH$_3$), 5.03 (1H, t, J=8.00 Hz, CHBr), 6.93 (2H, d, J=9.2 Hz, ArH), 7.18~7.32 (5H, m, ArH), 7.91 (2H, d, J=9.20 Hz, ArH); ESI-MS m/e (%): 334.0 (M+2, 1), 332.0 (M, 1), 229.9 (53), 227.9 (53), 135.0 (100).

Step 4: Preparation of 4-(4-methoxy-phenyl)-5-phenylethyl-thiazol-2-ylamine

A procedure similar to step 5 of Example 6 was used. 2-bromo-1-(4-methoxy-phenyl)-4-phenyl-butan-1-one prepared in the step 3, thiourea and anhydrous sodium acetate were used as starting materials, refluxed for 3 hours, followed by post-treatment to give a crude product, which was recrystallized with anhydrous ethanol to obtain a product as a white solid in a yield of 85.9%, mp: 143-144 [. $^1$H-NMR (CDCl$_3$, 400 MHz) δ: 2.90 (2H, t, J=7.60 Hz, CH$_2$), 3.05 (2H, t, J=7.60 Hz, CH$_2$), 3.82 (3H, s, OCH$_3$), 4.99 (2H, br, NH$_2$), 6.89 (2H, d, J=8.40 Hz, ArH), 7.12~7.30 (5H, m, ArH), 7.35 (2H, d, J=8.40 Hz, ArH); EI-MS m/e (%): 310.1 (M$^+$, 23), 219.1 (100), 177.1 (39); HREI-MS Calcd. for C$_{18}$H$_{18}$N$_2$OS: 310.1140. found: 310.1140. Anal. Calcd. for C$_{18}$H$_{18}$N$_2$OS: C, 69.65; H, 5.84; N, 9.02. found: C, 69.74; H, 5.86; N, 9.03.

Example 58

Preparation of 3,4-dimethoxy-N-[4-(4-methoxy-phenyl)-5-phenylethyl-thiazol-2-yl]-benzamide

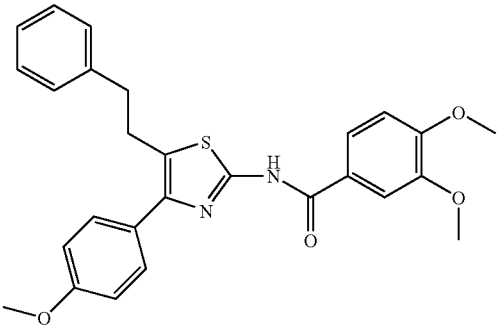

A procedure similar to that in Example 4 was used. 4-(4-methoxy-phenyl)-5-phenylethyl-thiazol-2-ylamine prepared in Example 57 and 3,4-dimethoxy-benzoyl chloride prepared in the step 1 of Example 12 were used as starting materials, allowed to react at room temperature overnight, followed by post-treatment to give a crude product, which was recrystallized with petroleum ether and ethyl acetate at a ratio of 2:1 (V:V) to obtain a product as a white solid in a yield of 76.4%, mp: 74-75 [. $^1$H-NMR (CDCl$_3$, 400 MHz) δ: 3.02 (2H, t, J=7.60 Hz, CH$_2$), 3.19 (2H, t, J=7.60 Hz, CH$_2$), 3.83 (3H, s, OCH$_3$), 3.94 (3H, s, OCH$_3$), 3.96 (3H, s, OCH$_3$), 9.85~7.95 (3H, m, ArH), 7.15~7.37 (7H, m, ArH), 7.51 (2H, s, ArH), 10.48 (1H, br, CONH); EI-MS m/e (%): 474.1 (M$^+$, 21), 383.0 (58), 165.0 (100); HREI-MS Calcd. for C$_{27}$H$_{26}$N$_2$O$_4$S: 474.1613. found: 474.1613.

Example 59

Preparation of 3,4,5-trimethoxy-N-[4-(4-methoxy-phenyl)-5-phenylethyl-thiazol-2-yl]-benzamide

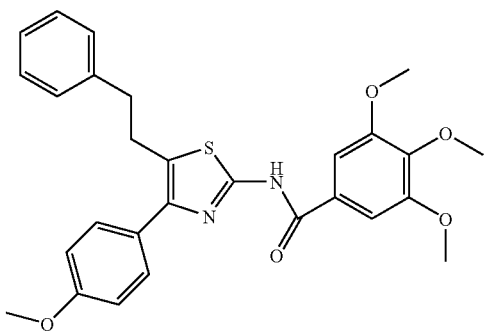

A procedure similar to that in Example 4 was used. 4-(4-methoxy-phenyl)-5-phenylethyl-thiazol-2-ylamine prepared in Example 57 and 3,4,5-trimethoxy-benzoyl chloride prepared in the step 1 of Example 37 were used as starting materials, allowed to react at room temperature overnight, followed by post-treatment to give a crude product as a foam, which was recrystallized with petroleum ether and ethyl acetate at a ratio of 2:1 (V:V) to obtain a product as a white solid in a yield of 67.2%, mp: 78-79 [. $^1$H-NMR (CDCl$_3$, 400 MHz) δ: 3.03 (2H, t, J=7.60 Hz, CH$_2$), 3.19 (2H, t, J=7.60 Hz, CH$_2$), 3.80 (6H, s, 2×OCH$_3$), 3.81 (3H, s, OCH$_3$), 3.91 (3H, s, OCH$_3$), 6.78 (2H, d, J=8.40 Hz, ArH), 7.02 (2H, s, ArH), 7.15~7.32 (7H, m, ArH), 11.54 (1H, br, CONH); EI-MS m/e (%): 504.2 (M+, 24), 413.2 (53), 195.1 (100); HREI-MS Calcd. for C28H28N2O5S: 504.1719. found: 504.1716.

Example 60

Preparation of 3,4-dihydroxy-N-[4-(4-hydroxy-phenyl)-5-phenylethyl-thiazol-2-yl]-benzamide

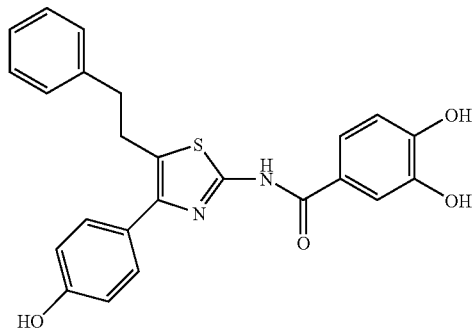

A procedure similar to that in Example 7 was used. 3,4-dimethoxy-N-[4-(4-methoxy-phenyl)-5-phenylethyl-thiazol-2-yl]-benzamide prepared in Example 58 and boron tribromide were used as starting materials, the crude product was purified by recrystallization with ethyl acetate to obtain a product as a white solid in a yield of 53.8%, mp: 208-209 ⌊. 1H-NMR (DMSO-d6, 400 MHz) δ: 2.94 (2H, t, J=7.60 Hz, CH2), 3.11 (2H, t, J=7.60 Hz, CH2), 6.81 (3H, d, J=8.40 Hz, ArH), 7.17~7.31 (5H, m, ArH), 7.35 (2H, t, J=7.60 Hz, CH2), 7.47~7.55 (2H, m, ArH), 12.23 (1H, br, CONH); EI-MS m/e (%): 432.1 (M+, 4), 205.0 (100), 163.0 (28); HREI-MS Calcd. for C24H20N2O4S: 432.1144. found: 432.1140.

Example 61

Preparation of 3,4,5-trihydroxy-N-[4-(4-hydroxy-phenyl)-5-phenylethyl-thiazol-2-yl]-benzamide

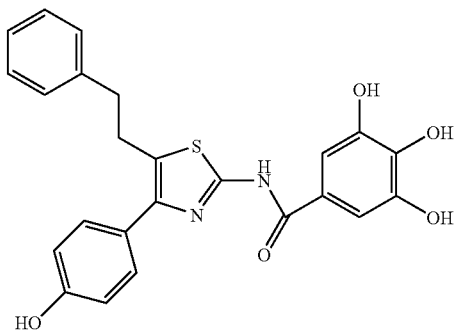

A procedure similar to that in Example 7 was used. 3,4,5-dimethoxy-N-[4-(4-methoxy-phenyl)-5-phenylethyl-thiazol-2-yl]-benzamide prepared in Example 59 and boron tribromide were used as starting materials, the crude product was purified by recrystallization with acetone to obtain a product as a white solid in a yield of 43.8%, mp: 310 ⌊(Dec.). 1H-NMR (DMSO-d6, 400 MHz) δ: 2.94 (2H, t, J=7.60 Hz, CH2), 3.13 (2H, t, J=7.60 Hz, CH2), 6.84 (2H, d, J=8.40 Hz, ArH), 7.07 (2H, s, ArH), 7.15~7.30 (5H, m, ArH), 7.33 (2H, d, J=8.40 Hz, ArH); EI-MS m/e (%): 448.2 (M+, 2), 205.0 (100), 163.0 (29); HREI-MS Calcd. for C24H20N2O5S: 448.1093. found: 448.1097.

Example 62

Preparation of 4-(4-methoxy-phenyl)-5-n-butyl-thiazol-2-ylamine

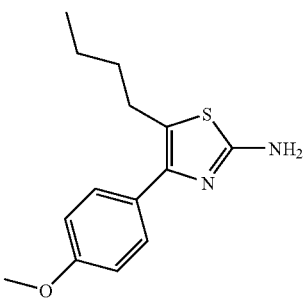

Step 1: Preparation of n-caproyl chloride n-caproic acid was converted into n-caproyl chloride by similar procedure of the step 1 of Example 1. The resultant was a colorless liquid and directly used in the following step without purification.

Step 2: Preparation of 1-(4-methoxy-phenyl)-hexan-1-one

A procedure similar to step 2 of Example 52 was used. n-Caproyl chloride prepared in the step 1 and methylphenyl ether were used as starting materials, allowed to react in dichloromethane in the presence of AlCl3 catalyst, stirred at −10° C. to −15° C. for 30 minutes and then at room temperature for 3 hours, a crude product was obtained, purified under a reduced pressure by silica gel column chromatography eluted with petroleum ether and ethyl acetate at a ratio of 20:1 to obtain a product as a waxy solid in a yield of 66.2%, mp: 39-40 ⌊. 1H-NMR (CDCl3, 400 MHz) δ: 0.91 (3H, t, J=7.20 Hz, CH3), 1.30~1.42 (4H, m, CH2CH2), 1.73 (2H, t, J=7.20 Hz, COCH2CH2), 2.91 (2H, t, J=7.20 Hz, COCH2CH2), 3.87 (3H, s, OCH3), 6.93 (2H, d, J=8.80 Hz, ArH), 7.96 (2H, d, J=8.80 Hz, ArH); ESI-MS m/e (%): 206.1 (M, 5), 163.0 (6), 150.0 (58), 135.0 (100).

Step 3: Preparation of 2-bromo-1-(4-methoxy-phenyl)-hexan-1-one

A procedure similar to step 3 of Example 1 was used. 1-(4-methoxy-phenyl)-hexan-1-one prepared in the step 2 and bromide were used as starting materials, and anhydrous AlCl3 was used as catalyst. The crude product obtained was distilled under a reduced pressure and purified by a silica gel column chromatography eluted with petroleum ether and ethyl acetate (20:1) to give a product as a white solid in a yield of 93.4%, mp: 54-55 ⌊. 1H-NMR (CDCl3, 400 MHz) δ: 0.92 (3H, t, J=7.2 Hz, CH3), 1.30~1.60 (4H, m, CH2CH2), 2.05~2.25 (2H, m, CH2CHBr), 3.89 (3H, s, OCH3), 5.11 (1H, t, J=7.2 Hz, CHBr), 6.96 (2H, d, J=8.80 Hz, ArH), 8.01 (2H, d, J=8.80 Hz, ArH); ESI-MS m/e (%): 286.1 (M+2, 2), 284.1 (M, 2), 230.0 (3), 228.0 (3), 205.1 (5), 135.1 (100).

Step 4: Preparation of 5-n-butyl-4-(4-methoxy-phenyl)-thiazol-2-ylamine

A procedure similar to step 5 of Example 6 was used. 2-bromo-1-(4-methoxy-phenyl)-hexan-1-one prepared in the step 3, thiourea and anhydrous sodium acetate were used as starting materials, refluxed for 3 hours, followed by post-treatment to give a crude product, which was recrystallized with petroleum ether and ethyl acetate at a ratio of 1:1 (V:V) to obtain a product as a white solid in a yield of 57.2%, mp: 118-119 [. $^1$H-NMR (CDCl$_3$, 400 M.Hz) δ: 0.90 (3H, t, J=7.2 Hz, CH$_3$), 1.36 (2H, sextuple, J=7.20 Hz, CH$_2$), 1.59 (2H, quintuple, J=7.20 Hz, CH$_2$), 2.74 (2H, t, J=7.2 Hz, CH$_3$), 3.83 (3H, s, OCH$_3$), 4.93 (2H, br, NH$_2$), 6.93 (2H, d, J=8.80 Hz, ArH), 7.45 (2H, d, J=8.80 Hz, ArH); EI-MS m/e (%): 262.0 (M$^+$, 55), 219.0 (100), 177.0 (36); HREI-MS Calcd. for C$_{14}$H$_{18}$N$_2$OS: 262.1140. found: 262.1140. Anal. Calcd. for C$_{14}$H$_{18}$N$_2$OS: C, 64.09; H, 6.92; N, 10.68. found: C, 64.19; H, 7.02; N, 10.63.

Example 63

Preparation of N-[5-n-butyl-4-(4-methoxy-phenyl)-thiazol-2-yl]-3,4-dimethoxy-benzamide

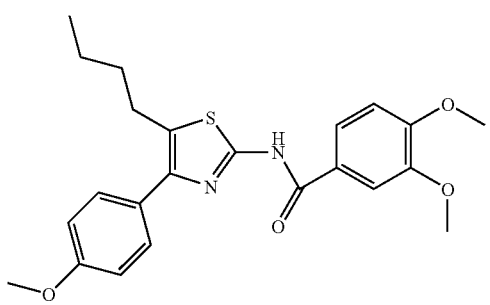

A procedure similar to that in Example 4 was used. 4-(4-methoxy-phenyl)-5-n-butyl-thiazol-2-ylamine prepared in Example 62 and 3,4-dimethoxy-benzoyl chloride prepared in the step 1 of Example 12 were used as starting materials, allowed to react at room temperature overnight, followed by post-treatment to give a crude product, which was recrystallized with petroleum ether and ethyl acetate at a ratio of 2:1 (V:V) to obtain a product as a white solid in a yield of 62.8%, mp: 150-151 [. $^1$H-NMR (CDCl$_3$, 400 MHz) δ: 0.93 (3H, t, J=7.2 Hz, CH$_3$), 1.41 (2H, sextuple, J=7.20 Hz, CH$_2$), 1.72 (2H, quintuple, J=7.20 Hz, CH$_2$), 2.88 (2H, t, J=7.2 Hz, CH$_3$), 3.80 (3H, s, OCH$_3$), 3.83 (3H, s, OCH$_3$), 3.94 (3H, s, OCH$_3$), 6.72~6.82 (3H, m, ArH), 7.25~7.40 (4H, m, ArH), 11.16 (1H, br, CONH); EI-MS m/e (%): 426.1 (M$^+$, 50), 383.1 (7), 165.1 (100); HREI-MS Calcd. for C$_{23}$H$_{26}$N$_2$O$_4$S: 426.1613. found: 426.1613. Anal. Calcd. for C$_{23}$H$_{26}$N$_2$O$_4$S: C, 64.77; H, 6.14; N, 6.57. found: C, 64.56; H, 6.23; N, 6.61.

Example 64

Preparation of N-[5-n-butyl-4-(4-methoxy-phenyl)-thiazol-2-yl]-3,4,5-trimethoxy-benzamide

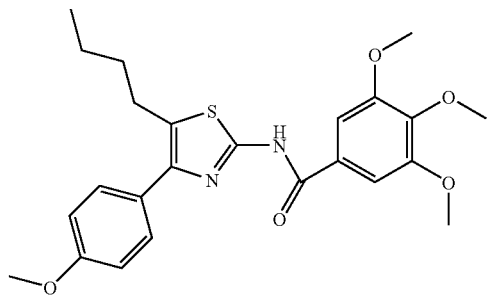

A procedure similar to that in Example 4 was used. 4-(4-methoxy-phenyl)-5-n-butyl-thiazol-2-ylamine prepared in Example 62 and 3,4,5-trimethoxy-benzoyl chloride prepared in the step 1 of Example 37 were used as starting materials, allowed to react at room temperature overnight, followed by post-treatment to give a glassy crude product, which was recrystallized with petroleum ether and ethyl acetate at a ratio of 2:1 (V:V) to obtain a product as a white solid in a yield of 51.8%, mp: 197-198 [. $^1$H-NMR (CDCl$_3$, 400 MHz) δ: 0.93 (3H, t, J=7.2 Hz, CH$_3$), 1.43 (2H, sextuple, J=7.20 Hz, CH$_2$), 1.72 (2H, quintuple, J=7.20 Hz, CH$_2$), 2.88 (2H, t, J=7.2 Hz, CH$_3$), 3.75 (6H, s, 2×OCH$_3$), 3.78 (3H, s, OCH$_3$), 3.89 (3H, s, OCH$_3$), 6.74 (2H, d, J=8.80 Hz, ArH), 6.91 (2H, s, ArH), 7.28 (2H, d, J=8.80 Hz, ArH), 11.96 (1H, br, CONH); EI-MS m/e (%): 456.1 (M$^+$, 49), 413.1 (7), 195.1 (100); HREI-MS Calcd. for C$_{24}$H$_{28}$N$_2$O$_5$S: 456.1719. found: 456.1718. Anal. Calcd. for C$_{24}$H$_{28}$N$_2$O$_5$S: C, 63.14; H, 6.18; N, 6.14. found: C, 63.24; H, 6.20; N, 6.25.

Example 65

Preparation of N-[5-n-butyl-4-(4-hydroxy-phenyl)-thiazol-2-yl]-3,4-dihydroxy-benzamide

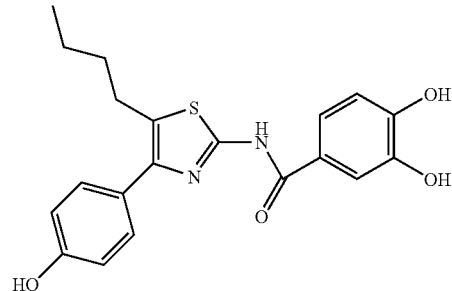

A procedure similar to that in Example 7 was used. N-[5-n-butyl-4-(4-methoxy-phenyl)-thiazol-2-yl]-3,4-dimethoxy-benzamide prepared in Example 63 and boron tribromide were used as starting materials, the crude product was purified by recrystallization with acetone to give a product as a white solid in a yield of 43.6%, mp: 189-190 [. $^1$H-NMR (DMSO-$d_6$, 400 MHz) δ: 0.88 (3H, t, J=7.2 Hz, $CH_3$), 1.35 (2H, sextuple, J=7.20 Hz, $CH_2$), 1.62 (2H, quintuple, J=7.20 Hz, $CH_2$), 2.82 (2H, t, J=7.2 Hz, $CH_3$), 6.07 (3H, br, OH), 7.65~7.85 (3H, m, ArH), 7.32~7.52 (4H, m, ArH), 12.12 (1H, br, CONH); EI-MS m/e (%): 384.1 ($M^+$, 37), 248.2 (83), 205.1 (100); HREI-MS Calcd. for $C_{20}H_{20}N_2O_4S$: 384.1144. found: 384.1146.

Example 66

Preparation of N-[5-n-butyl-4-(4-hydroxy-phenyl)-thiazol-2-yl]-3,4,5-trihydroxy-benzamide

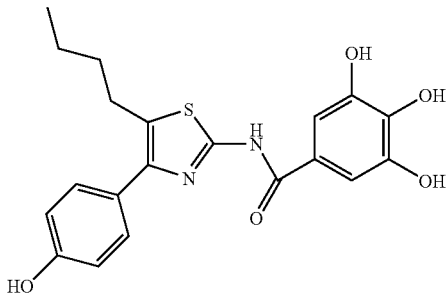

A procedure similar to that in Example 7 was used. N-[5-n-butyl-4-(4-methoxy-phenyl)-thiazol-2-yl]-3,4,5-trimethoxy-benzamide prepared in Example 64 and boron tribromide were used as starting materials, the crude product was purified by recrystallization with acetone to give a product as a white solid in a yield of 47.5%, mp: 119-120 ⌊. $^1$H-NMR (DMSO-$d_6$, 400 MHz) δ: 0.88 (3H, t, J=7.2 Hz, $CH_3$), 1.35 (2H, sextuple, J=7.20 Hz, $CH_2$), 1.63 (2H, quintuple, J=7.20 Hz, $CH_2$), 2.82 (2H, t, J=7.2 Hz, $CH_3$), 6.83 (2H, d, J=8.80 Hz, ArH), 7.08 (2H, s, ArH), 7.40 (2H, d, J=8.80 Hz, ArH), 8.80 (4H, br, OH), 12.12 (1H, br, CONH); EI-MS m/e (%): 400.1 ($M^+$, 14), 248.2 (55), 205.1 (100), 163.1 (38); HREI-MS Calcd. for $C_{20}H_{20}N_2O_5S$: 400.1093. found: 400.1091.

Example 67

Preparation of N-[5-benzyl-4-(4-methoxy-phenyl)-thiazol-2-yl]-N-p-tolylsulfonyl-p-tolylsulfonamide

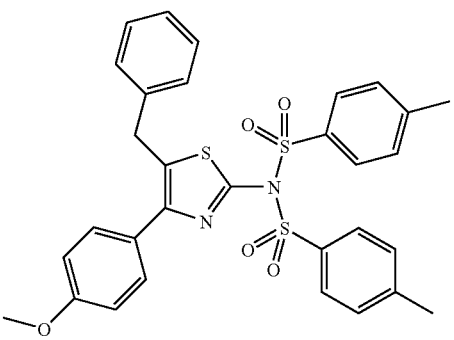

To a 100 ml eggplant-shaped flask were added 1.00 g (3.37 mmol) 5-benzyl-4-(4-methoxy-phenyl)-thiazol-2-ylamine prepared in Example 1, 0.68 g (6.75 mmol) triethylamine and 25 ml THF, added dropwise 1.28 g (6.74 mmol) p-tolylsulfonyl chloride which was dissolved in 5 ml THF. The resulting mixture was stirred at room temperature for 24 hours, filtered, washed with THF, the mother liquid was concentrated under a reduced pressure to a give crude product, which was recrystallized with acetone to obtain a 1.04 g product as a off-white solid in a yield of 51.0%, mp: 182-183 ⌊. $^1$H-NMR (DMSO-$d_6$, 400 MHz) δ: 2.45 (6H, s, 2×$PhCH_3$), 3.84 (3H, s, $OCH_3$), 4.26 (2H, s, $CH_2$), 6.92 (2H, d, J=8.68 Hz, ArH), 7.18~7.36 (9H, m, ArH), 7.46 (2H, d, J=8.68 Hz, ArH), 7.92 (4H, d, J=8.68 Hz, ArH); EI-MS m/e (%): 604.2 ($M^+$, 19), 450.2 (44), 294.2 (78), 91.1 (100); HREI-MS Calcd. for $C_{31}H_{28}N_2O_5S_3$: 604.1160. found: 604.1165. Anal. Calcd. for $C_{31}H_{28}N_2O_5S_3$: C, 61.57; H, 4.67; N, 4.63. found: C, 61.71; H, 4.49; N, 4.82.

Example 68

Preparation of N-[5-benzyl-4-(4-methoxy-phenyl)-thiazol-2-yl]-3-(3,4-dimethoxy-phenyl)-propanamide

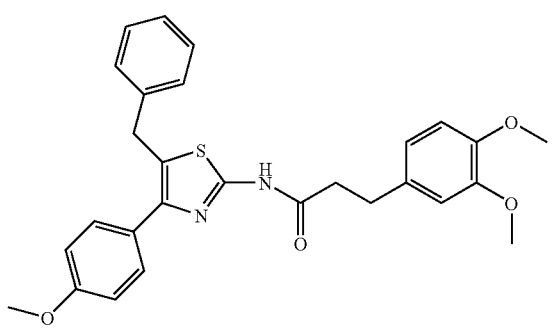

Step 1: Preparation of 3-(3,4-dimethoxy-phenyl)-propionyl chloride 3-(3,4-dimethoxy-phenyl)-propionic acid was converted into 3-(3,4-dimethoxy-phenyl)-propionyl chloride by similar procedure of the step 1 of Example 1, the resultant was a white solid and directly used in the following step without purification.

Step 2: Preparation of N-[5-benzyl-4-(4-methoxy-phenyl)-thiazol-2-yl]-3-(3,4-dimethoxy-phenyl)-propanamide A procedure similar to that in Example 4 was used. 5-benzyl-4-(4-methoxy-phenyl)-thiazol-2-ylamine prepared in Example 1 and 3-(3,4-dimethoxy-phenyl)-propionyl chloride prepared in the step 1 were used as starting materials, allowed to react at 35-40° C. for 10 hours, followed by post-treatment to obtain a crude product, which was purified by a silica gel column chromatography eluted with petroleum ether and ethyl acetate (4:1) to obtain a product as a white solid in a yield of 65.0%, mp: 142-143⌊. $^1$H-NMR (CDCl$_3$, 400 MHz) δ: 2.12 (2H, t, J=7.72 Hz), 2.74 (2H, t, J=7.72 Hz), 3.80 (6H, s, 2×$OCH_3$), 3.83 (3H, s, $OCH_3$), 4.18 (2H, s, $CH_2$), 6.51 (1H, dd, J=8.16, 1.96 Hz, ArH), 6.56 (1H, d, J=1.96 Hz, ArH), 6.69 (1H, d, J=8.16 Hz, ArH), 6.83 (2H, d, J=8.68 Hz, ArH), 7.21~7.33 (5H, m, ArH), 7.42 (2H, d, J=8.68 Hz, ArH), 11.05 (1H, br, CONH); EI-MS m/e (%): 488.1 ($M^+$, 66), 296.0 (100); HREI-MS Calcd. for $C_{28}H_{28}N_2O_4S$: 488.1770. found: 488.1764. Anal. Calcd. for $C_{28}H_{28}N_2O_4S$: C, 68.83; H, 5.78; N, 5.73. found: C, 68.69; H, 5.67; N, 6.09.

Example 69

Preparation of N-[5-benzyl-4-(4-hydroxy-phenyl)-thiazol-2-yl]-3-(3,4-dihydroxy-phenyl)-propanamide

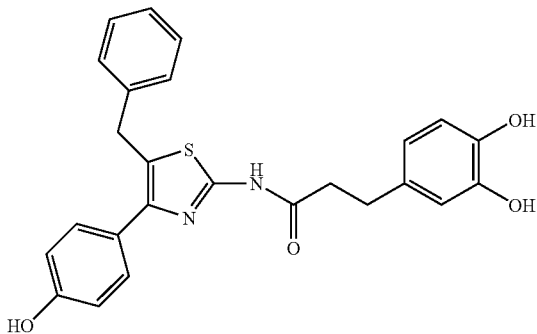

A procedure similar to that in Example 7 was used. N-[5-benzyl-4-(4-methoxy-phenyl)-thiazol-2-yl]-3-(3,4-dimethoxy-phenyl)-propanamide prepared in Example 68 and boron tribromide were used as starting materials, and the crude product was recrystallized with ethyl acetate to obtain a product as a white solid in a yield of 60.3%, mp: 94-95 [. $^1$H-NMR (DMSO-$d_6$, 400 MHz) δ: 2.61 (2H, t, J=7.00 Hz, CH$_2$), 2.68 (2H, t, J=7.00 Hz, CH$_2$), 4.17 (2H, s, CH$_2$), 6.43 (1H, d, J=7.84 Hz, ArH), 6.59 (2H, t, J=7.84 Hz, CH$_2$), 6.80 (2H, d, J=7.84 Hz, ArH), 7.18~7.24 (3H, m, ArH), 7.32 (2H, t, J=7.28 Hz, CH$_2$), 7.41 (2H, d, J=7.84 Hz, ArH), 8.65 (1H, s, OH), 8.74 (1H, s, OH), 9.59 (1H, s, OH), 12.06 (1H, s, CONH); EI-MS m/e (%): 446.1 (M$^+$, 18), 282.1 (100), 205.1 (17); HREI-MS Calcd. for $C_{25}H_{22}N_2O_4S$: 446.1300. found: 446.1299.

Example 70

Preparation of 4-[5-benzyl-4-(4-methoxy-phenyl)-thiazol-2-yl]-morpholine

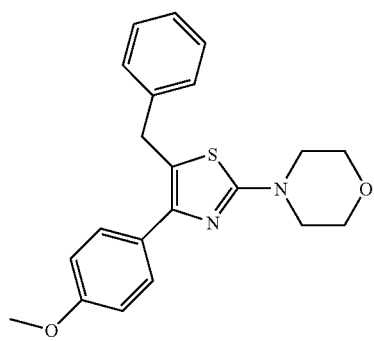

Step 1: Preparation of 5-benzyl-2-chloro-4-(4-methoxy-phenyl)-thiazole

To a 100 ml three-necked flask were added 1.00 g (3.37 mmol) 5-benzyl-4-(4-methoxy-phenyl)-thiazol-2-ylamine prepared in Example 1 and 15 ml acetonitrile. The resulting mixture was stirred to be dissolved, cooled in ice-bath to 0° C., added 0.69 g (4.04 mmol) cupric chloride monohydrate, and added dropwise 0.59 g (5.06 mmol) isoamyl nitrite dissolved in 5 ml acetonitrile. Upon the completion of addition, the resulting mixture was stirred at this temperature for 1 hour and then at room temperature for 1 hour, and removed acetonitrile by rotary evaporation. To the residue was added 10 ml ethyl acetate, and the suspension was filtered through a short silica gel column, eluted with ethyl acetate. The filtrate was concentrated, purified under a reduced pressure by silica gel column chromatography eluted with a gradient of petroleum ether and ethyl acetate at a ratio of 20:1-10:1 (V:V) to obtain a 0.55 g product as a white solid in a yield of 51.9%, mp: 78-79 [. $^1$H-NMR (CDCl$_3$, 400 MHz) δ: 3.84 (3H, s, OCH$_3$), 4.21 (2H, s, CH$_2$), 6.95 (2H, d, J=8.96 Hz, ArH), 7.18~7.38 (5H, m, ArH), 7.54 (2H, d, J=8.96 Hz, ArH); ESI-MS m/e (%): 315.9 (M+1, 100).

Step 2: Preparation of 4-[5-benzyl-4-(4-methoxy-phenyl)-thiazol-2-yl]-morpholine To 25 ml eggplant-shaped bottle were added 1.00 g (3.17 mmol) 5-benzyl-2-chloro-4-(4-methoxy-phenyl)-thiazole prepared in the step 1, 0.27 g (6.34 mmol) LiOH.H$_2$O, 20 mg KI, 0.55 g (6.34 mmol) morpholine, 5 ml DMF and 0.5 ml water. The mixture was stirred until homogeneous, heated to 100° C., stirred for 20 hours, added 20 ml water, and extracted with ethyl acetate 3×10 ml. The organic phases were combined, washed with saturated brine, dried over anhydrous sodium sulfate, filtered, and concentrated to obtain a thick crude product, which was purified under a reduced pressure by silica gel column chromatography eluted with petroleum ether and ethyl acetate at a ratio 4:1-3:1 (V:V) to give a 0.73 g product as a white solid in a yield of 62.9%, mp: 88-89 [. $^1$H-NMR (CDCl$_3$, 400 MHz) δ: 3.47 (4H, m, 2×CH$_2$), 3.80 (4H, t, J=5.2 Hz, 2×CH$_2$), 3.82 (3H, s, OCH$_3$), 4.12 (2H, s, CH$_2$), 6.92 (2H, d, J=8.40 Hz, ArH), 7.18~7.32 (5H, m, ArH), 7.53 (2H, d, J=8.40 Hz, ArH); EI-MS m/e (%): 366.1 (M$^+$, 100), 309.1 (23); HREI-MS Calcd. for $C_{21}H_{22}N_2O_2S$: 366.1402. found: 366.1404. Anal. Calcd. for $C_{21}H_{22}N_2O_2S$: C, 68.83; H, 6.05; N, 7.64. found: C, 68.73; H, 6.26; N, 7.83.

Example 71

Preparation of 1-[5-benzyl-4-(4-methoxy-phenyl)-thiazol-2-yl]-piperazine

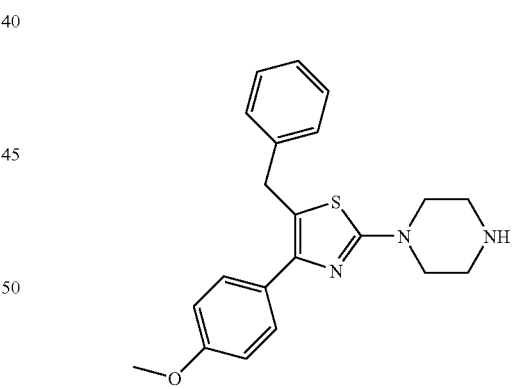

To 25 ml eggplant-shaped bottle were added 1.30 g (4.12 mmol) 5-benzyl-2-chloro-4-(4-methoxy-phenyl)-thiazole prepared in the step 1 of Example 70, 0.35 g (8.24 mmol) LiOH.H$_2$O, 20 mg KI, 1.77 g (20.6 mmol) piperazine, 5 ml DMF and 0.5 ml water. The mixture was stirred until homogeneous, heated to 100° C., stirred for 12 hours, added 20 ml water, and extracted with ethyl acetate three 3×10 ml. The organic phases were combined, washed with saturated brine, dried over anhydrous sodium sulfate, filtered, and concentrated to obtain a thick crude product, which was purified under a reduced pressure by silica gel column chromatography eluted with dichloromethane and methanol at a ratio 10:1-5:1 (V:V) to give a 1.05 g oily and thick product in a yield of 69.5%, $^1$H-NMR (CDCl$_3$, 400 MHz) δ: 2.99 (4H, t, J=5.2 Hz, 2×CH$_2$), 3.46 (4H, t, J=5.2 Hz, 2×CH$_2$), 3.82 (3H, s, OCH$_3$), 4.12 (2H, s, CH$_2$), 6.90 (2H, d, J=8.80 Hz, ArH), 7.18~7.35 (5H, m, ArH), 7.53 (2H, d, J=8.80 Hz, ArH); EI-MS m/e (%): 365.0 (M$^+$, 86), 323.0 (28), 309.0 (100), 296.0 (49); HREI-MS Calcd. for C$_{21}$H$_{23}$N$_3$OS: 365.1562. found: 365.1564.

Example 72

Preparation of 1-[5-benzyl-4-(4-methoxy-phenyl)-thiazol-2-yl]-piperazine trihydrochloride

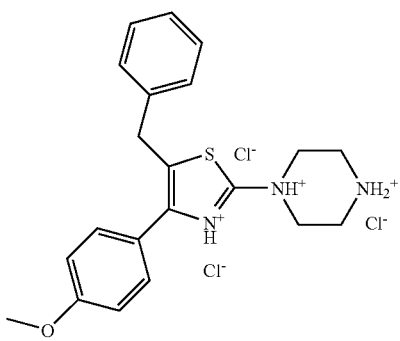

0.4 g (1.09 mmol) 1-[5-benzyl-4-(4-methoxy-phenyl)-thiazol-2-yl]-piperazine prepared in Example 71 was dissolved in 20 ml ethyl acetate, cooled in ice-bath, added a 2 mol/L solution of hydrochloride in ethyl acetate under stirring, and a yellow solid was produced, which was filtered in vacuo, and washed with ethyl acetate to give 3.4 g product as a yellow solid in a yield of 77.3%, mp: 111-112 [. $^1$H-NMR (DMSO-d$_6$, 400 MHz) δ: 3.19 (4H, m, 2×CH$_2$), 3.62 (4H, m, 2×CH$_2$), 3.79 (3H, s, OCH$_3$), 4.12 (2H, s, CH$_2$), 5.58 (2H, br, exchangeable, 2×NH), 6.98 (2H, d, J=8.80 Hz, ArH), 7.18~7.32 (5H, m, ArH), 7.52 (2H, d, J=8.80 Hz, ArH), 9.34 (2H, br, exchangeable, 2×NH); EI-MS m/e (%): 365.0 (M−3, 81), 323.0 (26), 309.0 (100), 295.9 (51); HREI-MS Calcd. for C$_{21}$H$_{23}$N$_3$OS: 365.1562. found: 365.1564.

Example 73

Preparation of 2-[[5-benzyl-4-(4-methoxy-phenyl)-thiazol-2-yl]-(2-hydroxy-ethyl)-amino]-ethanol

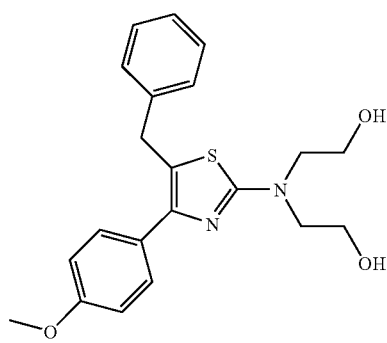

To 25 ml eggplant-shaped bottle were added 1.30 g (4.12 mmol) 5-benzyl-2-chloro-4-(4-methoxy-phenyl)-thiazole prepared in the step 1 of Example 70, 0.35 g (8.24 mmol) LiOH.H$_2$O, 20 mg KI, 0.87 g (8.24 mmol) piperazine, 5 ml DMF and 0.5 ml water. The mixture was stirred until homogeneous, heated to 100° C., stirred for 12 hours, added 20 ml water, and extracted with ethyl acetate 3×10 ml. The organic phases were combined, washed with saturated brine, dried over anhydrous sodium sulfate, filtered, and concentrated to obtain a crude product as a off-white solid, which was purified under a reduced pressure by silica gel column chromatography eluted with dichloromethane and methanol at a ratio 10:1 (V:V) to give an oily and thick product, which was recrystallized with petroleum ether and ethyl acetate to obtain a 0.98 g white solid in a yield of 62.0%, mp: 119-120 [. $^1$H-NMR (CDCl$_3$, 400 MHz) δ: 3.62 (4H, t, J=5.2 Hz, 2×CH$_2$), 3.81 (3H, s, OCH$_3$), 3.88 (4H, t, J=5.2 Hz, 2×CH$_2$), 4.09 (2H, s, CH$_2$), 6.90 (2H, d, J=8.80 Hz, ArH), 7.18~7.35 (5H, m, ArH), 7.48 (2H, d, J=8.80 Hz, ArH); EI-MS m/e (%): 384.1 (M$^+$, 80), 353.1 (64), 309.0 (100), 295.1 (15); HREI-MS Calcd. for C$_{21}$H$_{24}$N$_2$O$_3$S: 384.1508. found: 384.1504. Anal. Calcd. for C$_{21}$H$_{24}$N$_2$O$_3$S: C, 65.60; H, 6.29; N, 7.29. found: C, 65.42; H, 6.56; N, 7.34.

Example 74

Preparation of 4-(5-benzyl-2-morpholin-4-yl-thiazol-4-yl)-phenol

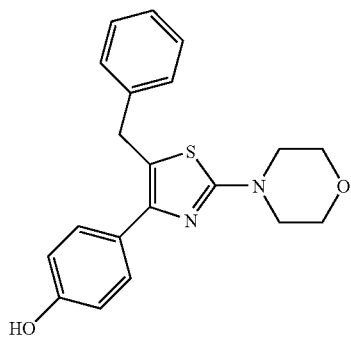

To 50 ml eggplant-shaped bottle were added 0.60 g (1.64 mmol) 4-[5-benzyl-4-(4-methoxy-phenyl)-thiazol-2-yl]-morpholine prepared in Example 70 and 20 ml dichloromethane. The resulting mixture was cooled in ice-bath, added dropwise 2.4 ml (4.92 mmol) 2.034 mol/L solution of boron tribromide in dichloromethane, stirred in ice-bath for 1 hour and then at room temperature for 3 hours, added 2 g ice to decompose the complex. The resulting mixture was concentrated under a reduced pressure to remove dichloromethane, dissolved in 100 ml ethyl acetate, and washed with saturated brine, dried over anhydrous sodium sulfate, concentrated, purified under a reduced pressure by silica gel column chromatography eluted with dichloromethane and methanol at a ratio 10:1-5:1 (V:V) to give a 0.26 g pale yellow thick liquid in a yield of 44.8%, $^1$H-NMR (DMSO-d$_6$, 400 MHz) δ: 3.50 (2H, m, CH$_2$), 3.63 (2H, m, CH$_2$), 3.97 (2H, s, CH$_2$), 4.27 (4H, s, CH$_2$), 5.18 (1H, m), 6.97 (2H, d, J=8.40 Hz, ArH), 7.15~7.40 (7H, m, ArH), 10.14 (1H, s, OH); EI-MS m/e (%): 352.0 (M+, 37), 322.0 (100), 240.0 (48); HREI-MS Calcd. for C20H20N2O2S: 352.1245. found: 352.1243.

Example 75

Preparation of 4-(5-benzyl-2-piperazin-4-yl-thiazol-4-yl)-phenol

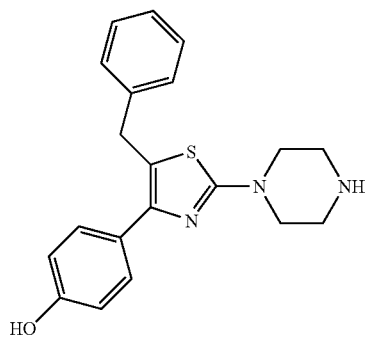

A procedure similar to that in Example 74 was used. 1-[5-benzyl-4-(4-methoxy-phenyl)-thiazol-2-yl]-piperazine prepared in Example 71 and a solution of boron tribromide in dichloromethane were used as starting materials. The obtained crude product was recrystallized with acetone to give a product as a white solid in a yield of 49.2%, mp: 222-223 ⌊. 1H-NMR (DMSO-d6, 400 MHz) δ: 2.71 (2H, s, CH2), 3.20 (2H, m, CH2), 3.40 (1H, br, NH), 4.01 (2H, s, CH2), 6.70 (2H, d, J=8.00 Hz, ArH), 7.05~7.25 (2H, m, ArH), 7.31 (2H, d, J=8.00 Hz, ArH), 9.48 (1H, s, OH); EI-MS m/e (%): 351.1 (M+, 77), 309.0 (29), 295.0 (100), 282.0 (42); HREI-MS Calcd. for C20H21N3OS: 351.1405. found: 351.1406.

Example 76

Preparation of 4-(5-benzyl-2-[bis-(2-hydroxy-ethyl)-amino]-thiazol-4-yl)-phenol

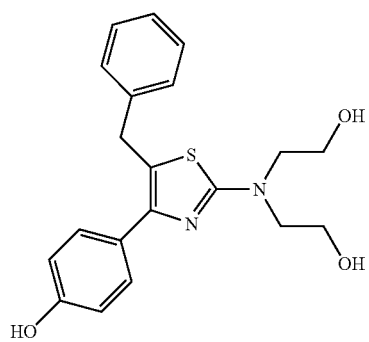

A procedure similar to that in Example 74 was used. 2-[[5-benzyl-4-(4-methoxy-phenyl)-thiazol-2-yl]-(2-hydroxy-ethyl)-amino]-ethanol prepared in Example 73 and a solution of boron tribromide in dichloromethane were used as starting materials. The obtained crude product was recrystallized with acetone to give a product as a white solid in a yield of 54.7%, mp: 167-168 ⌊. 1H-NMR (DMSO-d6, 400 MHz) δ: 3.46 (2H, t, J=6.40 Hz, CH2), 3.59 (2H, t, J=6.40 Hz, CH2), 4.04 (2H, s, CH2), 4.88 (2H, t, J=5.20 Hz, 2×OH), 6.78 (2H, d, J=8.80 Hz, ArH), 7.15~7.28 (5H, m, ArH), 7.36 (2H, d, J=8.80 Hz, ArH), 9.54 (1H, br, OH); EI-MS m/e (%): 370.1 (M+, 75), 339.1 (74), 309.0 (17), 295.0 (100); HREI-MS Calcd. for C20H22N2O3S: 370.1351. found: 370.1349. Anal. Calcd. for C20H22N2O3S: C, 64.84; H, 5.99; N, 7.56. found: C, 64.86; H, 5.89; N, 7.61.

Example 77

Preparation of 5-benzyl-2-[2-(3,4-dimethoxy-phenyl)-ethyl]-4-(4-methoxy-phenyl)-thiazole

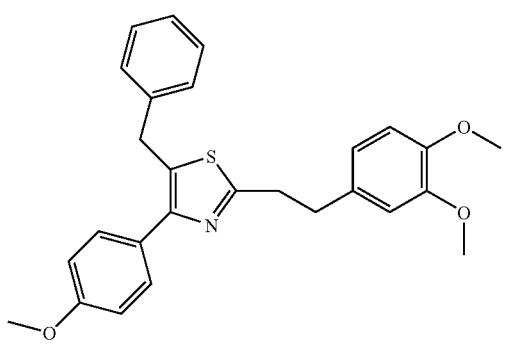

Step 1: Preparation of 3-(3,4-dimethoxy-phenyl)-propionic acid tert-butoxyformic acid mixed anhydride To a 50 ml three-necked flask were added 0.50 g (2.38 mmol) 3-(3,4-dimethoxy-phenyl)-propionic acid, 5 ml THF and 0.5 g triethylamine, cooled in ice-bath to 0-5° C., added dropwise a solution of iso-butyl chlorocarbonate dissolved in 3 ml THF, upon the completion of the addition, stirred at room temperature for 1 hour, pump filtered to remove triethylamine hydrochloride, washed with THF to obtain a solution of the titled mixed anhydride, which was directly used in the following step.

Step 2: preparation of 3-(3,4-dimethoxy-phenyl)-propanamide

To a 50 ml three-necked flask was added 5 ml 25% ammonia water. The resulting mixture was cooled in ice-bath to 0-5° C., and added dropwise the mixed anhydride solution prepared in the step 1. Upon the completion of addition, stirred at room temperature for 2 hours, and concentrated under a reduced pressure. The residue was partitioned between water and ethyl acetate each 10 ml, and the aqueous phase was washed with ethyl acetate 2×5 ml. The organic phase was combined, washed with 1 mol/L HCl, saturated brine, saturated NaHCO3 and saturated brine successively, dried over anhydrous Na2SO4, filtered and concentrated to obtain a 290 mg white solid in a yield of 58.0%, mp: 122-123 ⌊. 1H-NMR (CDCl3, 400 MHz) δ: 2.52 (2H, t, J=7.84 Hz, CH2), 2.93 (2H, t, J=7.84 Hz, CH2), 3.86 (3H, s, CH3O), 3.87 (3H, s, CH3O), 5.40 (2H, s, NH2), 6.72~6.82 (3H, m, ArH); ESI-MS (m/e, %): 232.2 (M+Na, 61), 227.5 (M+NH3+H, 16), 210.2 (M+H, 100).

Step 3: preparation of 3-(3,4-dimethoxy-phenyl)-thiopropanamide

To a 25 ml eggplant-shaped bottle were added 0.15 g (0.717 mmol) 3-(3,4-dimethoxy-phenyl)-propanamide prepared in step 2, 0.16 g (0.717 mmol) P$_2$S$_5$ and 10 ml THF. A reflux condensing tube carrying a calcium chloride drying tube was mounted. The mixture was refluxed for 1 hour under magnetic agitation, concentrated under a reduced pressure, partitioned between ethyl acetate and saturated NaHCO$_3$ solution each of 15 ml. The aqueous layer was extracted with ethyl acetate twice ×10 ml. The organic phase was combined, washed with saturated brine twice ×15 ml, dried over Na$_2$SO$_4$, filtered and concentrated to obtain a solid crude product which was purified under a reduced pressure by silica gel column chromatography eluted with petroleum ether and ethyl acetate at a ratio of 10:1 (V:V) to obtain a 0.11 g product as a white solid in a yield of 68.8%, mp: 140-141 [. $^1$H-NMR (CDCl$_3$, 600 MHz) δ: 2.93 (2H, t, J=7.20 Hz, CH$_2$), 3.07 (2H, t, J=7.84 Hz, CH$_2$), 3.86 (3H, s, CH$_3$O), 3.87 (3H, s, CH$_3$O), 6.62 (1H, br), 6.75~6.82 (3H, m, ArH), 7.35 (1H, br); ESI-MS (m/e, %): 248.3 (M+Na, 100), 226.3 (M+H, 64).

Step 4: Preparation of 5-benzyl-2-[2-(3,4-dimethoxy-phenyl)-ethyl]-4-(4-methoxy-phenyl)-thiazole To a 50 ml eggplant-shaped bottle were added 0.12 g (0.533 mmol) 3-(3,4-dimethoxy-phenyl)-thiopropanamide prepared in the step 3, 0.17 g (0.533 mmol) 2-bromo-1-(4-methoxy-phenyl)-3-phenyl-propan-1-one prepared in the step 3 of Example 1, 0.04 g (0.533 mmol) anhydrous sodium acetate and 20 ml anhydrous ethanol. The resulting mixture was refluxed for 4 hours, when TLC showed the completion of the reaction, and concentrated under a reduced pressure. The reaction mixture was partitioned between water and ethyl acetate each 20 ml, the ethyl acetate layer was washed with saturated brine 2×10 ml, dried over anhydrous Na$_2$SO$_4$, filtered and concentrated to give a solid crude product which was recrystallized with petroleum ether and ethyl acetate to obtain a 0.17 g product as a thick liquid in a yield of 70.8%. $^1$H-NMR (CDCl$_3$, 400 MHz) δ: 3.06 (2H, t, J=8.40 Hz, CH$_2$), 3.25 (2H, t, J=8.40 Hz, CH$_2$), 3.83 (3H, s, CH$_3$O), 3.84 (3H, s, CH$_3$O), 3.86 (3H, s, CH$_3$O), 4.20 (2H, s, CH$_2$), 6.70~6.80 (3H, m, ArH), 6.95 (2H, d, J=8.80 Hz, ArH), 7.15~7.35 (5H, m, ArH), 7.54 (2H, d, J=8.80 Hz, ArH); EI-MS m/e (%): 445.1 (M, 100), 151.1 (93); HREI-MS Calcd. for C$_{27}$H$_{27}$NO$_3$S: 445.1712. found: 445.1716.

Example 78

Preparation of 4-{2-[5-benzyl-4-(4-hydroxy-phenyl)-thiazol-2-yl]-ethyl}-benzene-1,2-diol

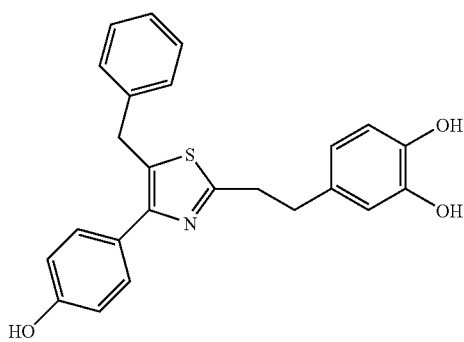

A procedure similar to that in Example 7 was used. 5-benzyl-2-[2-(3,4-dimethoxy-phenyl)-ethyl]-4-(4-methoxy-phenyl)-thiazole prepped in step 4 of Example 77 and boron tribromide were as starting materials, the crude product was recrystallized with acetone to obtain a product as a white solid in a yield of 52.2%, mp: 177-178 [. $^1$H-NMR (DMSO-d$_6$, 400 MHz) δ: 2.82 (2H, t, J=8.16 Hz, ArH), 3.11 (2H, t, J=8.16 Hz, ArH), 4.20 (2H, s, CH$_2$), 6.48 (1H, d, J=8.12 Hz, ArH), 6.58~6.64 (2H, m, ArH), 6.82 (2H, d, J=8.40 Hz, ArH), 7.14~7.26 (3H, m, ArH), 7.32 (2H, t, J=7.28 Hz, ArH), 7.44 (2H, d, J=8.40 Hz, ArH), 8.69 (1H, s, OH), 8.75 (1H, s, OH), 9.61 (1H, s, OH); EI-MS m/e (%): 403.2 (M$^+$, 67), 281.2 (100); HREI-MS Calcd. for C$_{24}$H$_{21}$NO$_3$S: 403.1242. found: 403.1238.

PLTP inhibition activity and CETP inhibition activity of the compounds of the present invention can be determined by following methods:

Example 79

Determination Method of PLTP Inhibition Activity

30 μl (about 1000 cpm/μl) phospholipids liposome, 30 μl HDL (6.0 g protein/μl), 337 μl TSE and 3 μl plasma were mixed, incubated in 37° C. water-bath for 1 hour, and then added 300 μl of a settling solution (50 ml solution preparation: 5.36 ml 5N NaCl, 9.075 ml 2M MnCl$_2$ and 46 mg liver phospholipid were mixed, added water to 50 ml), the solution was stood at room temperature for 10 minutes, rotated at high speed for 10 minutes (to remove phospholipids liposome), 500 μl of the supernatant was sampled and counted. PLTP activity (cpm/h/3 μl)=sample cpm-background cpm.

Example 80

Determination Method of CETP Inhibition Activity

A mixture containing 3 μl of a donor, 9 μl of an acceptor (250 μg protein), 3 μl of CETP solution and 85 μl of an analytic buffer, 10 mM Tris, 0.15 M NaCl and 2 mM EDTA, pH 7.4 was incubated at 37° C. for 0.5 hours, the fluorescence intensity was determined on Victor 3 double illuminometer/fluorescence counter (Perkin Elmer) carrying 460 nm emission light wave length and 530 nm excitation light wave length.

The determination results of PLTP inhibition activity and CETP inhibition activity were shown in table 1.

TABLE 1

Determination results of PLTP inhibition activity and CETP inhibition activity

| Example No. | PLTP inhibition activity | | | CETP inhibition activity | | |
|---|---|---|---|---|---|---|
| | Concentration of compounds (μM) | Inhibition rate(%) | IC$_{50}$ (μM) | Concentration of compounds(μM) | Inhibition rate(%) | IC$_{50}$ (μM) |
| 8 | 150 | 0 | — | 500 | 80.4 | — |
| 19 | 250 | 79.8 | 70 | 500 | 19.4 | — |
| 21 | 250 | 11.5 | — | 500 | 52.8 | — |
| 31 | 250 | 100 | 75 | 500 | 0 | — |
| 32 | 250 | 100 | 75 | 500 | 0 | — |
| 33 | 250 | 73.2 | 100 | 500 | 9.2 | — |
| 34 | 250 | 67.6 | 100 | 500 | 30.4 | — |
| 38 | 150 | 11.5 | — | 500 | 88.0 | — |
| 40 | 150 | 0 | — | 500 | 71.6 | — |
| 41 | 150 | 89.4 | 15 | 500 | 44.1 | — |
| 47 | 150 | 0 | — | 500 | 79.8 | — |
| 49 | 150 | 81.6 | 35 | 500 | 6.0 | — |
| 51 | 250 | 100 | 18 | 500 | 20.9 | — |
| 55 | 250 | 10.7 | — | 500 | 85.9 | — |
| 56 | 250 | 71.9 | 75 | 500 | 58.7 | — |
| 57 | 250 | 24.0 | — | 500 | 75.8 | — |
| 60 | 250 | 97.0 | 35 | 500 | 0 | — |
| 62 | 250 | 15.3 | — | 500 | 65.4 | — |
| 65 | 250 | 93.4 | 75 | 500 | 0 | — |
| 66 | 250 | 100 | 75 | 500 | 27.3 | — |
| 69 | 150 | 75.7 | 75 | 500 | 25.3 | — |
| 70 | 500 | 61.0 | — | 500 | 91.6 | 75 |
| 72 | 500 | 100 | — | 500 | 74.5 | — |

What is claimed is:

1. A compound of formula (Ia):

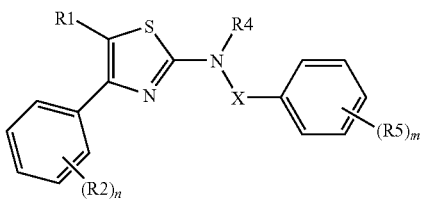

(Ia)

wherein,

R1 is phenyl-$C_1$-$C_6$alkyl or $C_3$-$C_{10}$cycloalkyl-$C_1$-$C_6$alkyl, wherein phenyl is unsubstituted or substituted with one, two or three substituents independently selected from halogen, nitro, hydroxyl, amino, cyano, $C_1$-$C_6$alkyl, $C_1$-$C_6$alkoxy and $C_{1-6}$haloalkyl; and wherein said alkyl in said alkyl in said phenyl-$C_1$-$C_6$alkyl or $C_3$-$C_{10}$cycloalkyl-$C_1$-$C_6$alkyl and said cycloalkyl in said $C_3$-$C_{10}$cycloalkyl-$C_1$-$C_6$alkyl may be optionally substituted with hydroxyl, oxo or amino, or optionally spaced by —O—, —S—, —NH—, —COO—, or —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

R4 is hydrogen, benzoyl or phenylsulfonyl; wherein the phenyl in benzoyl and phenylsulfonyl is optionally substituted with one or two substituents independently selected from hydroxyl, halogen, nitro, amino, cyano, $C_1$-$C_6$alkyl, $C_1$-$C_6$alkoxy and $C_{1-6}$haloalkyl;

each R5 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

X is —(C=O)—;

n is 0, 1, 2 or 3; and m is 0, 1, 2, 3 or 4, or pharmaceutically acceptable salt thereof.

2. The compound of claim 1, wherein the compound has the formula (Iaa):

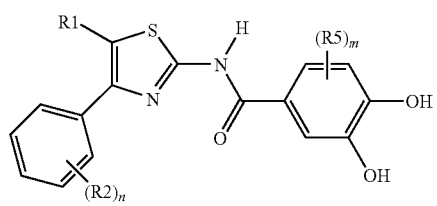

(Iaa)

wherein,

R1 is phenyl-$C_1$-$C_6$alkyl or $C_3$-$C_{10}$cycloalkyl-$C_1$-$C_6$alkyl, wherein phenyl is unsubstituted or substituted with one or two substituents independently selected from halogen, nitro, hydroxyl, amino, cyano, $C_1$-$C_6$alkyl, $C_1$-$C_6$alkoxy and $C_{1-6}$haloalkyl; and wherein said alkyl in said phenyl-$C_1$-$C_6$alkyl or $C_3$-$C_{10}$cycloalkyl-$C_1$-$C_6$alkyl and said cycloalkyl in said $C_3$-$C_{10}$cycloalkyl-$C_1$-$C_6$alkyl may be optionally substituted with hydroxyl, oxo or amino, or optionally spaced by —O—, —S—, —NH—, —COO—, or —CONH—;

each R2 is independently hydrogen, hydroxyl, halogen, $C_1$-$C_6$alkoxy, $C_1$-$C_6$alkyl, $C_{1-6}$haloalkyl, amino, nitro, cyano or alkylacyl;

each R5 is independently selected from hydrogen, hydroxyl, $C_1$-$C_6$alkyl, $C_1$-$C_6$alkoxy, $C_{1-6}$haloalkyl, amino, halogen, nitro, cyano and alkylacyl;

n is 0, 1 or 2; and m is 0, 1 or 2, or pharmaceutically acceptable salt thereof.

3. The compound of claim 1, wherein the compound is selected from the group consisting of:
(1) N-[5-benzyl-4-(4-methoxy-phenyl)-thiazol-2-yl]-benzamide;
(2) N-[5-benzyl-4-(4-methoxy-phenyl)-thiazol-2-yl]-4-fluoro-benzamide;
(3) N-[5-benzyl-4-(4-methoxy-phenyl)-thiazol-2-yl]-4-chloro-benzamide;
(4) N-[5-benzyl-4-(4-hydroxy-phenyl)-thiazol-2-yl]-4-fluoro-benzamide;
(5) N-[5-benzyl-4-(4-hydroxy-phenyl)-thiazol-2-yl]-4-chloro-benzamide;
(6) 4-fluoro-N-[4-(4-methoxy-phenyl)-5-(4-nitro-benzyl)-thiazol-2-yl]-benzamide;
(7) 4-fluoro-N-[4-(4-fluoro-phenyl)-5-(4-nitro-benzyl)-thiazol-2-yl]-benzamide;
(8) N-[5-benzyl-4-(4-methoxy-phenyl)-thiazol-2-yl]-3,4-dimethoxy-benzamide;
(9) N-[5-benzyl-4-(4-methoxy-phenyl)-thiazol-2-yl]-4-cyano-benzamide;
(10) 4-cyano-N-[4-(4-methoxy-phenyl)-5-(4-nitro-benzyl)-thiazol-2-yl]-benzamide;
(11) 4-cyano-N-[4-(4-fluoro-phenyl)-5-(4-nitro-benzyl)-thiazol-2-yl]-benzamide;
(12) N-(5-benzyl-4-(4-methoxy-phenyl)-thiazol-2-yl]-3,5-difluoro-benzamide;
(13) 3,5-difluoro-N-[4-(4-methoxy-phenyl)-5-(4-nitro-benzyl)-thiazol-2-yl]-benzamide;
(14) 3,5-difluoro-N-[4-(4-fluoro-phenyl)-5-(4-nitro-benzyl)-thiazol-2-yl]-benzamide;
(15) N-[5-benzyl-4-(4-hydroxyl-phenyl)-thiazol-2-yl]-3,4-dihydroxyl-benzamide;
(16) N-[4-(4-fluoro-phenyl)-5-(4-nitro-benzyl)-thiazol-2-yl]-3,4-dimethoxy-benzamide;
(17) 3,5-difluoro-N-[5-(4-fluoro-benzyl)-4-(4-methoxy-phenyl)-thiazol-2-yl]-benzamide;
(18) 4-fluoro-N-[5-(4-fluoro-benzyl)-4-(4-methoxy-phenyl)-thiazol-2-yl]-benzamide;
(19) N-[5-(4-fluoro-benzyl)-4-(4-methoxy-phenyl)-thiazol-2-yl]-N-(3,4-dimethoxy-benzamido)-3,4-dimethoxy-benzamide;
(20) 4-cyano-N-[5-(4-fluoro-benzyl)-4-(4-methoxy-phenyl)-thiazol-2-yl]-benzamide;
(21) N-[5-benzyl-4-(4-methoxy-phenyl)-thiazol-2-yl]-4-methoxy-benzamide;
(22) 3,4-dimethoxy-N-[4-(4-methoxy-phenyl)-5-(4-nitro-benzyl)-thiazol-2-yl]-benzamide;
(23) 3,4-dimethoxy-N-[5-(4-nitro-benzyl)-4-phenyl-thiazol-2-yl]-benzamide;
(24) N-[5-(4-fluoro-benzyl)-4-(4-methoxy-phenyl)-thiazol-2-yl]-3,4-dimethoxy-benzamide;
(25) N-[4-(4-fluoro-phenyl)-5-(4-nitro-benzyl)-thiazol-2-yl]-3,4-dihydroxy-benzamide;
(26) 3,4-dihydroxy-N-[5-(4-nitro-benzyl)-4-phenyl-thiazol-2-yl]-benzamide;
(27) N-[5-(4-fluoro-benzyl)-4-(4-hydroxy-phenyl)-thiazol-2-yl]-3,4-dihydroxy-benzamide;
(28) 3,4-dihydroxy-N-[4-(4-hydroxy-phenyl)-5-(4-nitro-benzyl)-thiazol-2-yl]-benzamide;
(29) N-[5-benzyl-4-(4-methoxy-phenyl)-thiazol-2-yl]-2,4-dimethoxy-benzamide;
(30) N-[5-benzyl-4-(4-methoxy-phenyl)-thiazol-2-yl]-2-methoxy-benzamide;
(31) N-[5-benzyl-4-(4-methoxy-phenyl)-thiazol-2-yl]-3,4,5-trimethoxy-benzamide;
(32) N-[5-benzyl-4-(4-hydroxy-phenyl)-thiazol-2-yl]-2,4-dihydroxy-benzamide;
(33) N-[5-benzyl-4-(4-hydroxy-phenyl)-thiazol-2-yl]-2-hydroxy-benzamide;
(34) N-[5-benzyl-4-(4-hydroxy-phenyl)-thiazol-2-yl]-4-methoxy-benzamide;
(35) N-[5-benzyl-4-(4-hydroxy-phenyl)-thiazol-2-yl]-3,4,5-trihydroxy-benzamide;
(36) N-[5-benzyl-4-(4-methoxy-phenyl)-thiazol-2-yl]-3-methoxy-benzamide;
(37) N-[5-benzyl-4-(4-methoxy-phenyl)-thiazol-2-yl]-3,5-dimethoxy-benzamide;
(38) N-[5-benzyl-4-(4-hydroxy-phenyl)-thiazol-2-yl]-3-hydroxy-benzamide;
(39) N-[5-benzyl-4-(4-hydroxy-phenyl)-thiazol-2-yl]-3,5-dihydroxy-benzamide;
(40) N-[5-benzyl-4-(4-hydroxy-phenyl)-thiazol-2-yl]-4-hydroxy-benzamide;
(41) N-[5-cyclohexylmethyl-4-(4-methoxy-phenyl)-thiazol-2-yl]-3,4-dimethoxy-benzamide;
(42) N-[5-cyclohexylmethyl-4-(4-hydroxy-phenyl)-thiazol-2-yl]-3,4-dihydroxy-benzamide;
(43) N-[5-cyclohexylmethyl-4-(4-hydroxy-phenyl)-thiazol-2-yl]-3,4,5-trimethoxy-benzamide;
(44) N-[5-cyclohexylmethyl-4-(4-hydroxy-phenyl)-thiazol-2-yl]-3,4,5-trihydroxy-benzamide;
(45) 3,4-dimethoxy-N-[4-(4-methoxy-phenyl)-5-phenyl-ethyl-thiazol-2-yl]-benzamide;
(46) 3,4,5-trimethoxy-N-[4-(4-methoxy-phenyl)-5-phenylethyl-thiazol-2-yl]-benzamide;
(47) 3,4-dihydroxy-N-[4-(4-hydroxy-phenyl)-5-phenyl-ethyl-thiazol-2-yl]-benzamide; and
(48) 3,4,5-trihydroxy-N-[4-(4-hydroxy-phenyl)-5-phenyl-ethyl-thiazol-2-yl]-benzamide;
or pharmaceutically acceptable salt thereof.

4. A pharmaceutical composition, the composition comprising:
the compound of claim 1, and
at least one pharmaceutically acceptable carrier.

* * * * *